(12) United States Patent
Hara et al.

(10) Patent No.: US 11,456,424 B2
(45) Date of Patent: Sep. 27, 2022

(54) PHOSPHORESCENT HOST MATERIAL

(71) Applicant: Semiconductor Energy Laboratory Co., Ltd., Kanagawa-ken (JP)

(72) Inventors: Tomoka Hara, Kanagawa (JP); Hideko Yoshizumi, Kanagawa (JP); Hiromitsu Kido, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 368 days.

(21) Appl. No.: 16/622,489

(22) PCT Filed: Jun. 13, 2018

(86) PCT No.: PCT/IB2018/054279
§ 371 (c)(1),
(2) Date: Dec. 13, 2019

(87) PCT Pub. No.: WO2018/234932
PCT Pub. Date: Dec. 27, 2018

(65) Prior Publication Data
US 2021/0151689 A1 May 20, 2021

(30) Foreign Application Priority Data
Jun. 23, 2017 (JP) .............................. JP2017-123227

(51) Int. Cl.
*H01L 51/00* (2006.01)
*C07D 491/048* (2006.01)
*H01L 51/50* (2006.01)

(52) U.S. Cl.
CPC ...... *H01L 51/0071* (2013.01); *C07D 491/048* (2013.01); *H01L 51/0074* (2013.01); *H01L 51/5016* (2013.01); *H01L 2251/552* (2013.01)

(58) Field of Classification Search
CPC ............ H01L 51/0071; H01L 51/0074; H01L 51/5016; H01L 51/5028; H01L 51/5278; C07D 491/048
(Continued)

(56) References Cited

U.S. PATENT DOCUMENTS 6,602,618 B2  8/2003  Watanabe et al.
9,553,274 B2  1/2017  Xia et al.
(Continued)

FOREIGN PATENT DOCUMENTS

CN    103649080 A    3/2014
CN    105103327 A    11/2015
(Continued)

OTHER PUBLICATIONS

International Search Report re Application No. PCT/IB2018/054279, dated Sep. 18, 2018.
(Continued)

*Primary Examiner* — Sheng-Bai Zhu
(74) *Attorney, Agent, or Firm* — Husch Blackwell LLP

(57) ABSTRACT

A novel compound is provided. A light-emitting element with high emission efficiency and a long lifetime is provided. The compound is an organic compound that includes a benzofuro[3,2-d]pyrimidine or benzothieno[3,2-d]pyrimidine skeleton (General Formula (G0)). The 2-position of the benzofuro[3,2-d]pyrimidine or benzothieno[3,2-d]pyrimidine skeleton has a substituent and the 6- to 9-positions of the skeleton have at least one substituent. Any one of the substituents bonded to the 6- to 9-positions is bonded to the benzofuro[3,2-d]pyrimidine or benzothieno[3,2-d]pyrimidine skeleton via a phenylene group. A light-emitting element including the compound is provided.

13 Claims, 15 Drawing Sheets

(58) Field of Classification Search
USPC .......................................................... 257/40
See application file for complete search history.

(56) References Cited

U.S. PATENT DOCUMENTS

| | | | |
|---|---|---|---|
| 9,905,782 B2 | 2/2018 | Inoue et al. | |
| 10,043,977 B2 | 8/2018 | Kato et al. | |
| 10,193,086 B2 | 1/2019 | Inoue et al. | |
| 10,538,510 B2 | 1/2020 | Lee et al. | |
| 10,586,931 B2 | 3/2020 | Kanamoto et al. | |
| 10,700,291 B2 | 6/2020 | Inoue et al. | |
| 11,088,332 B2 | 8/2021 | Kanamoto et al. | |
| 2010/0231568 A1 | 9/2010 | Yamashita et al. | |
| 2011/0248246 A1* | 10/2011 | Ogita | H05B 33/28 |
| | | | 257/E51.026 |
| 2013/0140549 A1 | 6/2013 | Xia et al. | |
| 2014/0131665 A1 | 5/2014 | Xia et al. | |
| 2014/0291645 A1 | 10/2014 | Inoue et al. | |
| 2015/0021555 A1 | 1/2015 | Kwong et al. | |
| 2015/0021556 A1 | 1/2015 | Xia et al. | |
| 2015/0207082 A1 | 7/2015 | Dyatkin et al. | |
| 2016/0075718 A1 | 3/2016 | Mitsumori et al. | |
| 2016/0093818 A1 | 3/2016 | Inoue et al. | |
| 2016/0172599 A1* | 6/2016 | Ogiwara | C07D 491/147 |
| | | | 548/417 |
| 2016/0240791 A1 | 8/2016 | Lee et al. | |
| 2016/0336517 A1 | 11/2016 | Hirose et al. | |
| 2016/0351829 A1 | 12/2016 | Hosoumi et al. | |
| 2016/0351833 A1 | 12/2016 | Hosoumi et al. | |
| 2017/0069852 A1* | 3/2017 | Kanamoto | H01L 51/0071 |
| 2017/0170409 A1 | 6/2017 | Xia et al. | |
| 2017/0186971 A1 | 6/2017 | Kanamoto et al. | |
| 2018/0155325 A1 | 6/2018 | Lee et al. | |
| 2018/0182976 A1 | 6/2018 | Kurihara et al. | |
| 2019/0013475 A1 | 1/2019 | Kato et al. | |
| 2020/0024282 A1 | 1/2020 | Parham et al. | |
| 2020/0028091 A1 | 1/2020 | Parham et al. | |
| 2021/0013428 A1 | 1/2021 | Inoue et al. | |

FOREIGN PATENT DOCUMENTS

| | | |
|---|---|---|
| CN | 108148047 A | 6/2018 |
| CN | 108431010 A | 8/2018 |
| CN | 109689658 A | 4/2019 |
| CN | 109790173 A | 5/2019 |
| EP | 2 738 166 A1 | 6/2014 |
| EP | 2 826 781 A1 | 1/2015 |
| EP | 3 056 498 A1 | 8/2016 |
| JP | 2010-182699 A | 8/2010 |
| JP | 2011-084531 A | 4/2011 |
| JP | 2013-536196 | 9/2013 |
| JP | 2014-209611 A | 11/2014 |
| JP | 2015-134745 A | 7/2015 |
| JP | 2015-151352 A | 8/2015 |
| JP | 2015-157808 A | 9/2015 |
| JP | 2015-205831 A | 11/2015 |
| JP | 2016-147851 A | 8/2016 |
| JP | 2017-119682 A | 7/2017 |
| JP | 2018-127402 A | 8/2018 |
| KR | 2015-0133998 A | 12/2015 |
| KR | 2018-0022608 A | 3/2018 |
| TW | 201527302 | 7/2015 |
| WO | WO 2014/157599 A1 | 10/2014 |
| WO | WO 2015/037675 A1 | 3/2015 |
| WO | WO 2015/108301 A1 | 7/2015 |
| WO | WO 2017/109637 A1 | 6/2017 |
| WO | WO 2018/060218 A1 | 4/2018 |
| WO | WO 2018/060307 A1 | 4/2018 |

OTHER PUBLICATIONS

Written Opinion re Application No. PCT/IB2018/054279, dated Sep. 18, 2018.
Chinese Office Action (Application No. 201880042005.7) dated Jan. 5, 2022.
Taiwanese Office Action (Application No. 107120096) dated Dec. 10, 2021.

* cited by examiner

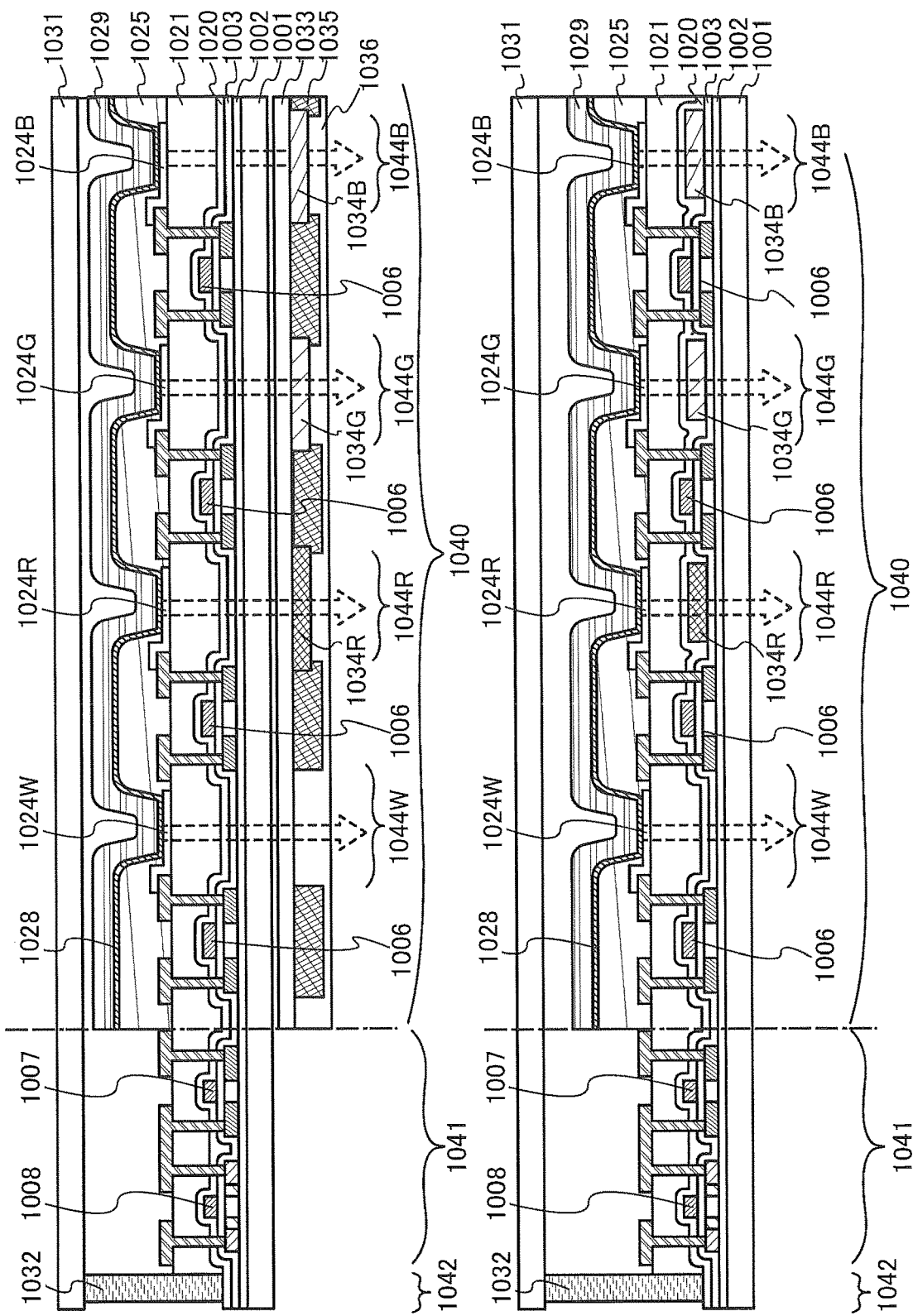

PHOSPHORESCENT HOST MATERIAL

TECHNICAL FIELD

One embodiment of the present invention relates to a novel organic compound. One embodiment of the present invention relates to a benzofuro[3,2-d]pyrimidine compound or a benzothieno[3,2-d]pyrimidine compound. In addition, one embodiment of the present invention relates to a light-emitting element, a light-emitting device, an electronic device, and a lighting device each of which includes the organic compound.

Note that one embodiment of the present invention is not limited to the above technical field. One embodiment of the present invention relates to an object, a method, or a manufacturing method. The present invention relates to a process, a machine, manufacture, or a composition of matter. In particular, one embodiment of the present invention relates to a semiconductor device, a light-emitting device, a display device, a lighting device, a light-emitting element, or a manufacturing method thereof. In addition, one embodiment of the present invention relates to a novel method for synthesizing a benzofuro[3,2-d]pyrimidine compound or a benzothieno[3,2-d]pyrimidine compound. Thus, specific examples of one embodiment of the present invention disclosed in this specification include a light-emitting element, a light-emitting device, an electronic device, and a lighting device, each of which includes the organic compound, and a manufacturing method thereof.

BACKGROUND ART

Light-emitting elements (organic EL elements) including organic compounds and utilizing electroluminescence (EL) have been put to more practical use. In the basic structure of such light-emitting elements, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

The light-emitting elements are self-luminous elements and thus have advantages such as high visibility and no need for backlight when used as pixels of a display, and are suitable as flat panel display elements. Displays including such light-emitting elements are also highly advantageous in that they can be thin and lightweight. Moreover, such a light-emitting element also has a feature that response speed is extremely fast.

Since light-emitting layers of such light-emitting elements can be successively formed two-dimensionally, planar light emission can be achieved. This feature is difficult to obtain with point light sources typified by incandescent lamps and LEDs or linear light sources typified by fluorescent lamps. Furthermore, light emission from an organic compound can be light emission which does not include UV light by selecting a material; thus, light-emitting elements also have great potential as planar light sources used in lighting devices and the like.

Displays or lighting devices including organic EL elements can be suitably used for a variety of electronic devices as described above; thus, research and development of light-emitting elements have progressed for higher efficiency or longer element lifetimes. In recent years, phosphorescent light-emitting elements have been actively developed because phosphorescent light-emitting elements achieve higher emission efficiency than fluorescent light-emitting elements (e.g., Patent Document 1).

The lifetime and properties of a light-emitting element including an organic compound are greatly affected by the properties of a host material or an electron-transport material in some cases. Thus, organic compounds having a variety of molecular structures have been proposed as host materials and electron-transport materials (e.g., Patent Documents 2 and 3).

REFERENCE

Patent Document

[Patent Document 1] Japanese Published Patent Application No. 2010-182699

[Patent Document 2] Japanese Published Patent Application No. 2014-209611

[Patent Document 3] Japanese Published Patent Application No. 2015-157808

DISCLOSURE OF INVENTION

Along with the demand for higher performance of electronic devices and lighting devices, a variety of properties are desired for light-emitting elements; development of light-emitting elements with high reliability is especially demanded. Since the characteristics of host materials affect the reliability of light-emitting elements, development of highly reliable host materials has been actively conducted. In particular, development of host materials that can be used in phosphorescent elements and that enables light-emitting elements to have high emission efficiency and high reliability is a matter of urgent necessity.

In view of the above, an object of one embodiment of the present invention is to provide a novel organic compound. In particular, an object is to provide a novel heteroaromatic ring compound. Another object of one embodiment of the present invention is to provide a novel organic compound having an electron-transport property. Another object of one embodiment of the present invention is to provide a light-emitting element with a long lifetime. Another object of one embodiment of the present invention is to provide a light-emitting element with high emission efficiency. Another object of one embodiment of the present invention is to provide a light-emitting element with low driving voltage.

Another object of one embodiment of the present invention is to provide a light-emitting element, a light-emitting device, and an electronic device each having high reliability. Another object of one embodiment of the present invention is to provide a light-emitting element, a light-emitting device, and an electronic device each having low power consumption.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is an organic compound represented by General Formula (G0) below.

[Chemical Formula 1]

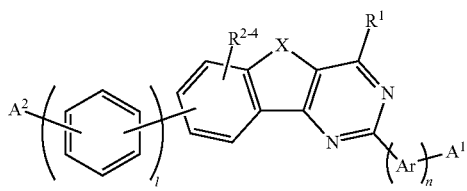

(G0)

In General Formula (G0), X represents oxygen or sulfur, each of $A^1$ and $A^2$ independently represents a substituted or unsubstituted aromatic hydrocarbon group having 6 to 30 carbon atoms or a substituted or unsubstituted heteroaromatic hydrocarbon group having 3 to 30 carbon atoms, Ar represents a substituted or unsubstituted arylene group having 6 to 25 carbon atoms, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, and l is an integer of 1 to 4.

Another embodiment of the present invention is an organic compound represented by General Formula (G1) below.

[Chemical Formula 2]

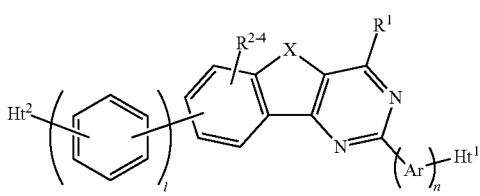

(G1)

In General Formula (G1), X represents oxygen or sulfur, Ar represents a substituted or unsubstituted arylene group having 6 to 25 carbon atoms, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, l is an integer of 1 to 4, and each of $Ht^1$ and $Ht^2$ independently represents a substituted or unsubstituted fused heteroaromatic ring. The fused heteroaromatic ring includes one or more of a carbazole skeleton, a dibenzofuran skeleton, and a dibenzothiophene skeleton, and has 12 to 30 carbon atoms.

Another embodiment of the present invention is an organic compound represented by General Formula (G2) below.

[Chemical Formula 3]

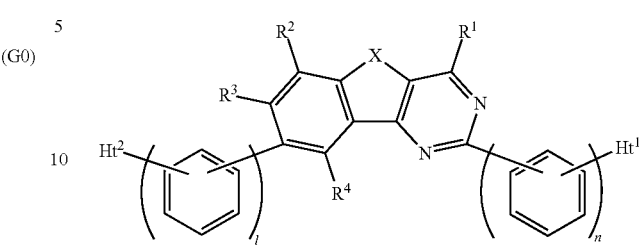

(G2)

In General Formula (G2), X represents oxygen or sulfur, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, l is an integer of 1 to 4, and each of $Ht^1$ and $Ht^2$ independently represents a substituted or unsubstituted fused heteroaromatic ring. The fused heteroaromatic ring includes one or more of a carbazole skeleton, a dibenzofuran skeleton, and a dibenzothiophene skeleton, and has 12 to 30 carbon atoms.

Another embodiment of the present invention is an organic compound represented by General Formula (G3) below.

[Chemical Formula 4]

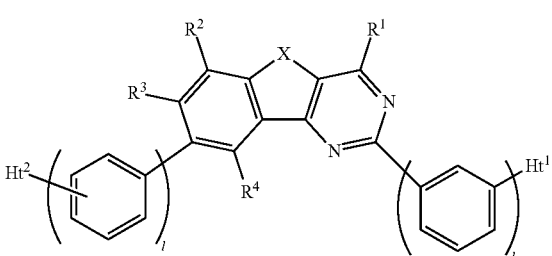

(G3)

In General Formula (G3), X represents oxygen or sulfur, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, l is an integer of 1 to 4, and each of $Ht^1$ and $Ht^2$ independently represents a substituted or unsubstituted fused heteroaromatic ring. The fused heteroaromatic ring includes one or more of a carbazole skeleton, a dibenzofuran skeleton, and a dibenzothiophene skeleton, and has 12 to 30 carbon atoms.

In the above structure, it is preferable that each of $Ht^1$ and $Ht^2$ independently represents any of groups represented by General Formulae (Ht-1) to (Ht-4) below.

[Chemical Formulae 5]

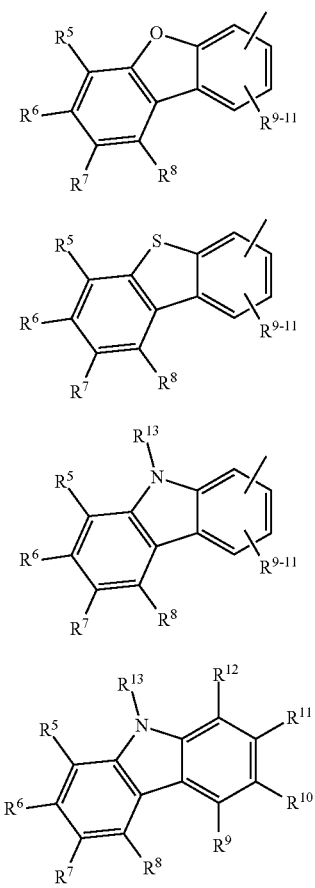

In General Formulae (Ht-1) to (Ht-4), each of $R^5$ to $R^{13}$ independently represents hydrogen, an alkyl group having 1 to 6 carbon atoms, a substituted or unsubstituted cycloalkyl group having 3 to 7 carbon atoms, a substituted or unsubstituted aryl group having 6 to 25 carbon atoms, or a substituted or unsubstituted heteroaromatic hydrocarbon group having 12 to 30 carbon atoms. Note that $R^5$ to $R^8$ and $R^9$ to $R^{12}$ may be bonded to each other to form a saturated ring or an unsaturated ring.

Another embodiment of the present invention is an organic compound represented by General Formula (G4) below.

[Chemical Formula 6]

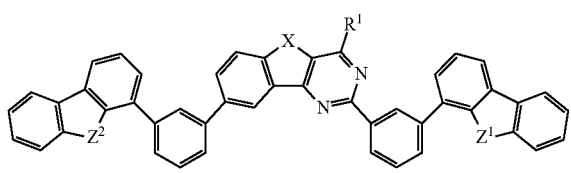

In General Formula (G4), each of X, $Z^1$, and $Z^2$ independently represents oxygen or sulfur, and $R^1$ represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

Another embodiment of the present invention is an organic compound represented by Structural Formula (100) below.

[Chemical Formula 7]

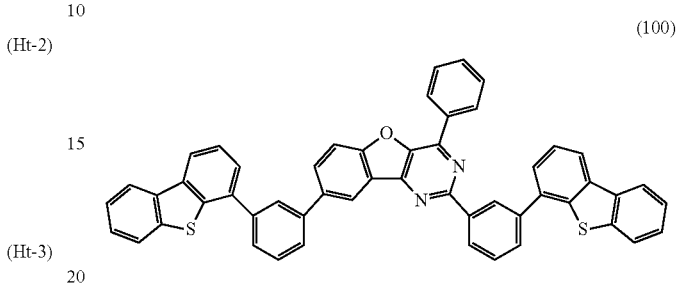

Another embodiment of the present invention is a light-emitting element containing any of the above-described organic compounds.

The light-emitting element having the above structure includes an EL layer between an anode and a cathode. The EL layer preferably includes at least a light-emitting layer. In addition, the EL layer may include a hole-injection layer, a hole-transport layer, an electron-transport layer, an electron-injection layer, and other functional layers.

Another embodiment of the present invention is a display device including the light-emitting element having any of the above structures, and at least one of a color filter and a transistor. Another embodiment of the present invention is an electronic device including the display device, and at least one of a housing and a touch sensor. Another embodiment of the present invention is a lighting device including the light-emitting element having any of the above-described structures, and at least one of a housing and a touch sensor. The category of one embodiment of the present invention includes not only a light-emitting device including a light-emitting element but also an electronic device including a light-emitting device. Accordingly, a light-emitting device in this specification refers to an image display device or a light source (including a lighting device). A display module in which a connector such as a flexible printed circuit (FPC) or a tape carrier package (TCP) is connected to a light-emitting element, a display module in which a printed wiring board is provided on the tip of a TCP, and a display module in which an integrated circuit (IC) is directly mounted on a light-emitting element by a chip on glass (COG) method are also embodiments of the present invention.

One embodiment of the present invention can provide a novel organic compound. In particular, a novel heteroaromatic ring compound can be provided. Another embodiment of the present invention can provide a novel organic compound having an electron-transport property. Another embodiment of the present invention can provide a light-emitting element with a long lifetime. Another embodiment of the present invention can provide a light-emitting element with high emission efficiency. Another embodiment of the present invention can provide a light-emitting element with low driving voltage.

Another embodiment of the present invention can provide a light-emitting element, a light-emitting device, and an electronic device each having high reliability. Another embodiment of the present invention can provide a light-emitting element, a light-emitting device, and an electronic device each having low power consumption.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF DRAWINGS

FIGS. 4A and 4B are schematic diagrams of an active matrix light-emitting device of one embodiment of the present invention.

BEST MODE FOR CARRYING OUT THE INVENTION

Figure 1A:
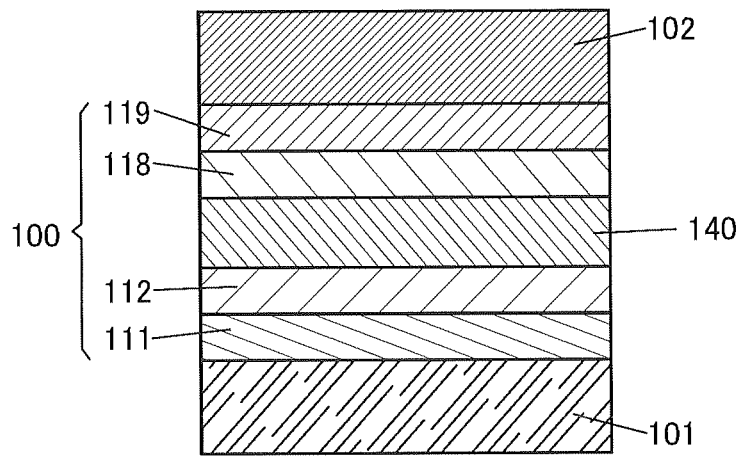
FIGS. 1A and 1B are schematic views of a light-emitting element of one embodiment of the present invention.

Hereinafter, embodiments of the present invention will be described. Note that it is easily understood by those skilled in the art that modes and details disclosed herein can be modified in various ways without departing from the spirit and scope of the present invention. Therefore, the invention disclosed in this specification should not be interpreted as being limited to the description in the embodiments.

Note that in each drawing described in this specification, the size, the thickness, and the like of components such as an anode, an EL layer, an intermediate layer, and a cathode are exaggerated for clarity in some cases. Therefore, the sizes of the components are not limited to the sizes in the drawings and relative sizes between the components.

Note that the ordinal numbers such as "first", "second", and "third" in this specification and the like are used for convenience and do not denote the order of steps, the positional relation, or the like. Therefore, for example, description can be made even when "first" is replaced with "second" or "third", as appropriate. In addition, the ordinal numbers in this specification and the like are not necessarily the same as those which specify one embodiment of the present invention.

Note that in structures of the present invention described in this specification and the like, the same portions or portions having similar functions are denoted by common reference numerals in different drawings, and descriptions thereof are not repeated. Further, the same hatching pattern is applied to portions having similar functions, and the portions are not especially denoted by reference numerals in some cases.

Note that the terms "film" and "layer" can be interchanged depending on the case or circumstances. For example, the term "conductive layer" can be changed into the term "conductive film" in some cases. Also, the term "insulating film" can be changed into the term "insulating layer" in some cases.

Embodiment 1

In this embodiment, an organic compound of one embodiment of the present invention will be described.

An organic compound of one embodiment of the present invention, which can be used for a light-emitting element, is represented by General Formula (G0) below.

[Chemical Formula 8]

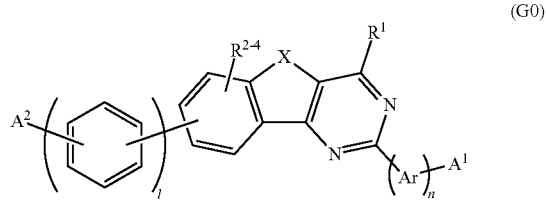

(G0)

In General Formula (G0), X represents oxygen or sulfur, each of $A^1$ and $A^2$ independently represents a substituted or unsubstituted aromatic hydrocarbon group having 6 to 30 carbon atoms or a substituted or unsubstituted heteroaromatic hydrocarbon group having 3 to 30 carbon atoms, Ar represents a substituted or unsubstituted arylene group having 6 to 25 carbon atoms, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, and l is an integer of 1 to 4.

The organic compound of one embodiment of the present invention includes a benzofuro[3,2-d]pyrimidine skeleton or a benzothieno[3,2-d]pyrimidine skeleton. The 2-position of the skeleton has a substituent and the benzene ring side (the 6- to 9-positions) of the skeleton has at least one substituent. Any one of the substituents bonded to the 6- to 9-positions is bonded to the benzofuro[3,2-d]pyrimidine or benzothieno [3,2-d]pyrimidine skeleton via a phenylene group. The present inventors have found that this structure enables a high triplet excitation energy level (T1 level) and a high lowest unoccupied molecular orbital (LUMO) level. The use of the organic compound of one embodiment of the present invention as a host material thus allows efficient utilization of exciplex-triplet energy transfer (ExTET), which is described later. Accordingly, it is possible to provide a light-emitting element with high emission efficiency, a low driving voltage, and high reliability. In addition, a light-emitting element using the organic compound of one embodiment of the present invention can have higher reliability than a light-emitting element using an organic compound in which only the pyrimidine ring side (the 2-position and/or the 4-position) of the benzofuro[3,2-d]pyrimidine skeleton or benzothieno[3,2-d]pyrimidine skeleton has a substituent(s). This effect probably results from increased film quality due to the structure in which the pyrimidine ring side (the 2-position and/or the 4-position) and the benzene ring side (the 6- to 9-positions) of the benzofuro[3,2-d]pyrimidine skeleton or benzothieno[3,2-d]pyrimidine skeleton each have at least one substituent.

The present inventors have also found that an organic compound which includes a benzofuro[3,2-d]pyrimidine skeleton or a benzothieno[3,2-d]pyrimidine skeleton as a benzofuropyrimidine skeleton or a benzothienopyrimidine skeleton can have a higher LUMO level and a higher T1 level than an organic compound which includes a skeleton with other fusion positions. As a result, ExTET can be efficiently utilized, as described above. Accordingly, it is possible to provide a light-emitting element with high emission efficiency, a low driving voltage, and high reliability.

Furthermore, by including a benzofuro[3,2-d]pyrimidine skeleton or a benzothieno[3,2-d]pyrimidine skeleton with a favorable electron-transport property, the organic compound of one embodiment of the present invention has a favorable electron-transport property as well as the above-mentioned high LUMO level. It is thus possible to select a material having a lower LUMO level than the organic compound of one embodiment of the present invention for an electron-transport layer, with the organic compound of one embodiment of the present invention used in a light-emitting layer. With this structure, an electron injection barrier can be formed between the light-emitting layer and the electron-transport layer and carrier balance in an EL layer can be adjusted. Accordingly, a light-emitting element with high emission efficiency can be obtained. Note that the light-emitting element can be driven at a low voltage regardless of the electron injection barrier owing to the favorable electron-transport property of the organic compound of one embodiment of the present invention.

Since the organic compound of one embodiment of the present invention has a high T1 level as described above, the organic compound can be suitably used as a host material of a light-emitting element, particularly a phosphorescent light-emitting element, in which case the light-emitting element can have high emission efficiency and high reliability. Note that the organic compound of one embodiment of the present invention can be used for a fluorescent light-emitting element or a light-emitting element that uses a thermally activated delayed fluorescence material as a guest material.

It is preferable that in General Formula (G0), each of $A^1$ and $A^2$ independently represents a substituted or unsubstituted aromatic hydrocarbon group having 6 to 30 carbon atoms or a substituted or unsubstituted heteroaromatic hydrocarbon group having 3 to 30 carbon atoms. This structure allows the π conjugated systems to spread across a molecule, which leads to high reliability and low driving voltage of a light-emitting element. Furthermore, the aromatic hydrocarbon group and the heteroaromatic ring preferably include a fused ring, i.e., each of $A^1$ and $A^2$ preferably includes a fused ring. This structure contributes to an increase in electrochemical stability and film quality, whereby a light-emitting element with increased reliability can be obtained. Moreover, the molecular weight can be increased without decreasing a sublimation property, so that a material with high heat resistance can be provided.

As examples of the above substituted or unsubstituted aromatic hydrocarbon group having 6 to 30 carbon atoms, substituents including a benzene ring, a naphthalene ring, a fluorene ring, a spirofluorene ring, a phenanthrene ring, or a triphenylene ring can be given. As examples of the substituted or unsubstituted heteroaromatic hydrocarbon group having 3 to 30 carbon atoms, substituents including a pyrrole ring, a pyridine ring, a diazine ring, a triazine ring, an imidazole ring, a triazole ring, a thiophene ring, or a furan ring can be given.

As examples of the above fused ring, fused rings without a heteroatom such as a naphthalene ring, a fluorene ring, a phenanthrene ring, a triphenylene ring, and a spirofluorene ring can be given. When the fused ring without a heteroatom is introduced into A and/or $A^2$ in General Formula (G0), the molecular weight can be easily increased and the organic compound can have high heat resistance. When the fused ring without a heteroatom is introduced into each of $A^1$ and $A^2$ in General Formula (G0), the organic compound can have a lowered highest occupied molecular orbital (HOMO) level. By using the organic compound with a low HOMO level as a host material of a light-emitting element, the light-emitting element can have a lowered hole injection barrier.

The above fused ring may include a heteroatom. As examples of a fused ring including a heteroatom (a fused heteroaromatic ring), fused heteroaromatic rings including a carbazole ring, a dibenzofuran ring, or a dibenzothiophene ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring) can be given. A π-electron rich fused heteroaromatic ring such as a carbazole ring, a dibenzofuran ring, or a dibenzothiophene ring is particularly preferable. When the π-electron rich fused heteroaromatic ring is used, an organic compound with a favorable hole-transport property can be obtained. In addition, when the n-electron rich fused heteroaromatic ring is introduced into the benzofuro[3,2-d]pyrimidine skeleton or benzothieno[3,2-d]pyrimidine skeleton with a favorable electron-transport property, both oxidation characteristics and reduction characteristics can be high and thus, a highly reliable light-emitting element can be obtained.

In General Formula (G0), $A^2$ is preferably bonded to the benzofuro[3,2-d]pyrimidine skeleton or benzothieno[3,2-d]pyrimidine skeleton via one or more phenylene groups. The organic compound with this structure, in which the distance between the benzofuro[3,2-d]pyrimidine skeleton or benzothieno[3,2-d]pyrimidine skeleton and $A^2$ is large, can have a higher T1 level than an organic compound in which $A^2$ is directly bonded to the benzofuro[3,2-d]pyrimidine skeleton or benzothieno[3,2-d]pyrimidine skeleton. As described above, one feature of the organic compound of one embodiment of the present invention is that $A^2$ is bonded to the benzofuro[3,2-d]pyrimidine skeleton or benzothieno[3,2-d]pyrimidine skeleton via one or more phenylene groups.

Furthermore, $A^2$ and the benzofuro[3,2-d]pyrimidine skeleton or benzothieno[3,2-d]pyrimidine skeleton are preferably bonded to each other via the phenylene group at the meta-position. Owing to the bonding at the meta-position, the conjugated system of the benzofuro[3,2-d]pyrimidine skeleton or benzothieno[3,2-d]pyrimidine skeleton and that of $A^2$ are independent of each other (i.e., the conjugated system between the benzofuro[3,2-d]pyrimidine skeleton or benzothieno[3,2-d]pyrimidine skeleton and $A^2$ is cut); thus, an organic compound with a high T1 level can be obtained.

In General Formula (G0), $A^1$ is preferably bonded to the benzofuro[3,2-d]pyrimidine skeleton or benzothieno[3,2-d]pyrimidine skeleton via one or more arylene groups. The organic compound with this structure, in which the distance between the benzofuro[3,2-d]pyrimidine skeleton or benzothieno[3,2-d]pyrimidine skeleton and $A^1$ is large, can have a higher T1 level than an organic compound in which $A^1$ is directly bonded to the benzofuro[3,2-d]pyrimidine skeleton or benzothieno[3,2-d]pyrimidine skeleton. Note that $A^1$ may be directly bonded to the benzofuro[3,2-d]pyrimidine skeleton or benzothieno[3,2-d]pyrimidine skeleton.

In General Formula (G0), $R^1$ preferably has a hydrocarbon group. Examples of the hydrocarbon group include an alkyl group having 1 to 6 carbon atoms such as a methyl group, an ethyl group, a propyl group, an isopropyl group, a butyl group, an isobutyl group, a tert-butyl group, or an n-hexyl group; a cycloalkyl group having 3 to 7 carbon atoms such as a cyclopropyl group, a cyclobutyl group, a cyclopentyl group, or a cyclohexyl group; and an aryl group having 6 to 25 carbon atoms such as a phenyl group, a naphthyl group, a biphenyl group, a fluorenyl group, or a spirofluorenyl group. When the hydrocarbon group is introduced into $R^1$, i.e., when a substituent is introduced near the N atom in the benzofuro[3,2-d]pyrimidine skeleton or benzothieno[3,2-d]pyrimidine skeleton, the structure near the N atom can be steric and a light-emitting element with high reliability can be obtained.

One embodiment of the present invention is an organic compound represented by General Formula (G1).

[Chemical Formula 9]

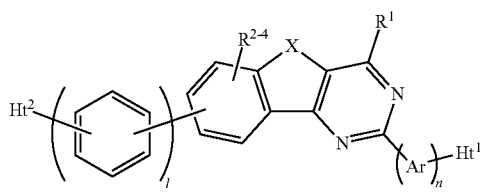

(G1)

In General Formula (G1), X represents oxygen or sulfur, Ar represents a substituted or unsubstituted arylene group having 6 to 25 carbon atoms, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, l is an integer of 1 to 4, and each of $Ht^1$ and $Ht^2$ independently represents a substituted or unsubstituted fused heteroaromatic ring. The fused heteroaromatic ring includes one or more of a carbazole skeleton, a dibenzofuran skeleton, and a dibenzothiophene skeleton, and has 12 to 30 carbon atoms.

In General Formula (G1), $Ht^2$ is preferably bonded to the benzofuro[3,2-d]pyrimidine skeleton or benzothieno[3,2-d]pyrimidine skeleton via one or more phenylene groups. The organic compound with this structure can have a higher T1 level than an organic compound in which $Ht^2$ is directly bonded to the benzofuro[3,2-d]pyrimidine skeleton or benzothieno[3,2-d]pyrimidine skeleton.

Furthermore, $Ht^2$ and the benzofuro[3,2-d]pyrimidine skeleton or benzothieno[3,2-d]pyrimidine skeleton are preferably bonded to each other via the phenylene group at the meta-position. Owing to the bonding at the meta-position, the conjugated system of the benzofuro[3,2-d]pyrimidine skeleton or benzothieno[3,2-d]pyrimidine skeleton and that of $Ht^2$ are independent of each other (i.e., the conjugated system between the benzofuro[3,2-d]pyrimidine skeleton or benzothieno[3,2-d]pyrimidine skeleton and $Ht^2$ is cut); thus, an organic compound with a high T1 level can be obtained.

In General Formula (G1), $Ht^1$ is preferably bonded to the benzofuro[3,2-d]pyrimidine skeleton or benzothieno[3,2-d]pyrimidine skeleton via one or more arylene groups. The organic compound with this structure can have a higher T1 level than an organic compound in which $Ht^1$ is directly bonded to the benzofuro[3,2-d]pyrimidine skeleton or benzothieno[3,2-d]pyrimidine skeleton. Note that $Ht^1$ may be bonded to the benzofuro[3,2-d]pyrimidine skeleton or benzothieno[3,2-d]pyrimidine skeleton without an arylene group.

In General Formula (G1), $Ht^1$ and $Ht^2$ preferably include a skeleton having a hole-transport property. When a skeleton having a hole-transport property is introduced into the benzofuro[3,2-d]pyrimidine skeleton or benzothieno[3,2-d]pyrimidine skeleton, both oxidation characteristics and reduction characteristics can be high and a highly reliable light-emitting element can be provided. Furthermore, the carrier (electrons and holes) transport property is improved, so that the light-emitting element can be driven at a low voltage. It is particularly preferable that $Ht^1$ and $Ht^2$ be each a substituted or unsubstituted heteroaromatic hydrocarbon group having 12 to 30 carbon atoms including any one of a carbazole ring, a dibenzofuran ring, and a dibenzothiophene ring. An organic compound with such a structure is stable in an excited state and has high heat resistance and a high T1 level.

One embodiment of the present invention is an organic compound represented by General Formula (G2).

[Chemical Formula 10]

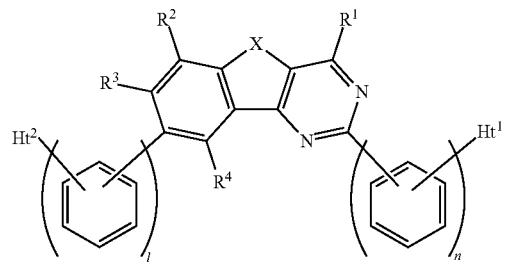

(G2)

In General Formula (G2), X represents oxygen or sulfur, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, l is an integer of 1 to 4, and each of $Ht^1$ and $Ht^2$ independently represents a substituted or unsubstituted fused heteroaromatic ring. The fused heteroaromatic ring includes one or more of a carbazole skeleton, a dibenzofuran skeleton, and a dibenzothiophene skeleton, and has 12 to 30 carbon atoms.

One embodiment of the present invention is an organic compound represented by General Formula (G3).

[Chemical Formula 11]

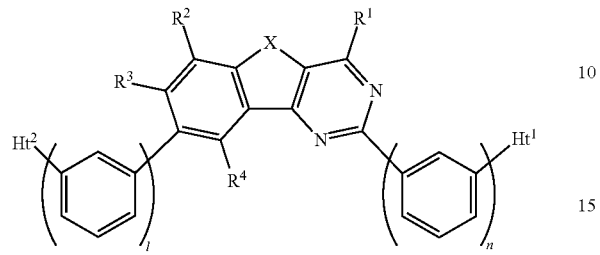

(G3)

In General Formula (G3), X represents oxygen or sulfur, each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, l is an integer of 1 to 4, and each of $Ht^1$ and $Ht^2$ independently represents a substituted or unsubstituted fused heteroaromatic ring. The fused heteroaromatic ring includes one or more of a carbazole skeleton, a dibenzofuran skeleton, and a dibenzothiophene skeleton, and has 12 to 30 carbon atoms.

In the organic compound of one embodiment of the present invention, $Ht^1$, which is the substituent on the pyrimidine ring side, is preferably bonded to the 2-position of the benzofuro[3,2-d]pyrimidine skeleton or benzothieno[3,2-d]pyrimidine skeleton via an arylene group, further preferably via a phenylene group. Furthermore, $Ht^1$ and the benzofuro[3,2-d]pyrimidine skeleton or benzothieno[3,2-d]pyrimidine skeleton are preferably bonded to each other via the phenylene group at the meta-position. The organic compound having this structure can have a high T1 level.

In the organic compound of one embodiment of the present invention, when $Ht^2$, which is the substituent on the benzene ring side, is bonded to the benzofuro[3,2-d]pyrimidine skeleton or benzothieno[3,2-d]pyrimidine skeleton via a phenylene group, the bonding position is preferably the 8-position. Furthermore, $Ht^2$ and the benzofuro[3,2-d]pyrimidine skeleton or benzothieno[3,2-d]pyrimidine skeleton are preferably bonded to each other via the phenylene group at the meta-position. The organic compound having this structure can have a high T1 level.

In addition, it is preferable that each of $Ht^1$ and $Ht^2$ in General Formulae (G1) to (G3) above be independently represented by any of General Formulae (Ht-1) to (Ht-4) below.

[Chemical Formulae 12]

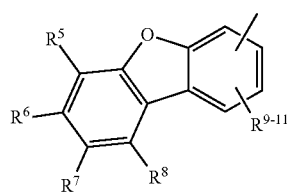

(Ht-1)

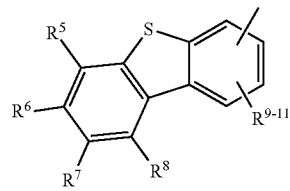

(Ht-2)

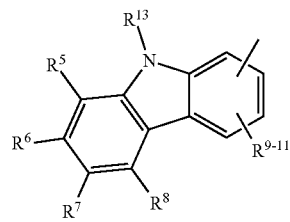

(Ht-3)

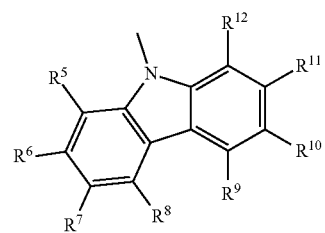

(Ht-4)

In General Formulae (Ht-1) to (Ht-4), each of $R^5$ to $R^{13}$ independently represents hydrogen, an alkyl group having 1 to 6 carbon atoms, a substituted or unsubstituted cycloalkyl group having 3 to 7 carbon atoms, a substituted or unsubstituted aryl group having 6 to 25 carbon atoms, or a substituted or unsubstituted heteroaromatic hydrocarbon group having 12 to 30 carbon atoms. Note that $R^5$ to $R^8$ and $R^9$ to $R^{12}$ may be bonded to each other to form a saturated ring or an unsaturated ring.

As examples of the above heteroaromatic hydrocarbon group having 12 to 30 carbon atoms, substituents with a fused heteroaromatic ring including a carbazole ring, a dibenzofuran ring, or a dibenzothiophene ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring) can be given. A π-electron rich fused heteroaromatic ring such as a carbazole ring, a dibenzofuran ring, or a dibenzothiophene ring is particularly preferable. When the π-electron rich fused heteroaromatic ring is used, an organic compound with a favorable hole-transport property can be obtained.

Examples of the saturated ring include a cyclopropane ring, a cyclobutyl ring, a cyclopentane ring, and a cyclohexane ring. Examples of the unsaturated ring include a furan ring, a thiophene ring, a pyrrole ring, and a benzene ring.

One embodiment of the present invention is an organic compound represented by General Formula (G4).

[Chemical Formula 13]

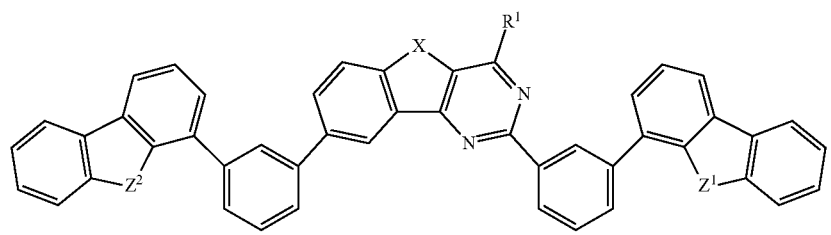

(G4)

In General Formula (G4), each of X, $Z^1$, and $Z^2$ independently represents oxygen or sulfur, and $R^1$ represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

One embodiment of the present invention is an organic compound represented by Structural Formula (100).

[Chemical Formula 14]

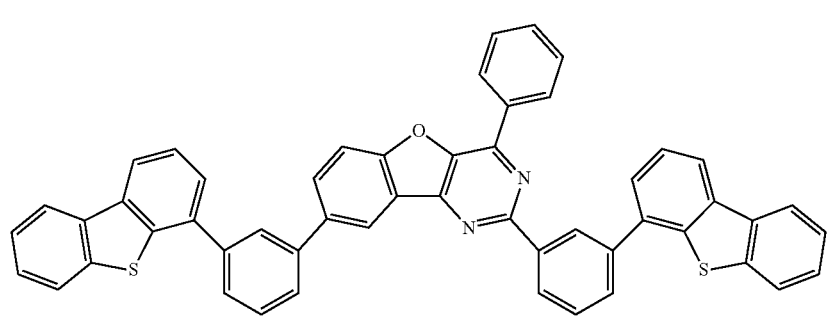

(100)

Examples of Substituents

In General Formulae (G0) and (G1), examples of the substituted or unsubstituted arylene group having 6 to 25 carbon atoms (Ar) include a phenylene group, a naphthylene group, a fluorenediyl group, a biphenyldiyl group, and a spirofluorenediyl group. Specifically, groups represented by Structural Formulae (Ar-1) to (Ar-27) below can be used. Note that the group represented by Ar is not limited thereto and may include a substituent.

[Chemical Formulae 15]

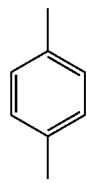

(Ar-1)

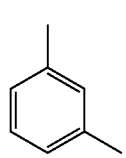

(Ar-2)

-continued

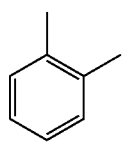

(Ar-3)

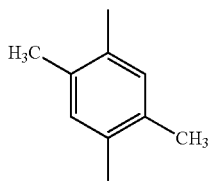

(Ar-4)

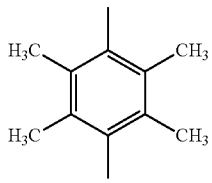

(Ar-5)

(Ar-6)
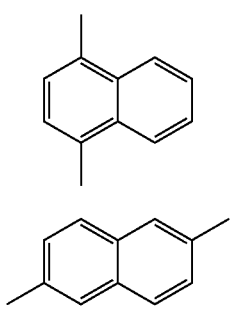
(Ar-7)
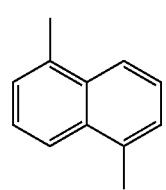
(Ar-8)
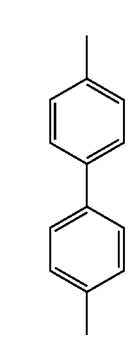
(Ar-9)
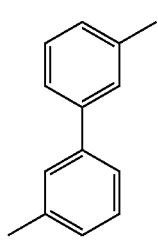
(Ar-10)
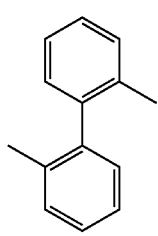
(Ar-11)
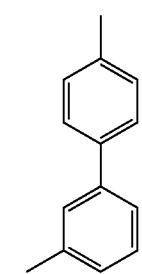
(Ar-12)
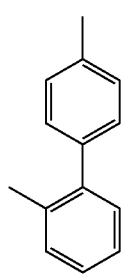
(Ar-13)
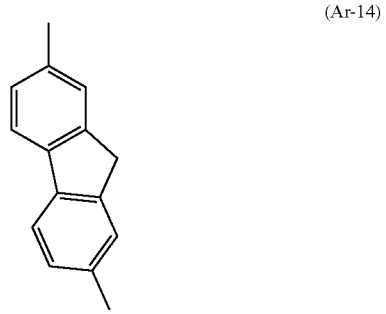
(Ar-14)
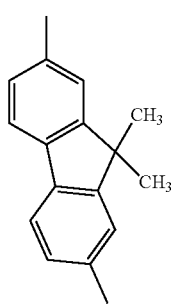
(Ar-15)
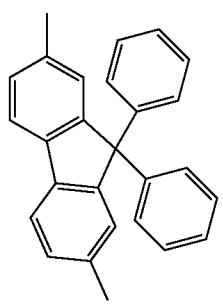
(Ar-16)
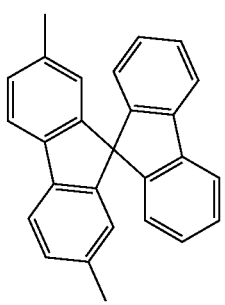
(Ar-17)

-continued
(Ar-18)
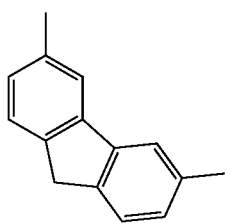
(Ar-19)
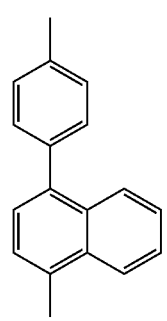
(Ar-20)
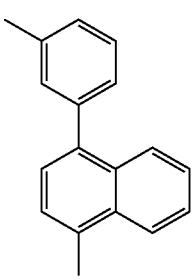
(Ar-21)
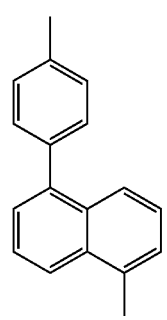
(Ar-22)
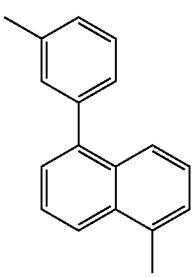
(Ar-23)
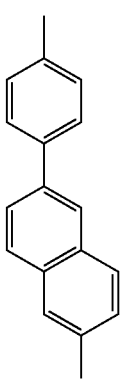
(Ar-24)
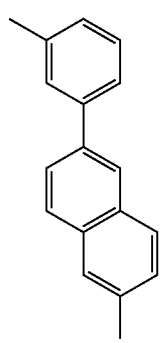
(Ar-25)
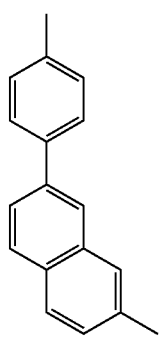
(Ar-26)
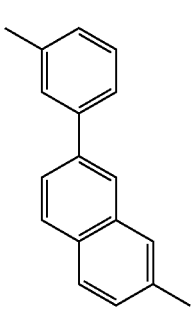

-continued

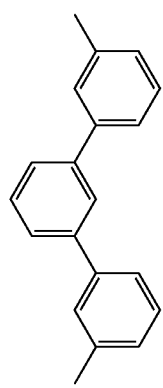
(Ar-27)

Furthermore, each of $R^1$ to $R^4$ in General Formulae (G0) to (G4) and $R^5$ to $R^{13}$ in General Formulae (Ht-1) to (Ht-4) independently represents hydrogen, an alkyl group having 1 to 6 carbon atoms, a substituted or unsubstituted cycloalkyl group having 3 to 7 carbon atoms, a substituted or unsubstituted aryl group having 6 to 25 carbon atoms, or a substituted or unsubstituted heteroaromatic hydrocarbon group having 12 to 30 carbon atoms. Specific examples of the alkyl group include a methyl group, an ethyl group, a propyl group, an isopropyl group, a butyl group, an isobutyl group, a tert-butyl group, and an n-hexyl group. Specific examples of the cycloalkyl group include a cyclopropyl group, a cyclobutyl group, a cyclopentyl group, and a cyclohexyl group. Specific examples of the aryl group include a phenyl group, a naphthyl group, a biphenyl group, a fluorenyl group, and a spirofluorenyl group. As examples of the heteroaromatic hydrocarbon group, substituents with a fused heteroaromatic ring including a carbazole ring, a dibenzofuran ring, or a dibenzothiophene ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring) can be given. More specific examples are groups represented by Structural Formulae (R-1) to (R-55) below. Note that the groups represented by $R^1$ to $R^4$ and $R^5$ to $R^{13}$ are not limited to these.

[Chemical Formulae 16]

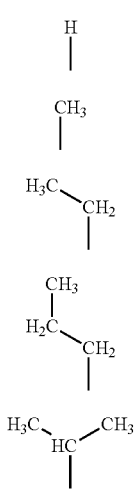

(R-1)
(R-2)
(R-3)
(R-4)
(R-5)

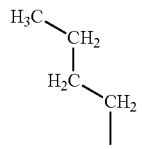
(R-6)

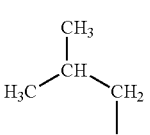
(R-7)

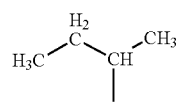
(R-8)

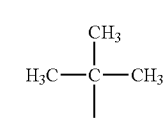
(R-9)

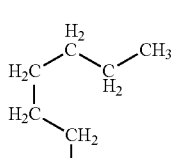
(R-10)

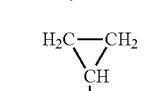
(R-11)

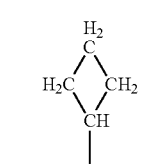
(R-12)

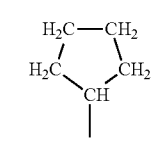
(R-13)

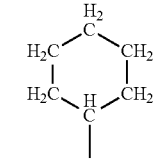
(R-14)

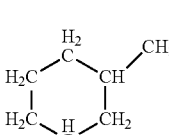
(R-15)

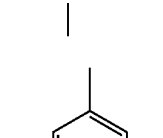
(R-16)

-continued
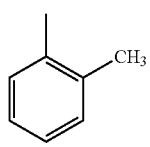 (R-17)
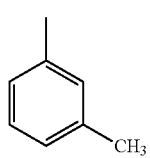 (R-18)
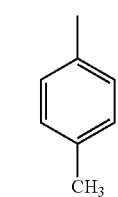 (R-19)
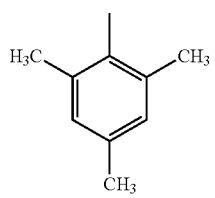 (R-20)
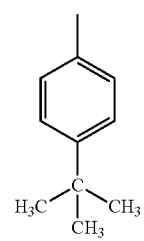 (R-21)
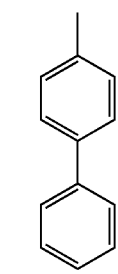 (R-22)
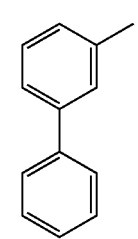 (R-23)
-continued
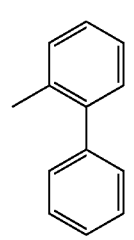 (R-24)
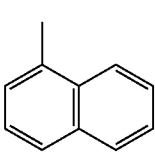 (R-25)
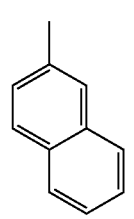 (R-26)
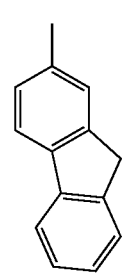 (R-27)
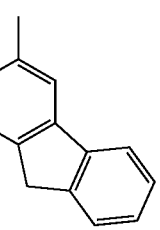 (R-28)
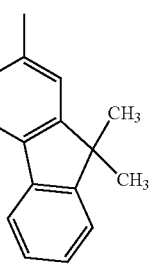 (R-29)
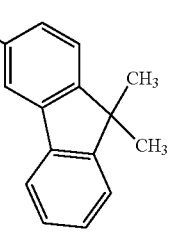 (R-30)

(R-31) 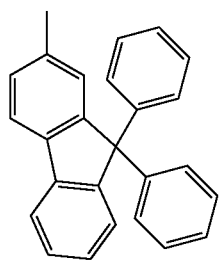
(R-32) 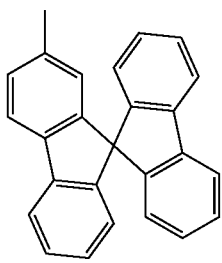
(R-33) 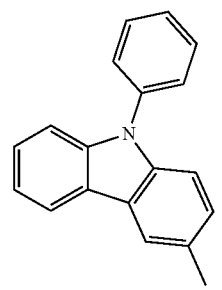
(R-34) 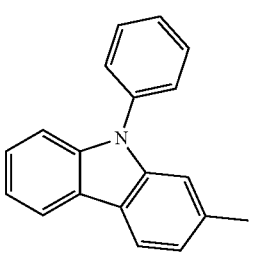
(R-35) 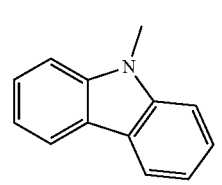
(R-36) 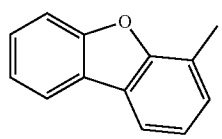
(R-37) 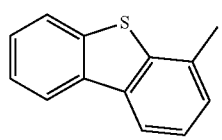
(R-38) 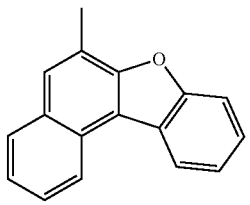
(R-39) 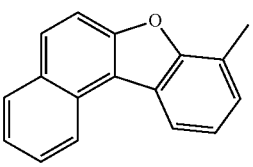
(R-40) 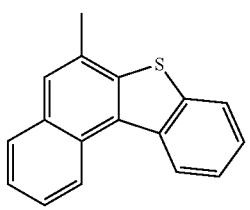
(R-41) 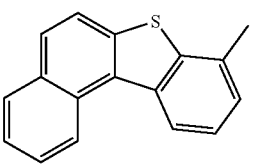
(R-42) 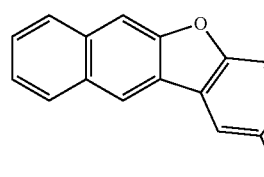
(R-43) 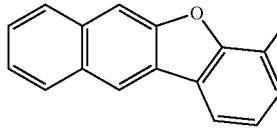
(R-44) 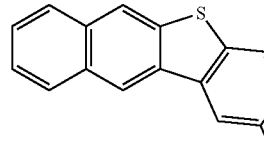
(R-45) 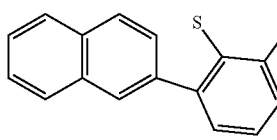

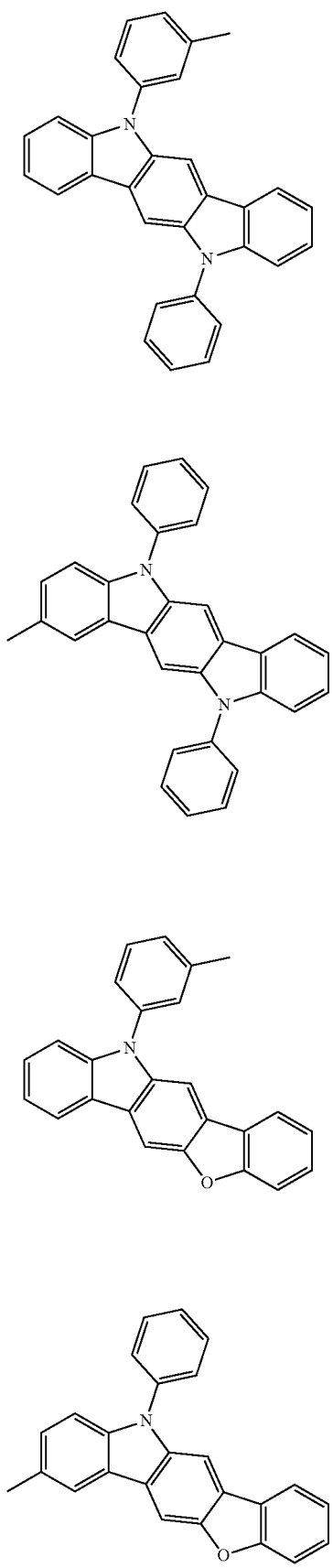
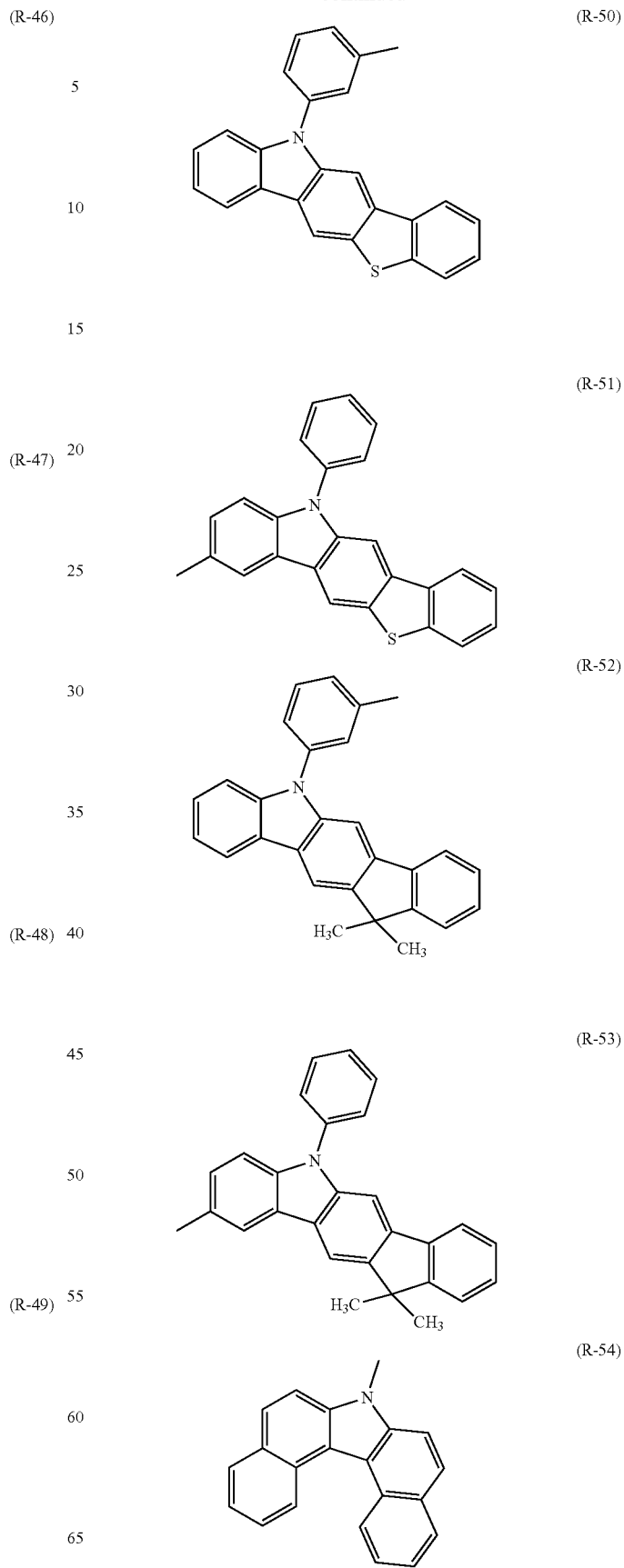

-continued (R-55)

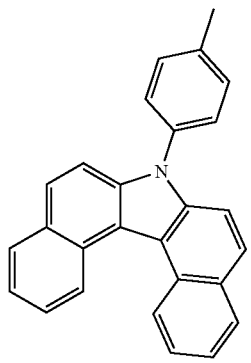

In the case where $A^1$, $A^2$, Ar, $Ht^1$, $Ht^2$, $R^1$ to $R^4$, and $R^6$ to $R^{13}$ in General Formulae (G0) to (G4) and General Formulae (Ht-1) to (Ht-4) above further include a substituent, examples of the substituent include an alkyl group having 1 to 6 carbon atoms, a substituted or unsubstituted cycloalkyl group having 3 to 7 carbon atoms, and a substituted or unsubstituted aryl group having 6 to 25 carbon atoms. Specific examples of the alkyl group include a methyl group, an ethyl group, a propyl group, an isopropyl group, a butyl group, an isobutyl group, a tert-butyl group, and an n-hexyl group. Specific examples of the cycloalkyl group include a cyclopropyl group, a cyclobutyl group, a cyclopentyl group, and a cyclohexyl group. Specific examples of the aryl group include a phenyl group, a naphthyl group, a biphenyl group, a fluorenyl group, and a spirofluorenyl group.

Specific Examples of Compounds

Specific examples of the compounds represented by General Formulae (G0) to (G4) include organic compounds represented by Structural Formulae (100) to (135) below. Note that the organic compounds represented by General Formulae (G0) to (G4) are not limited to the following examples.

[Chemical Formulae 18]

-continued

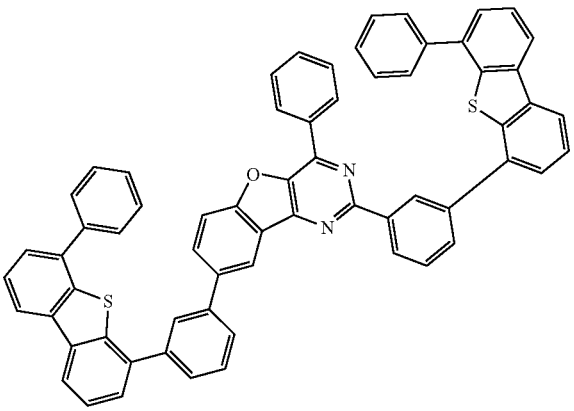

(101)

(102)

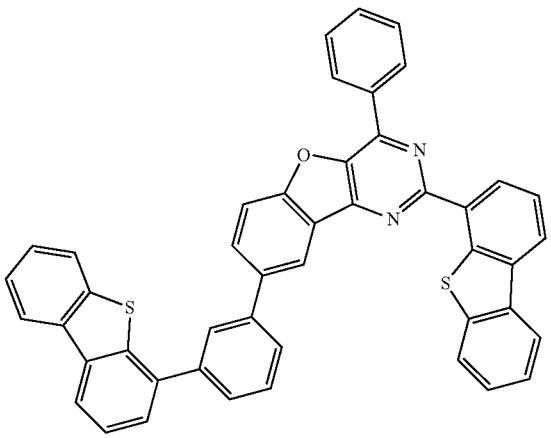

(103)

(100)

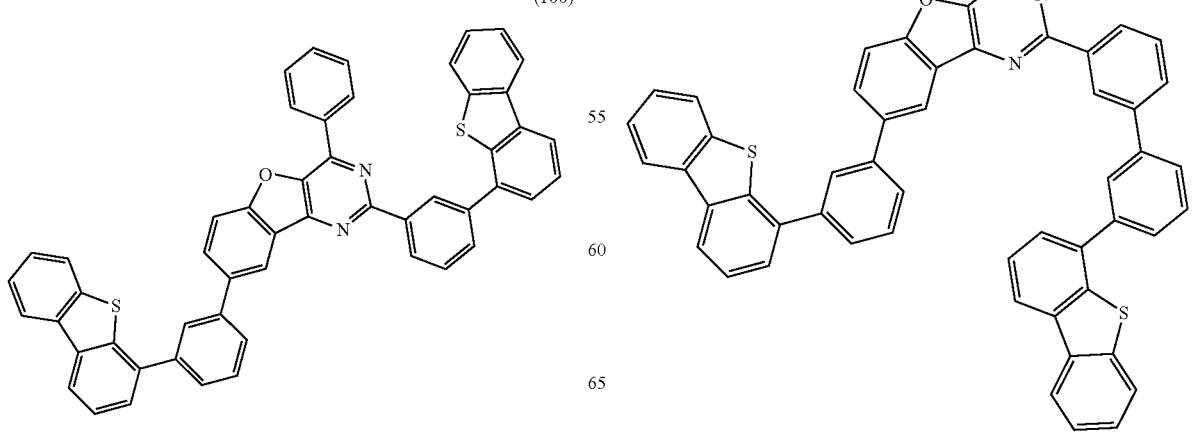

(104)
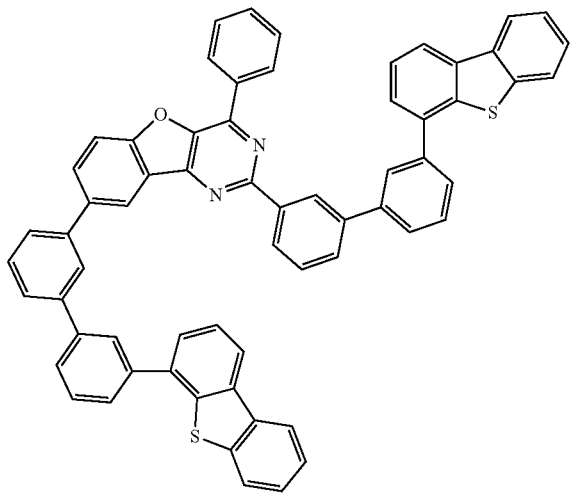
(105)
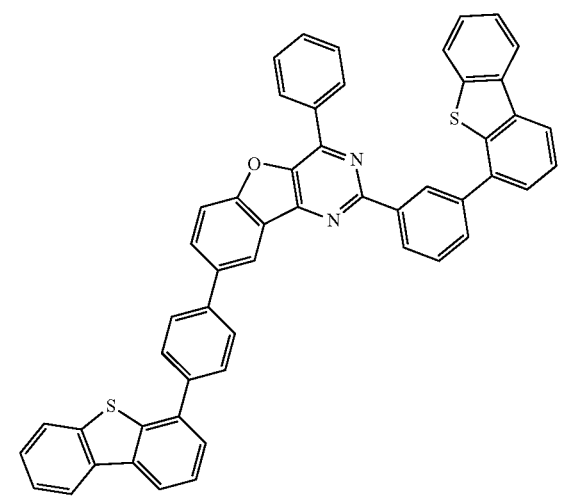
[Chemical Formulae 19]
(106)
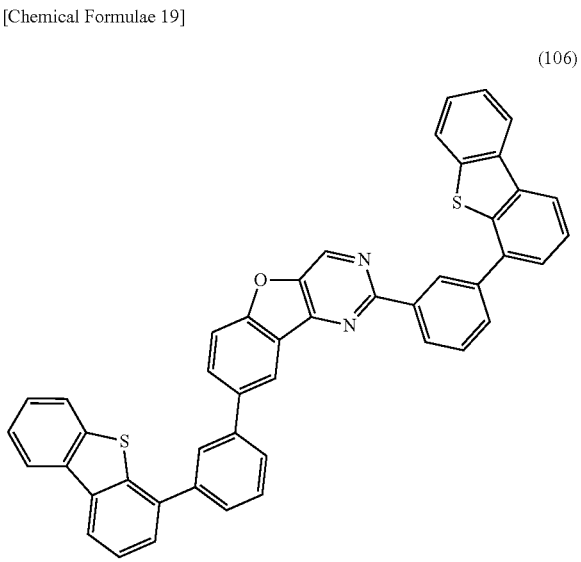
(107)
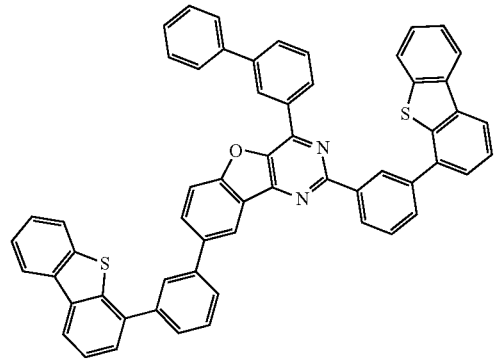
(108)
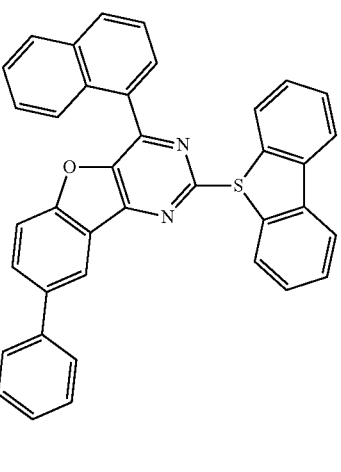
(109)
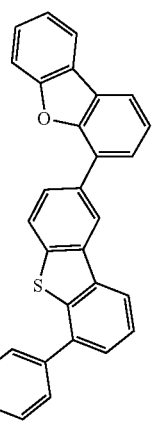

[Chemical Formulae 20]
(110)
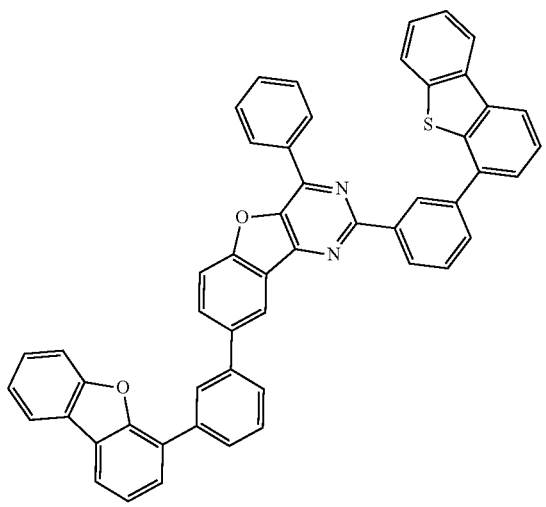
(111)
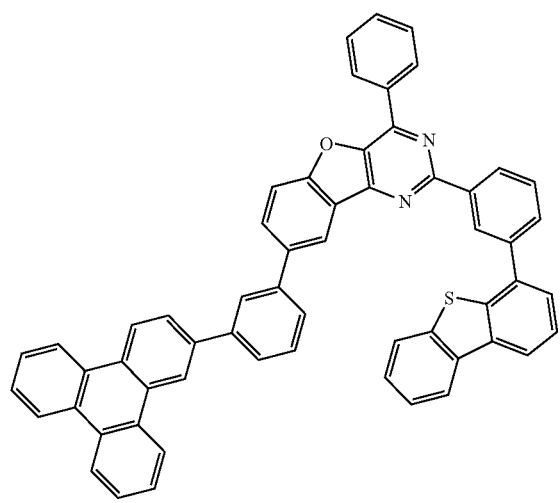
(112)
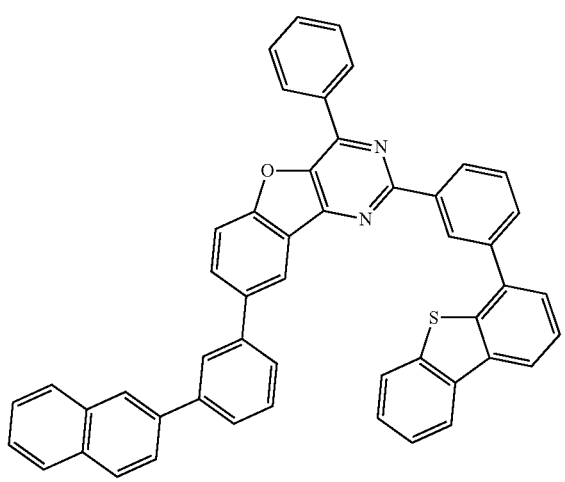
(113)
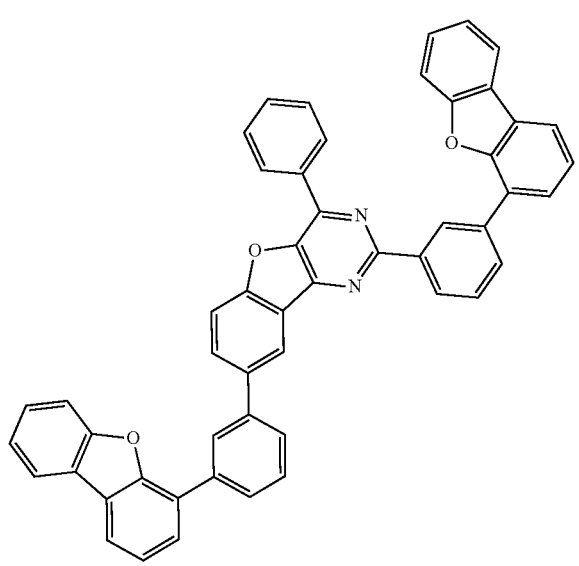
(114)
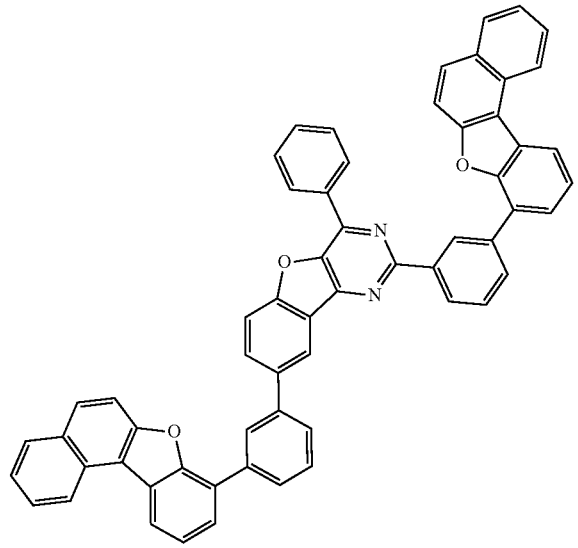
(115)
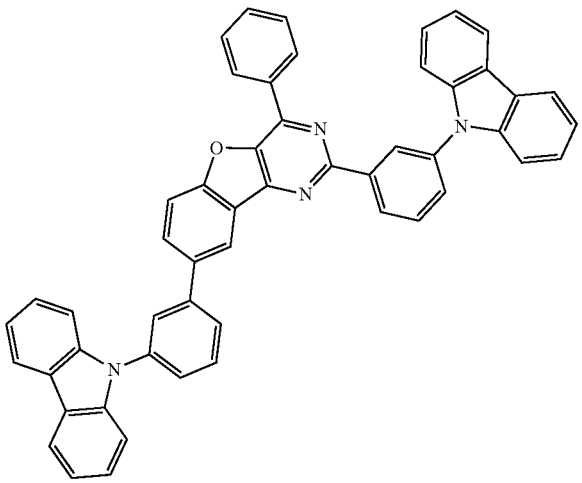

(116)
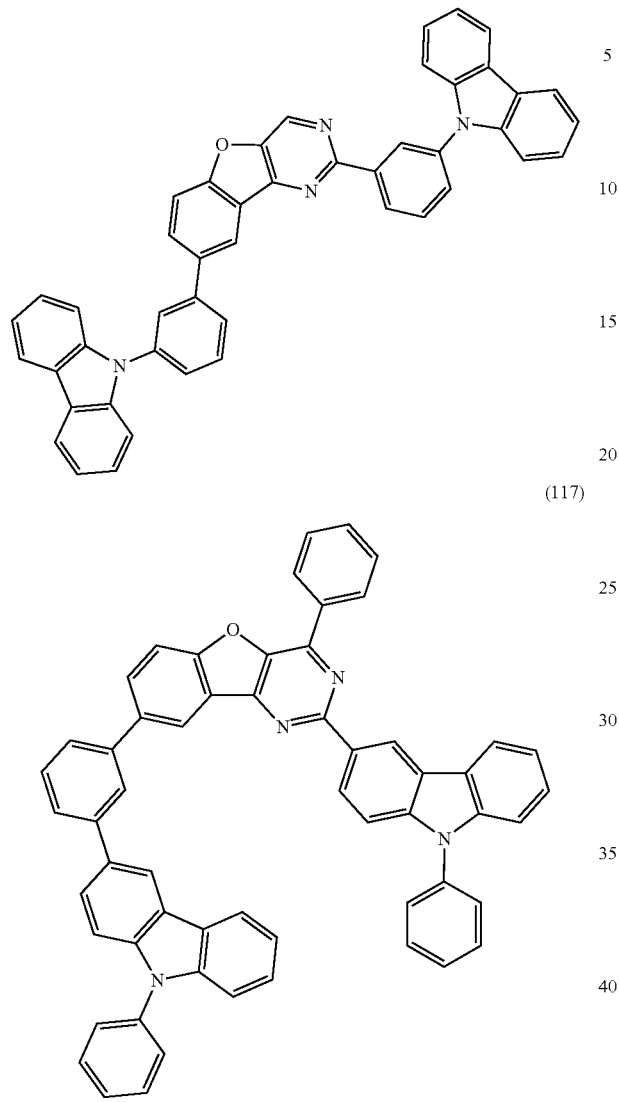
(117)
[Chemical Formulae 21]
(118)
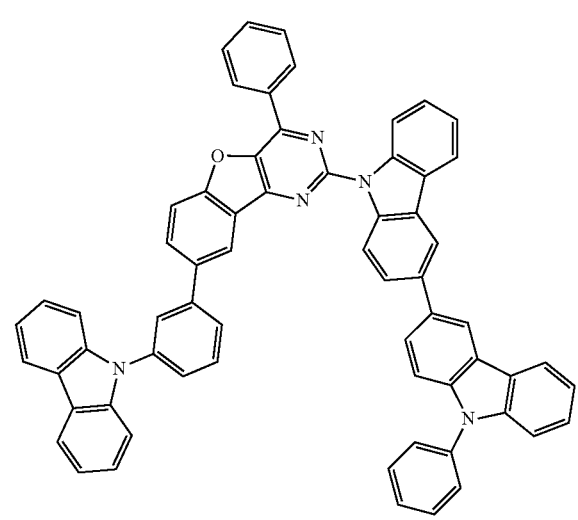
(119)
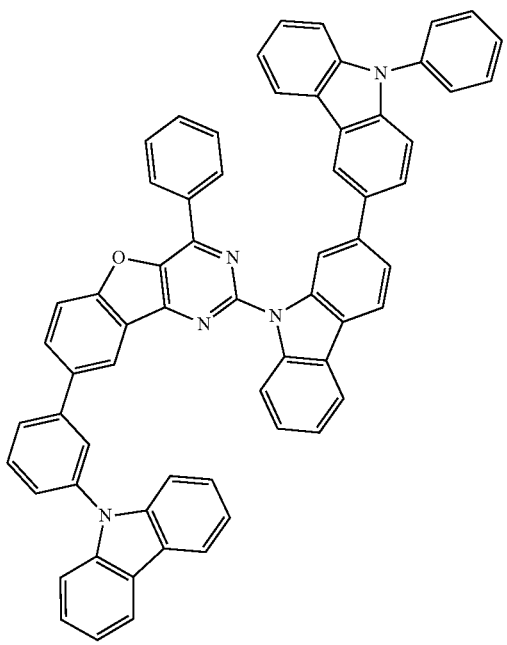
(120)
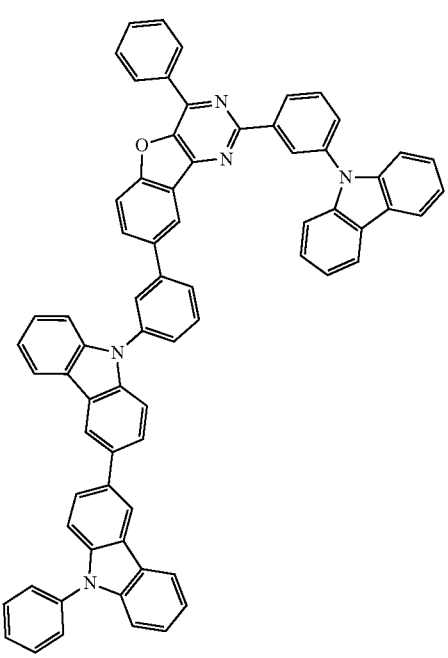

(121)
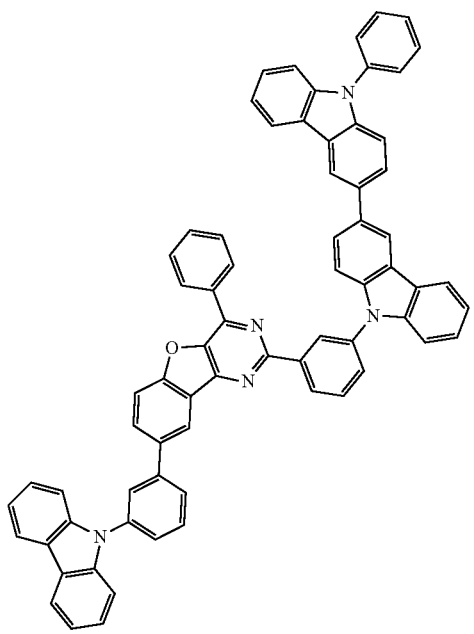
[Chemical Formulae 22]
(122)
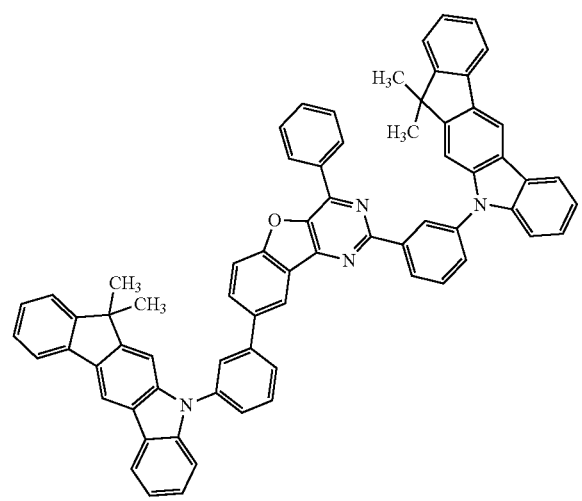
(123)
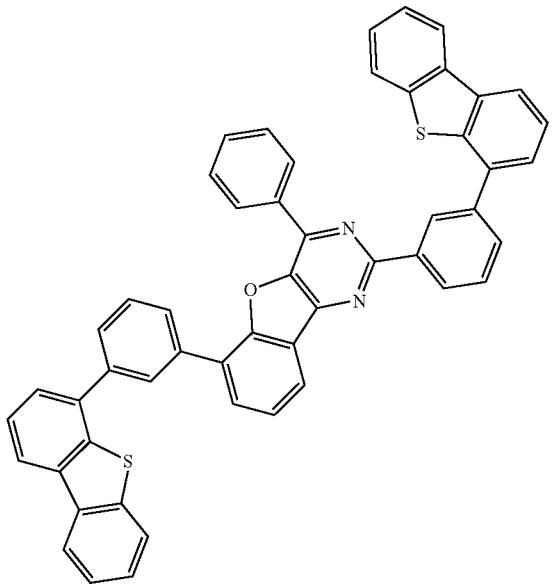
(124)
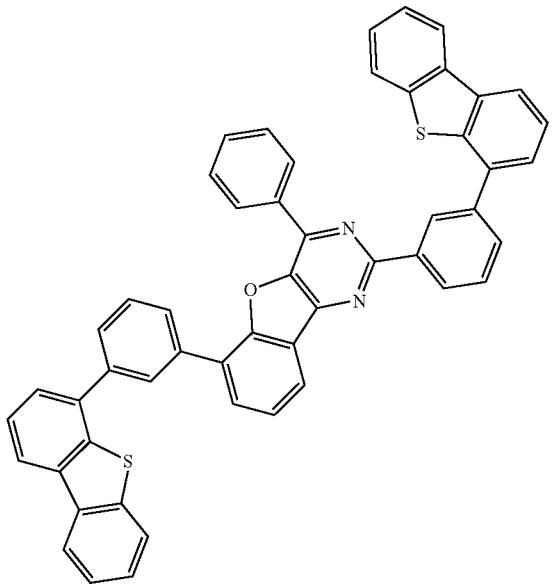
(125)
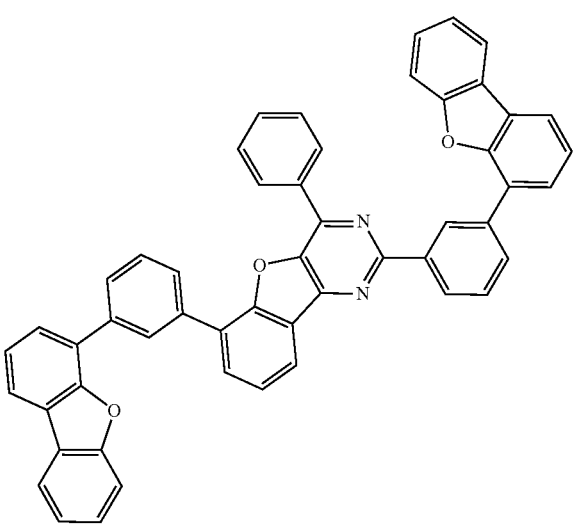

-continued
(126)
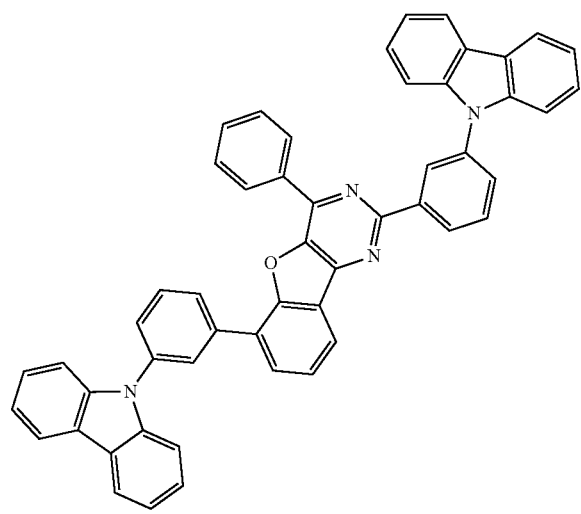
(127)
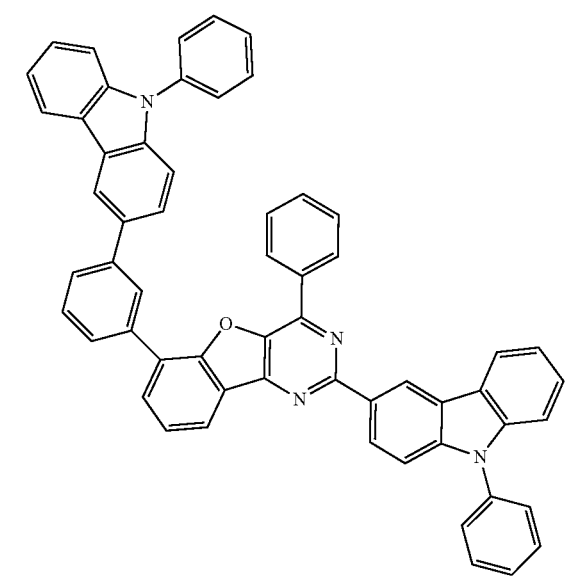
[Chemical Formulae 23]
(128)
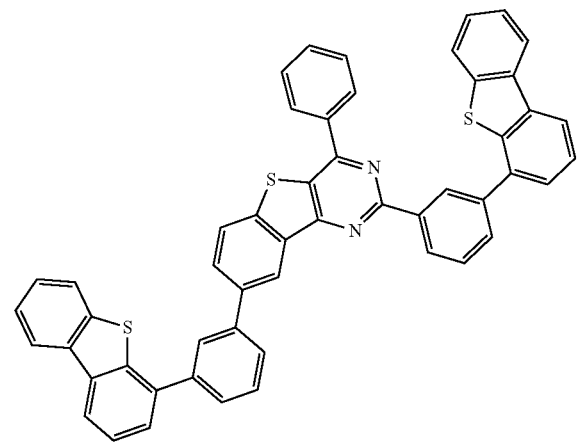
-continued
(129)
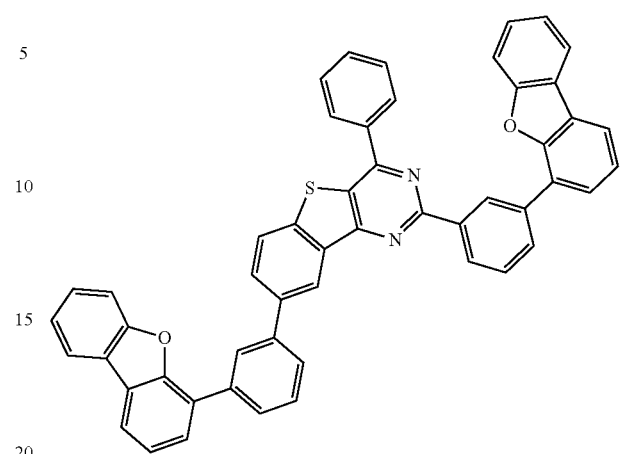
(130)
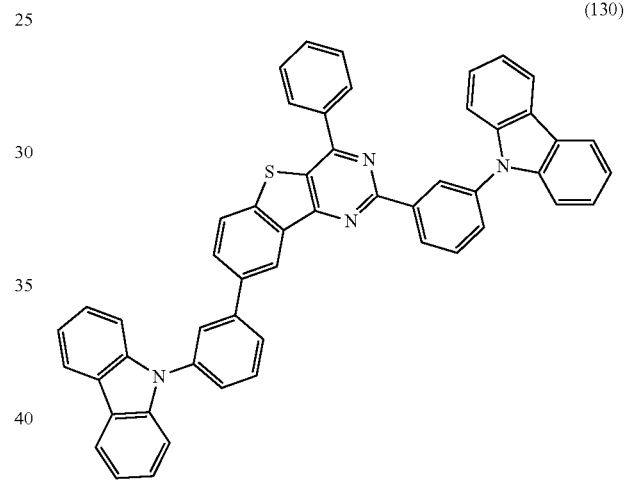
(131)
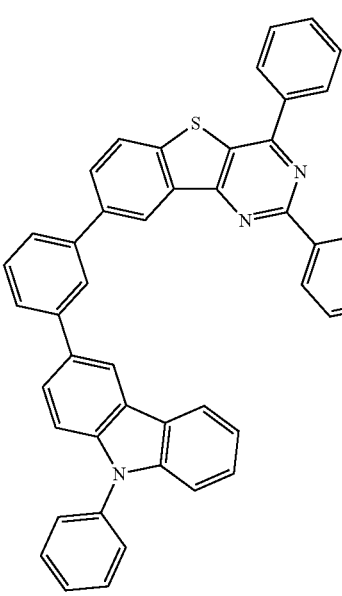

(132)
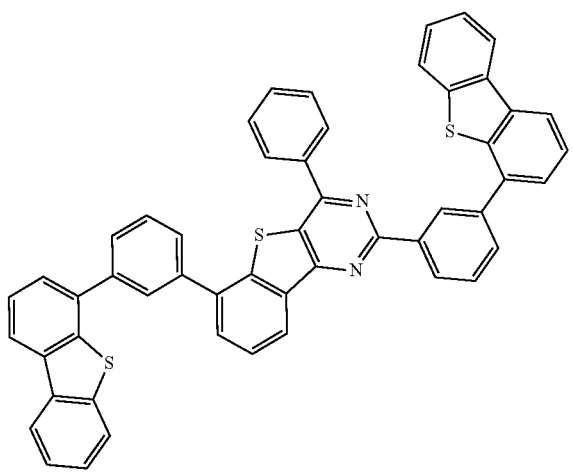
(133)
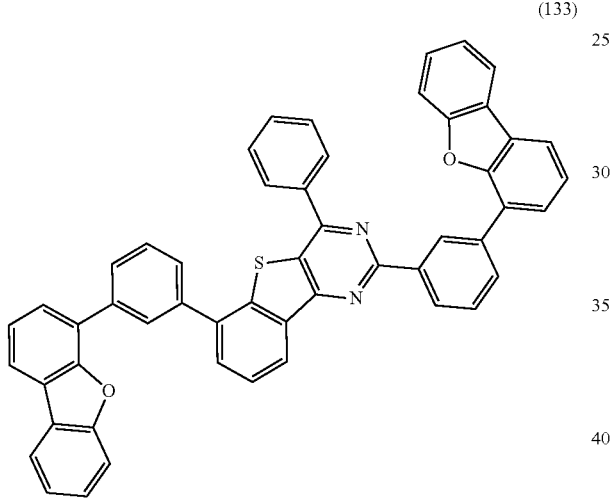
[Chemical Formulae 24]
(134)
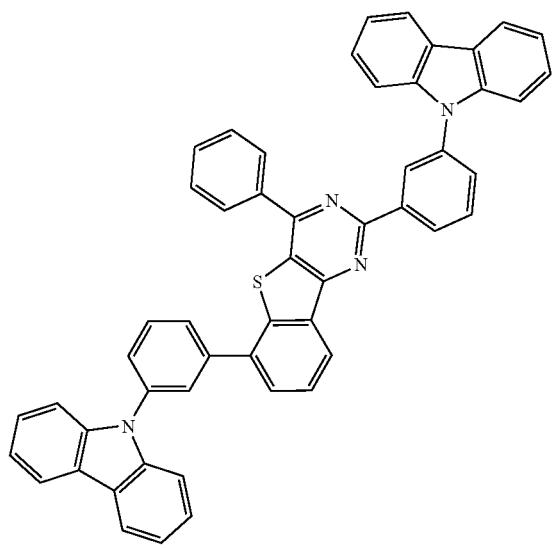
(135)
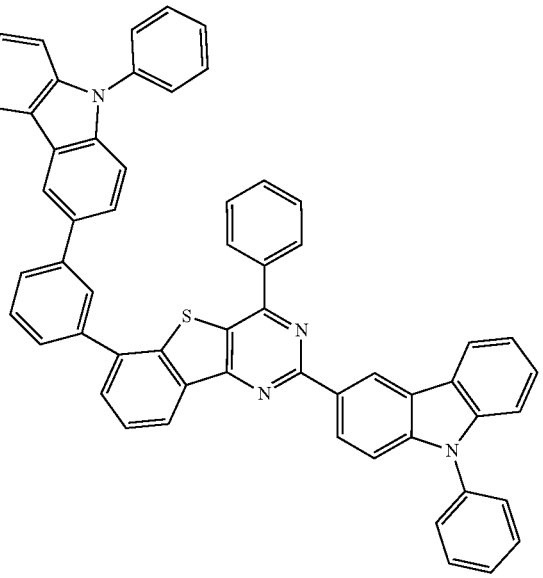
(136)
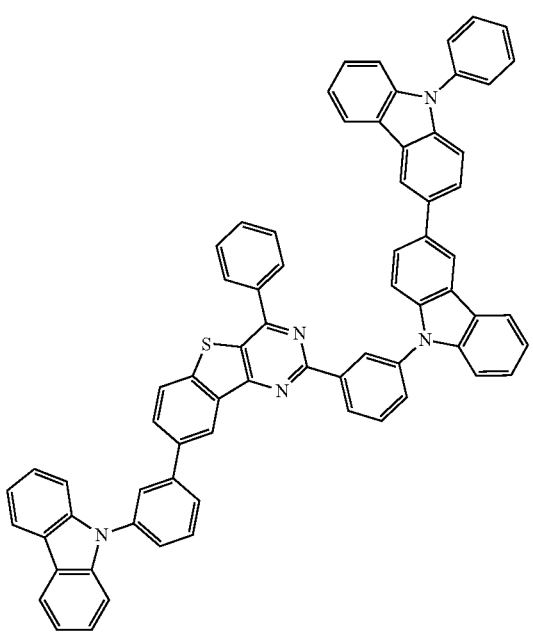

(137)

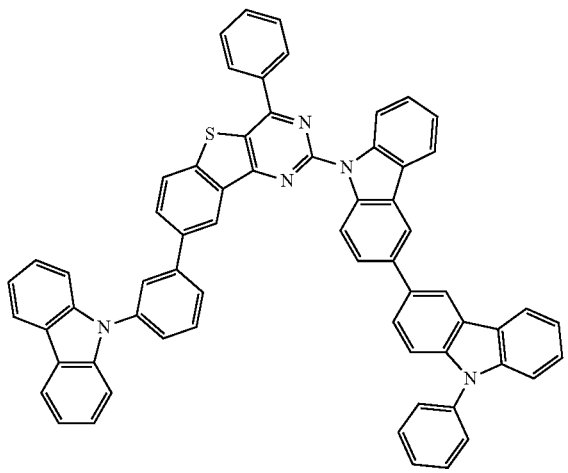

When at least one of $A^1$ and $A^2$ in General Formula (G0) has a hole-transport skeleton, the organic compound of one embodiment of the present invention, which includes the benzofuro[3,2-d]pyrimidine skeleton or benzothieno[3,2-d]pyrimidine skeleton with an electron-transport property, has both a hole-transport skeleton and an electron-transport skeleton; in this case, the organic compound of one embodiment of the present invention can be regarded as a bipolar material. Such a material has a high carrier-transport property and thus a light-emitting element using this material as a host material can be driven at a low voltage.

The organic compound of one embodiment of the present invention includes a π-electron rich heteroaromatic ring (e.g., a dibenzofuran skeleton, a dibenzothiophene skeleton, or a carbazole skeleton) and a π-electron deficient heteroaromatic ring (a benzofuro[3,2-d]pyrimidine skeleton or a benzothieno[3,2-d]pyrimidine skeleton). Accordingly, a donor-acceptor excited state is easily formed in a molecule. Furthermore, the π-electron rich heteroaromatic ring and the π-electron deficient heteroaromatic ring are bonded directly or through an arylene group, which can improve both the donor property and the acceptor property. By increasing both the donor property and the acceptor property in the molecule, an overlap between a region where the HOMO is distributed and a region where the LUMO is distributed can be small, and the energy difference between the singlet excitation energy level and the triplet excitation energy level of the compound can be small. Moreover, the triplet excitation energy level of the compound can be kept high.

When the difference between the singlet excitation energy level and the triplet excitation energy level is small, with low thermal energy at 100° C. or lower, preferably at approximately room temperature, the triplet excitation energy can be upconverted to the singlet excitation energy by reverse intersystem crossing. That is, the compound of one embodiment of the present invention is an organic compound having a function of converting triplet excitation energy into singlet excitation energy. For efficient reverse intersystem crossing, the energy difference between the singlet excitation energy level and the triplet excitation energy level is preferably greater than 0 eV and less than or equal to 0.3 eV, more preferably greater than 0 eV and less than or equal to 0.2 eV, still more preferably greater than 0 eV and less than or equal to 0.1 eV.

Note that when the region where the HOMO is distributed and the region where the LUMO is distributed overlap each other and transition dipole moment between the HOMO level and the LUMO level is larger than 0, light emission can be obtained from an excited state related to the HOMO level and the LUMO level (e.g., the lowest singlet excited state). Therefore, the compound of one embodiment of the present invention is suitable as a light-emitting material having a function of converting the triplet excitation energy into the singlet excitation energy; in other words, the compound is suitable as a thermally activated delayed fluorescence material.

Note that a film of the organic compound of this embodiment can be formed by an evaporation method (including a vacuum evaporation method), an inkjet method, a coating method, a gravure printing method, or the like.

This embodiment can be combined with any of the other embodiments as appropriate.

Embodiment 2

In this embodiment, an example of a method for synthesizing the organic compound of one embodiment of the present invention (General Formula (G0)) having a benzofuro[3,2-d]pyrimidine skeleton or a benzothieno[3,2-d]pyrimidine skeleton is described.

[Chemical Formula 25]

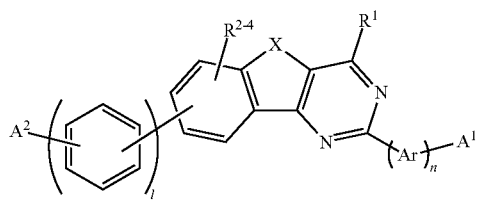

(G0)

Synthesis schemes of the organic compound represented by General Formula (G0) are shown below. As shown in Synthesis Scheme (S-1), the organic compound represented by General Formula (G0) is obtained by reaction between a halogen compound (A1) including a benzofuropyrimidine skeleton or a benzothienopyrimidine skeleton and a phenylboronic acid compound (A2) including a substituted or unsubstituted aromatic hydrocarbon group having 6 to 30 carbon atoms or a substituted or unsubstituted heteroaromatic hydrocarbon group having 3 to 30 carbon atoms.

[Chemical Formulae 26]

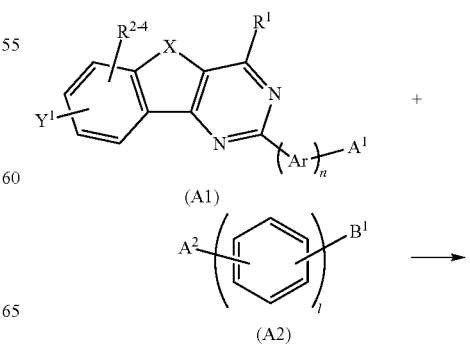

-continued

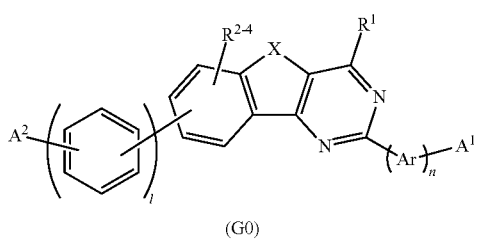

(G0)

As shown in Synthesis Scheme (S-2) below, the compound (A1) shown in Synthesis Scheme (S-1) is obtained by reaction between a dihalogen compound (B1) including a benzofuropyrimidine skeleton or a benzothienopyrimidine skeleton and an arylboronic acid compound (B2) including a substituted or unsubstituted aromatic hydrocarbon group having 6 to 30 carbon atoms or a substituted or unsubstituted heteroaromatic hydrocarbon group having 3 to 30 carbon atoms.

[Chemical Formulae 27]

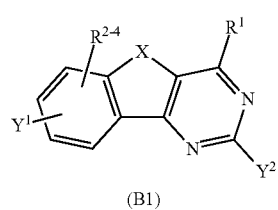

(S-2)

As shown in Synthesis Scheme (S-3) below, the compound (A1) shown in Synthesis Scheme (S-1) may be obtained by reaction between a dihalogen compound (C1) including a benzofuropyrimidine skeleton or a benzothienopyrimidine skeleton and a boronic acid compound (C2) including a substituted or unsubstituted aromatic hydrocarbon group having 6 to 30 carbon atoms or a substituted or unsubstituted heteroaromatic hydrocarbon group having 3 to 30 carbon atoms.

[Chemical Formulae 28]

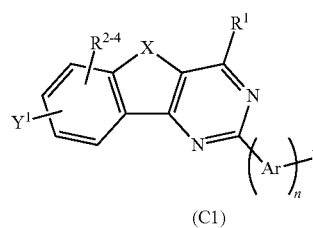

(S-3)

-continued

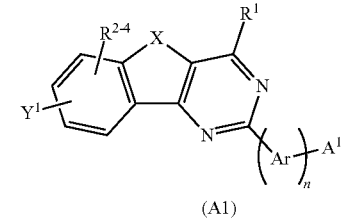

(A1)

As shown in Synthesis Scheme (S-4) below, the organic compound represented by General Formula (G0) can also be obtained by reaction between a halogen compound (D1) including a benzofuropyrimidine skeleton or a benzothienopyrimidine skeleton and the arylboronic acid compound (B2) including a substituted or unsubstituted aromatic hydrocarbon group having 6 to 30 carbon atoms or a substituted or unsubstituted heteroaromatic hydrocarbon group having 3 to 30 carbon atoms.

[Chemical Formulae 29]

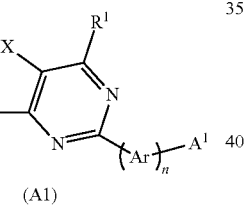

(S-4)

In Synthesis Schemes (S-1) to (S-4) above, X represents oxygen or sulfur, each of A and $A^2$ independently represents a substituted or unsubstituted aromatic hydrocarbon group having 6 to 30 carbon atoms or a substituted or unsubstituted heteroaromatic hydrocarbon group having 3 to 30 carbon atoms, Ar represents a substituted or unsubstituted arylene group having 6 to 25 carbon atoms, each of $R^1$ to R4 independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms, n is an integer of 0 to 4, and l is an integer of 1 to 4. In the schemes, $Y^1$ to $Y^4$ each represent a halogen element, and are preferably chlorine, bromine, or iodine. Furthermore, $B^1$ to $B^4$ each represent a boronic acid, a boronic ester, a cyclic-triolborate salt, or the like. As the cyclic-triolborate salt, a lithium salt, a potassium salt, or a sodium salt may be used.

Since various kinds of compounds are available commercially or can be synthesized as the compounds (A1), (A2), (B1), (B2), (C1), (C2), and (D1) in Synthesis Schemes (S-1) to (S-4) above, many kinds of organic compounds can be synthesized as the organic compound represented by General Formula (G0). Thus, the organic compound of one embodiment of the present invention is rich in variety.

Although an example of a method for synthesizing the organic compound of one embodiment of the present invention is described above, the present invention is not limited thereto and any other synthesis method may be employed.

Embodiment 3

In this embodiment, light-emitting elements including the organic compound of one embodiment of the present invention are described below with reference to FIGS. 1A to 1C.

Structure Example 1 of Light-Emitting Element

First, a structure of the light-emitting element of one embodiment of the present invention will be described with reference to FIGS. 1A to 1C.

FIG. 1A is a schematic cross-sectional view of a light-emitting element 150 of one embodiment of the present invention.

The light-emitting element 150 includes a pair of electrodes (an electrode 101 and an electrode 102) and an EL layer 100 between the pair of electrodes. The EL layer 100 includes at least a light-emitting layer 140.

The EL layer 100 illustrated in FIG. 1A includes functional layers such as a hole-injection layer 111, a hole-transport layer 112, an electron-transport layer 118, and an electron-injection layer 119, in addition to the light-emitting layer 140.

In this embodiment, although description is given assuming that the electrode 101 and the electrode 102 of the pair of electrodes serve as an anode and a cathode, respectively, the structure of the light-emitting element 150 is not limited thereto. That is, the electrode 101 may be a cathode, the electrode 102 may be an anode, and the stacking order of the layers between the electrodes may be reversed. In other words, the hole-injection layer 111, the hole-transport layer 112, the light-emitting layer 140, the electron-transport layer 118, and the electron-injection layer 119 may be stacked in this order from the anode side.

The structure of the EL layer 100 is not limited to the structure illustrated in FIG. 1A, and a structure including at least one layer selected from the hole-injection layer 111, the hole-transport layer 112, the electron-transport layer 118, and the electron-injection layer 119 may be employed. Alternatively, the EL layer 100 may include a functional layer which is capable of lowering a hole- or electron-injection barrier, improving a hole- or electron-transport property, inhibiting a hole- or electron-transport property, or suppressing a quenching phenomenon by an electrode, for example. Note that the functional layers may each be a single layer or stacked layers.

In the light-emitting element 150, at least one of the layers in the EL layer 100 contains the organic compound of one embodiment of the present invention. Note that the layer containing the organic compound is preferably the electron-transport layer 118, and more preferably the light-emitting layer 140. Furthermore, as described above, it is preferable that the organic compound of one embodiment of the present invention be used as a host material 141 in the light-emitting layer 140 and a substance capable of converting triplet excitation energy into light emission (in particular, a phosphorescent compound) be used as a guest material 142.

Figure 1B:
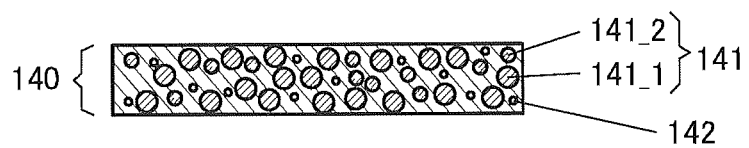

FIG. 1B is a schematic cross-sectional view illustrating an example of the light-emitting layer 140 in FIG. 1A. The light-emitting layer 140 in FIG. 1B includes the host material 141 and the guest material 142. The host material 141 may be a single organic compound or a co-host system including an organic compound 141_1 and an organic compound 141_2. The organic compound of one embodiment of the present invention can be used as the host material 141 or the organic compound 141_1.

The guest material 142 is a light-emitting organic material, and as examples of the light-emitting organic material, a material capable of emitting fluorescence (hereinafter referred to as a fluorescent material) and a phosphorescent compound can be given. A structure in which a phosphorescent compound is used as the guest material 142 will be described below. The guest material 142 may be rephrased as the phosphorescent compound.

In the case where two kinds of host materials such as the organic compound 141_1 and the organic compound 141_2 are used (co-host system) in the light-emitting layer as illustrated in FIG. 1B, one electron-transport material and one hole-transport material are generally used as the two kinds of host materials. Such a structure is preferable because it lowers a hole-injection barrier between the hole-transport layer 112 and the light-emitting layer 140 and an electron-injection barrier between the electron-transport layer 118 and the light-emitting layer 140 and thus reduces the driving voltage.

<Light Emission Mechanism of Light-Emitting Element>

Next, the light emission mechanism of the light-emitting layer 140 is described below.

The organic compound 141_1 and the organic compound 141_2 included in the host material 141 in the light-emitting layer 140 may form an excited complex (also referred to as exciplex). Described below is the case where the organic compound 141_1 and the organic compound 141_2 form an exciplex.

Figure 1C:
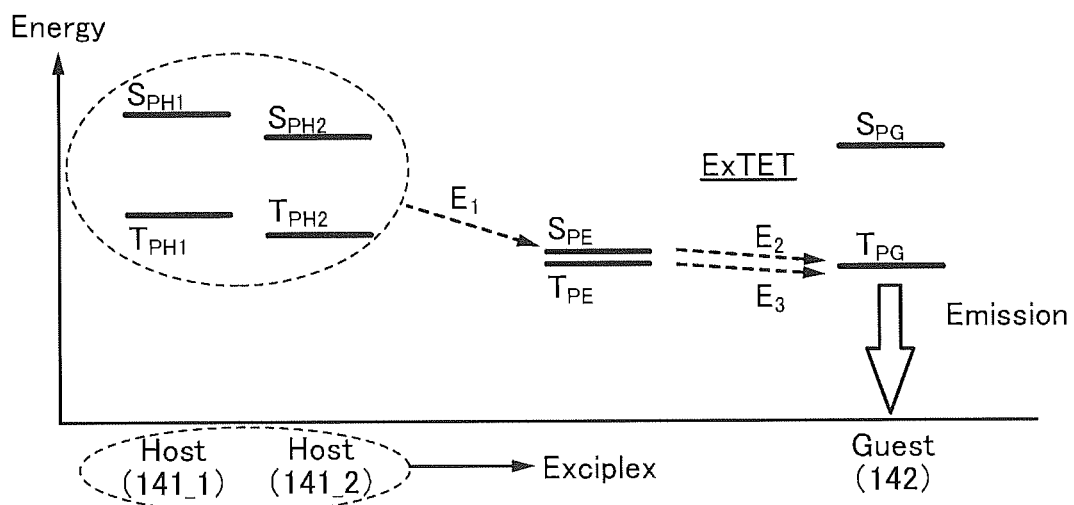
FIG. 1C shows a correlation between energy levels in a light-emitting layer.

FIG. 1C shows a correlation between the energy levels of the organic compound 141_1, the organic compound 141_2, and the guest material 142 in the light-emitting layer 140. What terms and numerals in FIG. 1C represent are listed below. Note that the organic compound 1411 is an electron-transport material and the organic compound 141_2 is a hole-transport material in the following description.

Host (141_1): the organic compound 141_1 (host material)

Host (141_2): the organic compound 141_2 (host material)

Guest (142): the guest material 142 (phosphorescent compound)

$S_{PH1}$: the S1 level of the organic compound 141_1 (host material)

$T_{PH1}$: the T1 level of the organic compound 141_1 (host material)

$S_{PH2}$: the S1 level of the organic compound 141_2 (host material)

$T_{PH2}$: the T1 level of the organic compound 141_2 (host material)

$S_{PG}$: the S1 level of the guest material 142 (phosphorescent compound)

$T_{PG}$: the T1 level of the guest material 142 (phosphorescent compound)

$S_{PE}$: the S1 level of the exciplex $T_{PE}$: the T1 level of the exciplex

The organic compound 14_1 and the organic compound 141_2 form an exciplex, and the S1 level ($S_{PE}$) and the T1 level ($T_{PE}$) of the exciplex are energy levels close to each other (see Route E in FIG. 1C).

The organic compound 141_1 and the organic compound 141_2 receive an electron and a hole, respectively, to readily form an exciplex. Alternatively, one of the organic compounds brought into an excited state immediately interacts with the other organic compound to form an exciplex. Consequently, most excitons in the light-emitting layer 140 exist as exciplexes. Because the excitation energy levels ($S_{PE}$ and $T_{PE}$) of the exciplex are lower than the S1 levels ($S_{PH1}$ and $S_{PH2}$) of the host materials (the organic compounds 141_1 and 141_2) that form the exciplex, the excited state of the host material 141 can be formed with lower excitation energy. This can reduce the driving voltage of the light-emitting element. The organic compound 1411 and the organic compound 141_2 may receive a hole and an electron, respectively, to form an exciplex.

Both energies of $S_{PE}$ and $T_{PE}$ of the exciplex are then transferred to the T1 level of the guest material 142 (the phosphorescent compound); thus, light emission is obtained (see Routes $E_2$ and $E_3$ in FIG. 1C).

Furthermore, the T1 level ($T_{PE}$) of the exciplex is preferably higher than the T1 level ($T_{PG}$) of the guest material 142. In this way, the singlet excitation energy and the triplet excitation energy of the formed exciplex can be transferred from the S1 level ($S_{PE}$) and the T1 level ($T_{PE}$) of the exciplex to the $T_1$ level ($T_{PG}$) of the guest material 142.

Note that in order to efficiently transfer excitation energy from the exciplex to the guest material 142, the T1 level ($T_{PE}$) of the exciplex is preferably lower than or equal to the T1 levels ($T_{PH1}$ and $T_{PH2}$) of the organic compounds (the organic compound 141_1 and the organic compound 141_2) which form the exciplex. Thus, quenching of the triplet excitation energy of the exciplex due to the organic compounds (the organic compounds 141_1 and 141_2) is less likely to occur, resulting in efficient energy transfer from the exciplex to the guest material 142.

In the case where the combination of the organic compounds 141_1 and 141_2 is a combination of a compound having a hole-transport property and a compound having an electron-transport property, the carrier balance can be easily controlled depending on the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

The above-described processes through Routes $E_2$ and $E_3$ may be referred to as exciplex-triplet energy transfer (ExTET) in this specification and the like. In other words, in the light-emitting layer 140, excitation energy is given from the exciplex to the guest material 142. In this case, the efficiency of reverse intersystem crossing from $T_{PE}$ to $S_{PE}$ and the emission quantum yield from $S_{PE}$ are not necessarily high; thus, materials can be selected from a wide range of options. Furthermore, ExTET allows the light-emitting element to have high emission efficiency, reduced driving voltage, and high reliability.

Although it is acceptable as long as the combination of the organic compound 141_1 and the organic compound 141_2 can form an exciplex, it is preferable that one have a lower HOMO) level and a lower LUMO (lowest unoccupied molecular orbital) level than the other.

The guest material 142 might receive a hole when the guest material 142 has a high HOMO level (which is higher than or equal to the HOMO level of the organic compound 141_1 and that of the organic compound 141_2) in the above structure. In that case, the guest material 142 and the organic compound 141_1 that is an electron-transport material might form an exciplex. Exciplex formation by the guest material 142 might reduce the emission efficiency of the light-emitting element or might prevent the above-described ExTET from being efficiently utilized.

The guest material 142 and the organic compound 141_1 readily form an exciplex when the gap between the HOMO level of the guest material 142 and the LUMO level of the organic compound 141_1 is small.

Here, the organic compound of one embodiment of the present invention has a high LUMO level as described in the above embodiment. Accordingly, when the organic compound of one embodiment of the present invention is used as the organic compound 141_1, the gap between the HOMO level of the guest material 142 and the LUMO level of the organic compound 141_1 can be large. As a result, exciplex formation by the guest material 142 and the organic compound 141_1 can be inhibited. In other words, the light-emitting element can have high emission efficiency even when the guest material 142 has a high HOMO level. Since ExTET can be utilized efficiently, the light-emitting element can have high emission efficiency, reduced driving voltage, and high reliability.

<Material>

Next, components of a light-emitting element of one embodiment of the present invention are described in detail below.

<<Light-Emitting Layer>>

In the light-emitting layer 140, the host material 141 is present in the largest proportion by weight, and the guest material 142 is dispersed in the host material 141. When the guest material 142 is a fluorescent compound, the S1 level of the host material 141 (the organic compound 141_1 and the organic compound 141_2) in the light-emitting layer 140 is preferably higher than the S1 level of the guest material (the guest material 142) in the light-emitting layer 140. When the guest material 142 is a phosphorescent compound, the T1 level of the host material 141 (the organic compound 141_1 and the organic compound 141_2) in the light-emitting layer 140 is preferably higher than the T1 level of the guest material (the guest material 142) in the light-emitting layer 140.

The organic compound 141_1 is preferably a compound having a nitrogen-containing six-membered heteroaromatic ring skeleton. In particular, the organic compound of one embodiment of the present invention can be suitably used because it includes a pyrimidine skeleton. Other specific examples thereof include compounds having any of a pyridine skeleton, a diazine skeleton (a pyrazine skeleton, a pyrimidine skeleton, and a pyridazine skeleton), and a triazine skeleton. As examples of these basic compounds having a nitrogen-containing heteroaromatic ring skeleton, compounds such as a pyridine derivative, a bipyridine derivative, a pyrimidine derivative, a triazine derivative, a quinoxaline derivative, a dibenzoquinoxaline derivative, a phenanthroline derivative, and a purine derivative can be given. As the organic compound 141_1, a material having a property of transporting more electrons than holes (an electron-transport material) can be used, and a material having an electron mobility of $1 \times 10^{-6}$ cm$^2$/Vs or higher is preferable.

Specific examples include heteroaromatic ring compounds having a pyridine skeleton such as bathophenanthroline (abbreviation: Bphen) and bathocuproine (abbreviation: BCP); heteroaromatic ring compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[f;h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heteroaromatic ring compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heteroaromatic ring compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the heteroaromatic ring compounds, the heteroaromatic ring compounds having a triazine skeleton, a diazine (pyrimidine, pyrazine, or pyridazine) skeleton, or a pyridine skeleton are highly reliable and stable and are thus preferably used. In addition, the heteroaromatic ring compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1 \times 10^{-6}$ cm$^2$/Vs or higher. Note that other substances may also be used as long as their electron-transport properties are higher than their hole-transport properties.

The organic compound 141_2 is preferably a compound having a nitrogen-containing five-membered heteroaromatic ring skeleton or a tertiary amine skeleton. Specific examples thereof include compounds having any of a pyrrole skeleton and an aromatic amine skeleton. As examples, an indole derivative, a carbazole derivative, a triarylamine derivative, and the like can be given. Examples of a nitrogen-containing five-membered heteroaromatic ring skeleton include an imidazole skeleton, a triazole skeleton, and a tetrazole skeleton. As the organic compound 141_2, a material having a property of transporting more holes than electrons (a hole-transport material) can be used, and a material having a hole mobility of $1 \times 10^{-6}$ cm$^2$/Vs or higher is preferable. Furthermore, the hole-transport material may be a high molecular compound.

Examples of the aromatic amine compounds that can be used as the material having a high hole-transport property are N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N-bis{4-[bis(3-methylphenyl)amino]phenyl}-N,N-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivative are 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Furthermore, it is possible to use N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), N,N,N',N',N'',N'',N''',N'''-octaphenyldibenzo[g,p]chrysene-2,7,10,15-tetraamine (abbreviation: DBC1), or the like.

Other examples are high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)metharylamide](abbreviation: PTPDMA), and poly[N,N-bis(4-butylphenyl)-N,N-bis(phenyl)benzidine](abbreviation: poly-TPD).

Examples of the material having a high hole-transport property include aromatic amine compounds such as 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), 4,4',4''-tris(carbazol-9-yl)triphenylamine (abbreviation: TCTA), 4,4',4''-tris[N-(1-naphthyl)-N-phenylamino]triphenylamine (abbreviation: 1'-TNATA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N-bis(9-phenylcarbazol-3-yl)-N,N-diphenylbenzene-1,3-diamine (abbreviation: PCA2B), N,N,N'-triphenyl-N,N,N'-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-

N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl] fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N-bis[4-(carbazol-9-yl)phenyl]-N,N-diphenyl-9,9-dimethylfluorene-2,7-diamine (abbreviation: YGA2F). Other examples are amine compounds, carbazole compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), and 2,8-di(9H-carbazol-9-yl)-dibenzothiophene (abbreviation: Cz2DBT). Among the above compounds, compounds having a pyrrole skeleton or an aromatic amine skeleton are preferred because of their high stability and reliability. In addition, the compounds having such skeletons have a high hole-transport property to contribute to a reduction in driving voltage.

As the organic compound 141_2, a compound having a nitrogen-containing five-membered heteroaromatic ring skeleton such as an imidazole skeleton, a triazole skeleton, or a tetrazole skeleton can be used. Specifically, 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), and the like can be used, for example.

Although the guest material 142 in the light-emitting layer 140 is not particularly limited, when the guest material 142 is a fluorescent compound, an anthracene derivative, a tetracene derivative, a chrysene derivative, a phenanthrene derivative, a pyrene derivative, a perylene derivative, a stilbene derivative, an acridone derivative, a coumalin derivative, a phenoxazine derivative, a phenothiazine derivative, or the like is preferred. For example, the following substances can be used.

Specifically, the following examples can be given: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl] pyrene-1,6-diamine (abbreviation: 1,6FLPAPrn), N,N-bis(3-methylphenyl)-N,N-bis[3-(9-phenyl-9H-fluoren-9-yl) phenyl]pyrene-1,6-diamine (abbreviation: 1,6mMemFLPAPrn), N,N-bis[4-(9-phenyl-9H-fluoren-9-yl)phenyl]-N,N-bis(4-tert-butylphenyl)pyrene-1,6-diamine (abbreviation: 1,6tBu-FLPAPrn), N,N-diphenyl-N,N-bis[4-(9-phenyl-9H-fluoren-9-yl)phenyl]-3,8-dicyclohexylpyrene-1,6-diamin e (abbreviation: ch-1,6FLPAPrn), N,N-bis[4-(9H-carbazol-9-yl)phenyl]-N,N-diphenylstilbene-4,4'-diamine (abbreviation: YGA2S),4-(9H-carbazol-9-yl)-4'-(10-phenyl-9-anthryl)triphenylamine(abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation:PCBAPA), N,N'-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N"N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N,N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylide ne}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJTM), and 5,10,15,20-tetraphenylbisbenzo[5,6]indeno[1,2,3-cd:1',2',3'-ln]perylene.

As the guest material 142 (phosphorescent compound), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

Examples of the substance that has an emission peak in the blue or green wavelength range include organometallic iridium complexes having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium (III) (abbreviation: Ir(iPrptz-3b)$_3$), and tris[3-(5-biphenyl)-

5-isopropyl-4-phenyl-4H-1,2,4-triazolato]iridium(III) (abbreviation: Ir(iPr5btz)$_3$); organometallic iridium complexes having a 1H-triazole skeleton, such as tris[3-methyl-1-(2-methylphenyl)-5-phenyl-1H-1,2,4-triazolato]iridium (III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-J]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyl)pyridinato-N,C$^{2'}$]iridium(III)acetylacetonate(abbreviation:FIr (acac)). Among the materials given above, the organometallic iridium complexes including a nitrogen-containing five-membered heteroaromatic ring skeleton, such as a 4H-triazole skeleton, a 1H-triazole skeleton, or an imidazole skeleton have high triplet excitation energy, reliability, and emission efficiency and are thus especially preferable.

Examples of the substance that has an emission peak in the green or yellow wavelength range include organometallic iridium complexes having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), (acetylacetonato)bis{4,6-dimethyl-2-[6-(2,6-dimethylphenyl)-4-pyrimidinyl-κN3]phenyl-κC}iridium(III) (abbreviation: Ir(dmppm-dmp)$_2$(acac)), and (acetylacetonato)bis(4,6-diphenylpyrimidinato)iridium(III) (abbreviation: Ir(dppm)$_2$(acac)); organometallic iridium complexes having a pyrazine skeleton, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), and bis(2-phenylquinolinato-N,C$^{2'}$)iridium (III) acetylacetonate (abbreviation: Ir(pq)$_2$(acac)); organometallic iridium complexes such as bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N,C$^{2'}$}iridium(III) acetylacetonate (abbreviation: Ir(p-PF-ph)$_2$(acac)), and bis(2-phenylbenzothiazolato-N,C$^{2'}$) iridium(III) acetylacetonate (abbreviation: Ir(bt)$_2$(acac)); and a rare earth metal complex such as tris(acetylacetonato)(monophenanthroline)terbium(III) (abbreviation: Tb(acac)$_3$(Phen)). Among the materials given above, the organometallic iridium complexes having a pyrimidine skeleton have distinctively high reliability and light emission efficiency and are thus particularly preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis [4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(dlnpm)$_2$(dpm)); organometallic iridium complexes having a pyrazine skeleton, such as (acetylacetonato)bis(2,3,5-triphenylpyrazinato)iridium (III) (abbreviation: Ir(tppr)$_2$(acac)), bis(2,3,5-triphenylpyrazinato)(dipivaloylmethanato)iridium(III) (abbreviation: Ir(tppr)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes having a pyridine skeleton, such as tris(1-phenylisoquinolinato-N,C$^{2'}$)iridium(III) (abbreviation: Ir(piq)$_3$) and bis(1-phenylisoquinolinato-N,C$^{2'}$)iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: Eu(DBM)$_3$(Phen)) and tris [1-(2-thenoyl)-3,3,3-trifluoroacetonato](monophenanthroline)europium(III) (abbreviation: Eu(TTA)$_3$(Phen)). Among the materials given above, the organometallic iridium complexes having a pyrimidine skeleton have distinctively high reliability and light emission efficiency and are thus particularly preferable. Further, the organometallic iridium complexes having a pyrazine skeleton can provide red light emission with favorable chromaticity.

An organic compound including a benzofuropyrazine skeleton or a benzothienopyrazine skeleton has a high T1 level, and thus can be suitably used as a host material in a light-emitting layer containing a substance capable of converting triplet excitation energy into light emission as a light-emitting material. Accordingly, the light-emitting material included in the light-emitting layer 140 is preferably a material that can convert the triplet excitation energy into light emission. As an example of the material that can convert the triplet excitation energy into light emission, a thermally activated delayed fluorescence (TADF) material can be given in addition to the above-described phosphorescent compound. Therefore, it is acceptable that the "phosphorescent compound" in the description is replaced with the "thermally activated delayed fluorescence material". Note that the thermally activated delayed fluorescence material is a material having a small difference between the triplet excitation energy level and the singlet excitation energy level and a function of converting triplet excitation energy into singlet excitation energy by reverse intersystem crossing. Thus, the TADF material can up-convert a triplet excited state into a singlet excited state (i.e., reverse intersystem crossing is possible) using a little thermal energy and efficiently exhibit light emission (fluorescence) from the singlet excited state. The TADF is efficiently obtained under the condition where the difference in energy between the triplet excitation energy level and the singlet excitation energy level is preferably larger than 0 eV and smaller than or equal to 0.2 eV, further preferably larger than 0 eV and smaller than or equal to 0.1 eV. As the thermally activated delayed fluorescence material, the compound described in Embodiment 1 is also preferably used.

In the case where the thermally activated delayed fluorescence material is composed of one kind of material, any of the following materials can be used, for example.

First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$(OEP)).

As the thermally activated delayed fluorescence material composed of one kind of material, a heteroaromatic ring compound including a A-electron rich heteroaromatic ring and a A-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), or the like can be used. The heteroaromatic ring compound is preferable because of having the π-electron rich heteroaromatic ring and the A-electron deficient heteroaromatic ring, for which the electron-transport property and the hole-transport property are high. Among skeletons having the π-electron deficient heteroaromatic ring, a diazine skeleton (a pyrimidine skeleton, a pyrazine skeleton, or a pyridazine skeleton) and a triazine skeleton have high stability and reliability and are particularly preferable. Among skeletons having the A-electron rich heteroaromatic ring, an acridine skeleton, a phenoxazine skeleton, a thiophene skeleton, a furan skeleton, and a pyrrole skeleton have high stability and reliability; therefore, one or more of these skeletons are preferably included. As the pyrrole skeleton, an indole skeleton, a carbazole skeleton, or a 3-(9-phenyl-9H-carbazol-3-yl)-9H-carbazole skeleton is particularly preferred. Note that a substance in which the T-electron rich heteroaromatic ring is directly bonded to the r-electron deficient heteroaromatic ring is particularly preferable because the donor property of the π-electron rich heteroaromatic ring and the acceptor property of the Tc-electron deficient heteroaromatic ring are both high and the difference between the energy level in the singlet excited state and the energy level in the triplet excited state becomes small.

The light-emitting layer 140 may include a material other than the host material 141 and the guest material 142.

Examples of the material that can be used for the light-emitting layer 140 are, but not limited to, fused polycyclic aromatic compounds such as anthracene derivatives, phenanthrene derivatives, pyrene derivatives, chrysene derivatives, and dibenzo[g,p]chrysene derivatives. Specific example of the fused polycyclic aromatic compounds include 9,10-diphenylanthracene (abbreviation: DPAnth), 6,12-dimethoxy-5,11-diphenylchrysene, 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a singlet excitation energy level or a triplet excitation energy level higher than the excitation energy level of the guest material 142 are selected from these substances and known substances.

For example, a compound having a heteroaromatic ring skeleton, such as an oxadiazole derivative, can be used for the light-emitting layer 140. As specific examples thereof, heteroaromatic ring compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), and 4,4'-bis(5-methylbenzoxazol-2-yl)stilbene (abbreviation: BzOs) can be given.

In addition, a metal complex (e.g., a zinc- or aluminum-based metal complex) with a heteroaromatic ring, for example, can be used for the light-emitting layer 140. As examples, metal complexes having a quinoline ligand, a benzoquinoline ligand, an oxazole ligand, and a thiazole ligand can be given. Specific examples thereof include metal complexes having a quinoline or benzoquinoline skeleton, such as tris(8-quinolinolato)aluminum(III) (abbreviation: Alq), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ), can be used.

The light-emitting layer 140 can have a structure in which two or more layers are stacked. For example, in the case where the light-emitting layer 140 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. A light-emitting material included in the first light-emitting layer may be the same as or different from a light-emitting material included in the second light-emitting layer. In addition, the materials may have functions of emitting light of the same color or light of different colors. Light-emitting materials having functions of emitting light of different colors are used for the two light-emitting layers, so that light of a plurality of emission colors can be obtained at the same time. It is particularly preferable to select light-emitting materials of the light-emitting layers so that white light can be obtained by combining light emission from the two light-emitting layers.

Note that the light-emitting layer 140 can be formed by an evaporation method (including a vacuum evaporation method), an inkjet method, a coating method, gravure printing, or the like. Besides the above-mentioned materials, an inorganic compound such as a quantum dot or a high molecular compound (e.g., an oligomer, a dendrimer, and a polymer) may be used.

<<Hole-Injection Layer>>

The hole-injection layer 111 has a function of lowering a barrier for hole injection from one of the pair of electrodes (the electrode 101 or the electrode 102) to promote hole injection and is formed using a transition metal oxide, a phthalocyanine derivative, or an aromatic amine, for example. As the transition metal oxide, molybdenum oxide, vanadium oxide, ruthenium oxide, tungsten oxide, manganese oxide, and the like can be given. As the phthalocyanine derivative, phthalocyanine, metal phthalocyanine, and the like can be given. As the aromatic amine, a benzidine derivative, a phenylenediamine derivative, and the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron-accepting property and a layer containing a hole-transport material may also be used. In a steady state or in the presence of an electric field, electric charge can be transferred between these materials. As examples of the material having an electron-accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1 \times 10^{-6}$ cm$^2$/Vs or higher is preferable. Specifically, any of the aromatic amine, carbazole derivative, aromatic hydrocarbon, stilbene derivative, and the like described as examples of the hole-transport material that can be used in the light-emitting layer 140 can be used. Furthermore, the hole-transport material may be a high molecular compound.

As other examples of the hole-transport material, aromatic hydrocarbons such as 2-tert-butyl-9,10-di(2-naphthyl) anthracene (abbreviation: t-BuDNA), 2-tert-butyl-9,10-di(1-naphthyl)anthracene, 9,10-bis(3,5-diphenylphenyl) anthracene (abbreviation:DPPA),2-tert-butyl-9,10-bis(4-phenylphenyl)anthracene (abbreviation:t-BuDBA), 9,10-di (2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene can be given. Other examples are pentacene, coronene, and the like. The aromatic hydrocarbon having a hole mobility of $1 \times 10^{-6}$ cm$^2$/Vs or higher and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are thiophene compounds, furan compounds, fluorene compounds, triphenylene compounds, phenanthrene compounds, and the like such as 4-{3-[3-(9-phenyl-9H-fluoren-9-yl)phenyl]phenyl}dibenzofuran(abbreviation:mmDBFFLBi-II), 4,4',4''-(benzene-1,3,5-triyl)tri (dibenzofuran) (abbreviation: DBF3P-II), 1,3,5-tri (dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene(abbreviation: DBTFLP-IV), and 4-[3-(triphenylen-2-yl)phenyl] dibenzothiophene (abbreviation: mDBTPTp-II). Among the above compounds, compounds including a pyrrole skeleton, a furan skeleton, a thiophene skeleton, or an aromatic amine skeleton are preferred because of their high stability and reliability. In addition, the compounds having such skeletons have a high hole-transport property to contribute to a reduction in driving voltage.

<<Hole-Transport Layer>>

The hole-transport layer 112 is a layer containing a hole-transport material and can be formed using any of the hole-transport materials given as examples of the material of the hole-injection layer 111. In order that the hole-transport layer 112 can have a function of transporting holes injected into the hole-injection layer 111 to the light-emitting layer 140, the highest occupied molecular orbital (HOMO) level of the hole-transport layer 112 is preferably equal or close to the HOMO level of the hole-injection layer 111.

As the hole-transport material, a substance having a hole mobility of $1 \times 10^{-6}$ cm$^2$/Vs or higher is preferably used. Note that any substance other than the above substances may be used as long as the hole-transport property is higher than the electron-transport property. The layer including a substance having a high hole-transport property is not limited to a single layer, and two or more layers containing the aforementioned substances may be stacked.

<<Electron-Transport Layer>>

The electron-transport layer 118 has a function of transporting, to the light-emitting layer 140, electrons injected from the other of the pair of electrodes (the electrode 101 or the electrode 102) through the electron-injection layer 119. A material having a property of transporting more electrons than holes can be used as the electron-transport material, and a material having an electron mobility of $1 \times 10^{-6}$ cm$^2$/Vs or higher is preferable. As a compound that easily accepts electrons (a material having an electron-transport property), a π-electron deficient heteroaromatic ring compound such as a nitrogen-containing heteroaromatic ring compound or a metal complex can be used. The organic compound of one embodiment of the present invention can be suitably used because it includes a pyrimidine skeleton. Other specific examples of the material having an electron-transport property include a pyridine derivative, a bipyridine derivative, a pyrimidine derivative, a triazine derivative, a quinoxaline derivative, a dibenzoquinoxaline derivative, a phenanthroline derivative, a triazole derivative, a benzimidazole derivative, and an oxadiazole derivative, which are described above as the electron-transport material that can be used for the light-emitting layer 140. A substance having an electron mobility of $1\times10^{-6}$ cm$^2$/Vs or higher is preferable. Note that other than these substances, any substance that has a property of transporting more electrons than holes may be used for the electron-transport layer. The electron-transport layer 118 is not limited to a single layer, and may include stacked two or more layers containing the aforementioned substances.

In addition, metal complexes with a heteroaromatic ring, such as metal complexes having a quinoline ligand, a benzoquinoline ligand, an oxazole ligand, and a thiazole ligand, can be given. Specific examples thereof include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ), can be used.

Between the electron-transport layer 118 and the light-emitting layer 140, a layer that controls transfer of electron carriers may be provided. This is a layer formed by addition of a small amount of a substance having a high electron-trapping property to a material having a high electron-transport property as described above, and the layer is capable of adjusting carrier balance by suppressing transport of electron carriers. Such a structure is very effective in suppressing a problem (e.g., a decrease in element lifetime) which occurs in the case where the electron-transport property of the electron-transport material is significantly higher than the hole-transport property of the hole-transport material.

<<Electron-Injection Layer>>

The electron-injection layer 119 has a function of lowering a barrier for electron injection at an interface between the electron-injection layer 119 and the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, and the like can be given. Specifically, an alkali metal, an alkaline earth metal, or a compound thereof, such as lithium fluoride (LiF), sodium fluoride (NaF), cesium fluoride (CsF), calcium fluoride (CaF$_2$), or lithium oxide (LiOx), can be used. Alternatively, a rare earth metal compound like erbium fluoride (ErF$_3$) can be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 118 (e.g., the metal complexes and heteroaromatic ring compounds) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

<<Quantum Dot>>

A quantum dot is a semiconductor nanocrystal with a size of several nanometers to several tens of nanometers and contains approximately $1\times10^3$ to $1\times10^6$ atoms. Since energy shift of quantum dots depend on their size, quantum dots made of the same substance emit light with different wavelengths depending on their size; thus, emission wavelengths can be easily adjusted by changing the size of quantum dots.

Since a quantum dot has an emission spectrum with a narrow peak, emission with high color purity can be obtained. In addition, a quantum dot is said to have a theoretical internal quantum efficiency of approximately 100%, which far exceeds that of a fluorescent organic compound, i.e., 25%, and is comparable to that of a phosphorescent organic compound. Therefore, a quantum dot can be used as a light-emitting material to obtain a light-emitting element having high emission efficiency. Furthermore, since a quantum dot which is an inorganic material has high inherent stability, a light-emitting element which is favorable also in terms of lifetime can be obtained.

Examples of a material of a quantum dot include a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; iron oxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is a means effective in obtaining blue light because the emission wavelength can be changed by changing the content ratio of elements.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since band gaps of quantum dots are increased as their size is decreased, the size is adjusted as appropriate so that light with a desired wavelength can be obtained. Light emission from the quantum dots is shifted to a blue color side, i.e., a high energy side, as the crystal size is decreased; thus, emission wavelengths of the quantum dots can be adjusted over a wavelength range of a spectrum of an ultraviolet region, a visible light region, and an infrared region by changing the size of quantum dots. The range of size (diameter) of quantum dots which is usually used is 0.5 nm to 20 nm, preferably 1 nm to 10 nm. The emission spectra are narrowed as the size distribution of the quantum dots gets smaller, and thus light can be obtained with high color purity. The shape of the quantum dots is not particularly limited and may be a spherical shape, a rod shape, a circular shape, or the like. Quantum rods which are rod-like shape quantum dots have a function of emitting directional light; thus, quantum rods can be used as a light-emitting material to obtain a light-emitting element with higher external quantum efficiency.

In most organic EL elements, to improve emission efficiency, concentration quenching of the light-emitting materials is suppressed by dispersing light-emitting materials in host materials. The host materials need to be materials having singlet excitation energy levels or triplet excitation energy levels higher than or equal to those of the light-emitting materials. In the case of using blue phosphorescent compounds as light-emitting materials, it is particularly difficult to develop host materials which have triplet excitation energy levels higher than or equal to those of the blue phosphorescent materials and which are excellent in terms of a lifetime. Even when a light-emitting layer is composed of quantum dots and made without a host material, the quantum dots enable emission efficiency to be ensured; thus, a light-emitting element which is favorable in terms of a lifetime can be obtained. In the case where the light-emitting layer is composed of quantum dots, the quantum dots preferably have core-shell structures (including core-multi-shell structures).

In the case of using quantum dots as the light-emitting material in the light-emitting layer, the thickness of the light-emitting layer is set to 3 nm to 100 nm, preferably 10 nm to 100 nm, and the quantum dot content of the light-emitting layer is 1 volume % to 100 volume %. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, a blade coating method, a roll coating method, an ink-jet method, a printing method, a spray coating method, a curtain coating method, or a Langmuir-Blodgett method) may be employed. For a light-emitting layer containing a phosphorescent material, a vacuum evaporation method, as well as the wet process, can be suitably employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

<<Pair of Electrodes>>

The electrodes 101 and 102 function as an anode and a cathode of the light-emitting element. The electrodes 101 and 102 can be formed using a metal, an alloy, or a conductive compound, a mixture or a stack thereof, or the like.

One of the electrode 101 and the electrode 102 is preferably formed using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, Ag, an alloy of silver (Ag) and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1 \times 10^{-2}$ Ω·cm can be used.

The electrodes 101 and 102 may each be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1 \times 10^{-2}$ Ω·cm can be used. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, as the material transmitting light, a material that transmits visible light and has conductivity is used. Examples of the material include, in addition to the above-described oxide conductor typified by an ITO, an oxide semiconductor and an organic conductor containing an organic substance. Examples of the organic conductor containing an organic substance include a composite material in which an organic compound and an electron donor (donor) are mixed and a composite material in which an organic compound and an electron acceptor (acceptor) are mixed. Alternatively, an inorganic carbon-based material such as graphene may be used. The resistivity of the material is preferably lower than or equal to $1 \times 10^5$ Ω·cm, further preferably lower than or equal to $1 \times 10^4$ Ω·cm.

Alternatively, the electrode 101 and/or the electrode 102 may be formed by stacking two or more of these materials.

In order to improve the light extraction efficiency, a material whose refractive index is higher than that of an electrode having a function of transmitting light may be formed in contact with the electrode. The material may be electrically conductive or non-conductive as long as it has a function of transmitting visible light. In addition to the oxide conductors described above, an oxide semiconductor and an organic substance are given as the examples of the material. Examples of the organic substance include the materials for the light-emitting layer, the hole-injection layer, the hole-transport layer, the electron-transport layer, and the electron-injection layer. Alternatively, an inorganic carbon-based material or a metal film thin enough to transmit light can be used. Further alternatively, stacked layers with a thickness of several nanometers to several tens of nanometers may be used.

In the case where the electrode 101 or the electrode 102 functions as the cathode, the electrode preferably contains a material having a low work function (lower than or equal to 3.8 eV). For example, it is possible to use an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum or silver, or the like.

When the electrode 101 or the electrode 102 is used as an anode, a material with a high work function (4.0 eV or higher) is preferably used.

The electrode 101 and the electrode 102 may be a stacked layer of a conductive material having a function of reflecting light and a conductive material having a function of transmitting light. In that case, the electrode 101 and the electrode 102 can have a function of adjusting the optical path length so that light of a desired wavelength emitted from each light-emitting layer resonates and is intensified, which is preferable.

As the method for forming the electrode 101 and the electrode 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element of one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element or as long as it has a function of protecting the light-emitting element or an optical element.

In this specification and the like, a light-emitting element can be formed using any of a variety of substrates, for example. The type of a substrate is not limited particularly. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper which includes a fibrous material, a base material film, and the like. As an example of a glass substrate, a barium borosilicate glass substrate, an alumino-borosilicate glass substrate, a soda lime glass substrate, and the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, paper, and the like.

Alternatively, a flexible substrate may be used as the substrate such that the light-emitting element is provided directly on the flexible substrate. Further alternatively, a separation layer may be provided between the substrate and the light-emitting element. The separation layer can be used when part or the whole of a light-emitting element formed over the separation layer is separated from the substrate and transferred onto another substrate. In such a case, the light-emitting element can be transferred to a substrate having low heat resistance or a flexible substrate as well. For the above separation layer, a stack including inorganic films, which are a tungsten film and a silicon oxide film, or a structure in which a resin film of polyimide or the like is formed over a substrate can be used, for example.

In other words, after the light-emitting element is formed using a substrate, the light-emitting element may be transferred to another substrate. Examples of the substrate to which the light-emitting element is transferred are, in addition to the above substrates, a cellophane substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), and the like), a leather substrate, a rubber substrate, and the like. When such a substrate is used, a light-emitting element with high durability, high heat resistance, reduced weight, or reduced thickness can be formed.

The light-emitting element 150 may be formed over an electrode electrically connected to a field-effect transistor (FET), for example, that is formed over any of the above-described substrates. Accordingly, an active matrix display device in which the FET controls the driving of the light-emitting element 150 can be manufactured.

The structure described above in this embodiment can be combined with any of the structures described in the other embodiments as appropriate.

Embodiment 4

Figure 2:
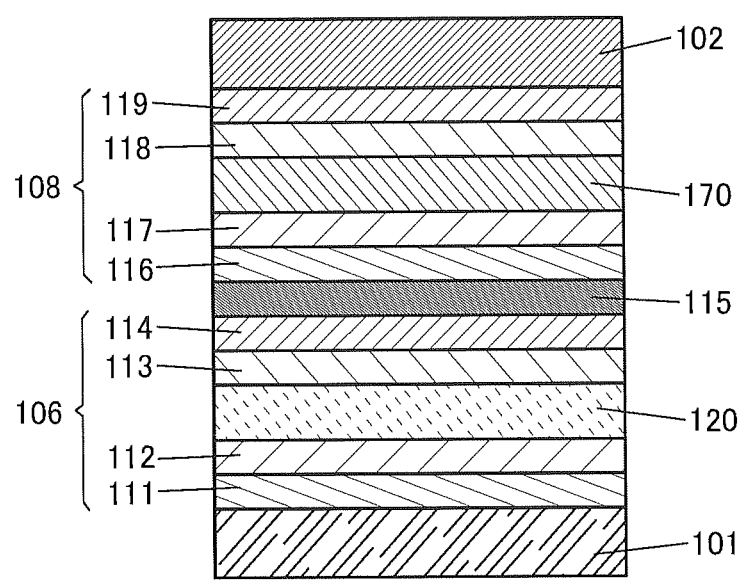
FIG. 2 is a schematic view of a light-emitting element of one embodiment of the present invention.

In this embodiment, a light-emitting element having a structure different from that described in Embodiment 3 will be described below with reference to FIG. 2. In FIG. 2, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

Structure Example 2 of Light-Emitting Element

FIG. 2 is a schematic cross-sectional view of a light-emitting element 250.

The light-emitting element 250 illustrated in FIG. 2 includes a plurality of light-emitting units (a light-emitting unit 106 and a light-emitting unit 108) between a pair of electrodes (the electrode 101 and the electrode 102). One of the light-emitting units preferably has the same structure as the EL layer 100 illustrated in FIG. 1A. That is, it is preferable that the light-emitting element 150 illustrated in FIG. 1A include one light-emitting unit while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 2, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable that a structure similar to that of the EL layer 100 be used in the light-emitting unit 108.

The light-emitting element 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 170. The light-emitting unit 108 includes a hole-injection layer 116, a hole-transport layer 117, the electron-transport layer 118, and the electron-injection layer 119 in addition to the light-emitting layer 120.

In the light-emitting element 250, any layer of each of the light-emitting unit 106 and the light-emitting unit 108 contains the organic compound of one embodiment of the present invention. Note that the layer containing the organic compound is preferably the electron-transport layer 113 or the electron-transport layer 118, and more preferably the light-emitting layer 120 or the light-emitting layer 170.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 3 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A material having a hole mobility of $1 \times 10^{-6}$ cm$^2$/Vs or higher is preferably used as the organic compound. Note that any other substance may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115, the charge-generation layer 115 can also serve as a hole-injection layer or a hole-transport layer of the light-emitting unit; thus, a hole-injection layer or a hole-transport layer is not necessarily included in the light-emitting unit. Alternatively, when a surface of the light-emitting unit on the cathode side is in contact with the charge-generation layer 115, the charge-generation layer 115 can also serve as an electron-injection layer or an electron-transport layer of the light-emitting unit; thus, an electron-injection layer or an electron-transport layer is not necessarily included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive film.

The charge-generation layer 115 provided between the light-emitting unit 106 and the light-emitting unit 108 is configured so that electrons are injected into one of the light-emitting units and holes are injected into the other light-emitting unit when a voltage is applied between the electrode 101 and the electrode 102. For example, in FIG. 3A, the charge-generation layer 115 injects electrons into the light-emitting unit 106 and holes into the light-emitting unit 108 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even when having lower conductivity than the pair of electrodes (the electrodes 101 and 102).

The charge-generation layer 115 formed by using any of the above materials can suppress an increase in driving voltage caused by the stack of the light-emitting layers.

Although FIG. 2 illustrates the light-emitting element including the two light-emitting units, the light-emitting element can include three or more light-emitting units stacked. With a plurality of light-emitting units between a pair of electrodes, which are partitioned by the charge-generation layer as in the light-emitting element 250, it is possible to provide a light-emitting element which can emit high-luminance light with the current density kept low, has a long lifetime, and consumes low power.

Note that in each of the above-described structures, the emission colors of the guest materials used in the light-emitting unit 106 and the light-emitting unit 108 may be the same or different. In the case where guest materials emitting light of the same color are used for the light-emitting unit 106 and the light-emitting unit 108, the light-emitting element 250 can exhibit high emission luminance at a small current value, which is preferable. In the case where guest materials emitting light of different colors are used for the light-emitting unit 106 and the light-emitting unit 108, the light-emitting element 250 can exhibit multi-color light emission, which is preferable. In that case, when a plurality of light-emitting materials with different emission wavelengths are used in one or both of the light-emitting layers 120 and 170, the light-emitting element 250 emits light obtained by synthesizing lights with different emission peaks. That is, the emission spectrum of the light-emitting element 250 has at least two local maximum values.

The above structure is also suitable for obtaining white light emission. When the light-emitting layer 120 and the light-emitting layer 170 emit light of complementary colors, white light emission can be obtained. It is particularly favorable to select the guest materials so that white light emission with high color rendering properties or light emission of at least red, green, and blue can be obtained.

In the case of a light-emitting element in which three or more light-emitting units are stacked, colors of light emitted from guest materials in the light-emitting units may be the same or different from each other. In the case where the light-emitting element includes a plurality of light-emitting units emitting light of the same color, these light-emitting units can exhibit light of the color with higher emission luminance with a smaller current value as compared with light of the other colors. Such a structure can be suitably used to adjust light emission colors. In particular, the structure is suitably used in the case where guest materials which emit light of different colors with different emission efficiencies are used. For example, when the light-emitting element has a three-layer structure of light-emitting units, the light-emitting units are two light-emitting units including a fluorescent material and emitting light of the same color and one light-emitting unit including a phosphorescent compound and emitting light of a color different from the color of the fluorescent material, in which case the intensity of fluorescence and phosphorescence can be adjusted. Thus, the intensity of light emission of colors can be adjusted by changing the number of light-emitting units.

When a light-emitting element includes two light-emitting units for fluorescence and one light-emitting unit for phosphorescence in the above-described manner, preferable combinations of the light-emitting units are as follows: a combination of two light-emitting units including a blue fluorescent material and one light-emitting unit including a yellow phosphorescent compound; a combination of two light-emitting units including a blue fluorescent material and one light-emitting unit including a red phosphorescent compound and a green phosphorescent compound; and a combination of two light-emitting units including a blue fluorescent material and one light-emitting unit including a red phosphorescent compound, a yellow phosphorescent compound, and a green phosphorescent compound. The combinations are preferable because they enable efficient white light emission.

At least one of the light-emitting layers 120 and 170 may be divided into layers and each of the divided layers may contain different light-emitting materials. That is, at least one of the light-emitting layers 120 and 170 may consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. A light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

In addition, the light-emitting layer of the light-emitting unit 108 preferably contains a phosphorescent compound. When the structure with the organic compound of one embodiment of the present invention is used for at least one of the plurality of units, a light-emitting element with high emission efficiency and high reliability can be provided.

This embodiment can be combined with any of the other embodiments as appropriate.

Embodiment 5

In this embodiment, a light-emitting device including the light-emitting element described in Embodiment 3 and Embodiment 4 is described with reference to FIGS. 3A and 3B.

Figure 3A:
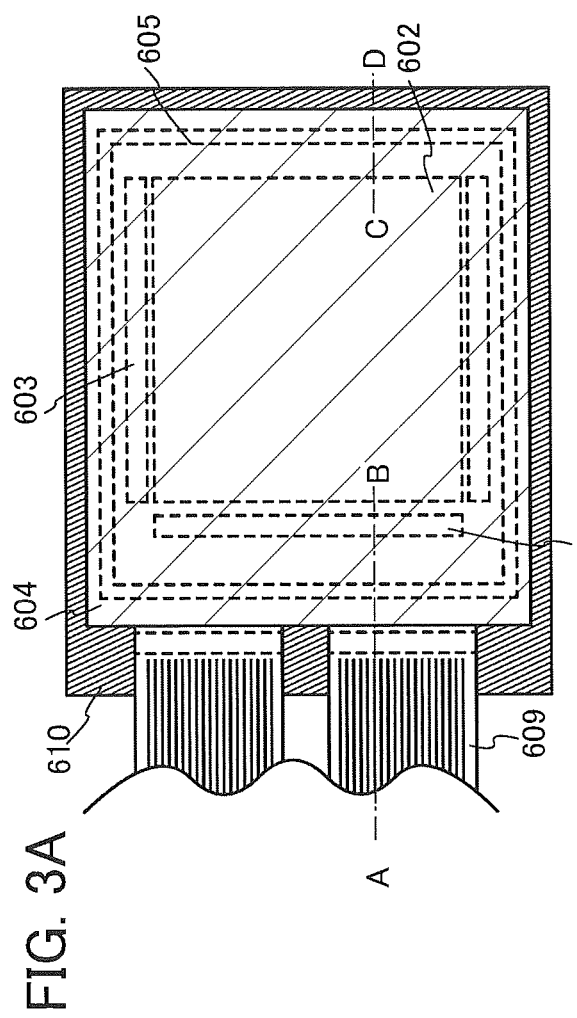
FIGS. 3A and 3B are schematic diagrams of an active matrix light-emitting device of one embodiment of the present invention.
Figure 3B:
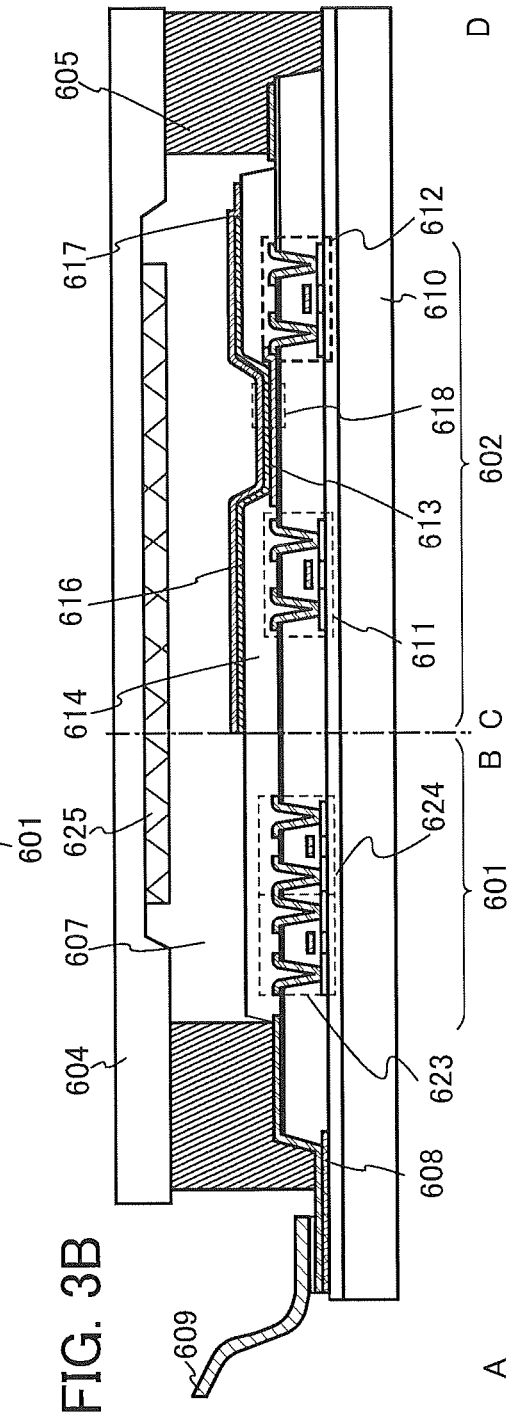

FIG. 3A is a top view of the light-emitting device and FIG. 3B is a cross-sectional view taken along the lines A-B and C-D in FIG. 3A. The light-emitting device includes a driver circuit portion (source side driver circuit) 601, a pixel portion 602, and a driver circuit portion (gate side driver circuit) 603, which control light emission of a light-emitting element and are illustrated with dotted lines. Moreover, a reference numeral 604 denotes a sealing substrate, a reference numeral 625 denotes a desiccant, and a reference numeral 605 denotes a sealant. A portion surrounded by the sealant 605 is a space 607.

Note that a lead wiring 608 is a wiring for transmitting signals to be input to the source side driver circuit 601 and the gate side driver circuit 603 and for receiving a video signal, a clock signal, a start signal, a reset signal, and the like from a flexible printed circuit (FPC) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure of the light-emitting device is described with reference to FIG. 3B. The driver circuit portion and the pixel portion are formed over an element substrate 610. Here, the source side driver circuit 601, which is the driver circuit portion, and one pixel of the pixel portion 602 are illustrated.

In the source side driver circuit 601, a CMOS circuit is formed in which an n-channel TFT 623 and a p-channel TFT 624 are combined. The driver circuit may be formed using various circuits such as a CMOS circuit, a PMOS circuit, or an NMOS circuit. Although a driver-integrated type in which the driver circuit is formed over the substrate is described in this embodiment, the driver circuit is not necessarily formed over the substrate, and may be formed outside the substrate.

The pixel portion 602 includes a plurality of pixels including a switching TFT 611, a current controlling TFT 612, and a first electrode 613 electrically connected to a drain of the current controlling TFT 612. Note that an insulator 614 is formed to cover an end portion of the first electrode 613. The insulator 614 can be formed using a positive photosensitive resin film.

In order to improve coverage with a film that is formed over the insulator 614, the insulator 614 is formed to have a curved surface with curvature at its upper or lower end portion. For example, in the case where photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. As a material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, Ca, or an alloy or a compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that a light-emitting element 618 is formed with the first electrode 613, the EL layer 616, and the second electrode 617. The light-emitting element 618 preferably has the structure described in Embodiment 3 and Embodiment 4. In the light-emitting device of this embodiment, the pixel portion, which includes a plurality of light-emitting elements, may include both the light-emitting element with the structure described in Embodiment 3 and Embodiment 4 and a light-emitting element with a different structure.

The sealing substrate 604 is attached to the element substrate 610 with the sealant 605, so that the light-emitting element 618 is provided in the space 607 surrounded by the element substrate 610, the sealing substrate 604, and the sealant 605. The space 607 is filled with a filler. The filler may be an inert gas (such as nitrogen or argon), or a resin and/or a desiccant.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), polyvinyl fluoride (PVF), polyester, acrylic, or the like can be used.

As described above, the light-emitting device including the light-emitting element described in Embodiment 3 and Embodiment 4 can be obtained.

Structure Example 1 of Light-Emitting Device

As an example of a light-emitting device, FIGS. 4A and 4B each illustrate a light-emitting device including a light-emitting element exhibiting white light emission and a coloring layer (a color filter).

FIG. 4A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1026, an EL layer 1028, a second electrode 1029 of the light-emitting elements, a sealing substrate 1031, a sealant 1032, and the like.

In FIG. 4A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 4A, light emission obtained from the EL layer 1028 includes light extracted to the outside without passing through the coloring layers and light extracted to the outside after passing through the coloring layers. Since light that does not pass through the coloring layers is white and light that passes through any one of the coloring layers is red, blue, or green, an image can be displayed using pixels of the four colors.

FIG. 4B illustrates an example in which the red coloring layer 1034R, the green coloring layer 1034G, and the blue coloring layer 1034B are formed between the gate insulating film 1003 and the first interlayer insulating film 1020. As illustrated in FIG. 4B, the coloring layers may be provided between the substrate 1001 and the sealing substrate 1031.

The above-described light-emitting device has a structure in which light is extracted from the substrate 1001 side where the TFTs are formed (a bottom emission structure), but may have a structure in which light is extracted from the sealing substrate 1031 side (a top emission structure).

Structure Example 2 of Light-Emitting Device

Figure 5:
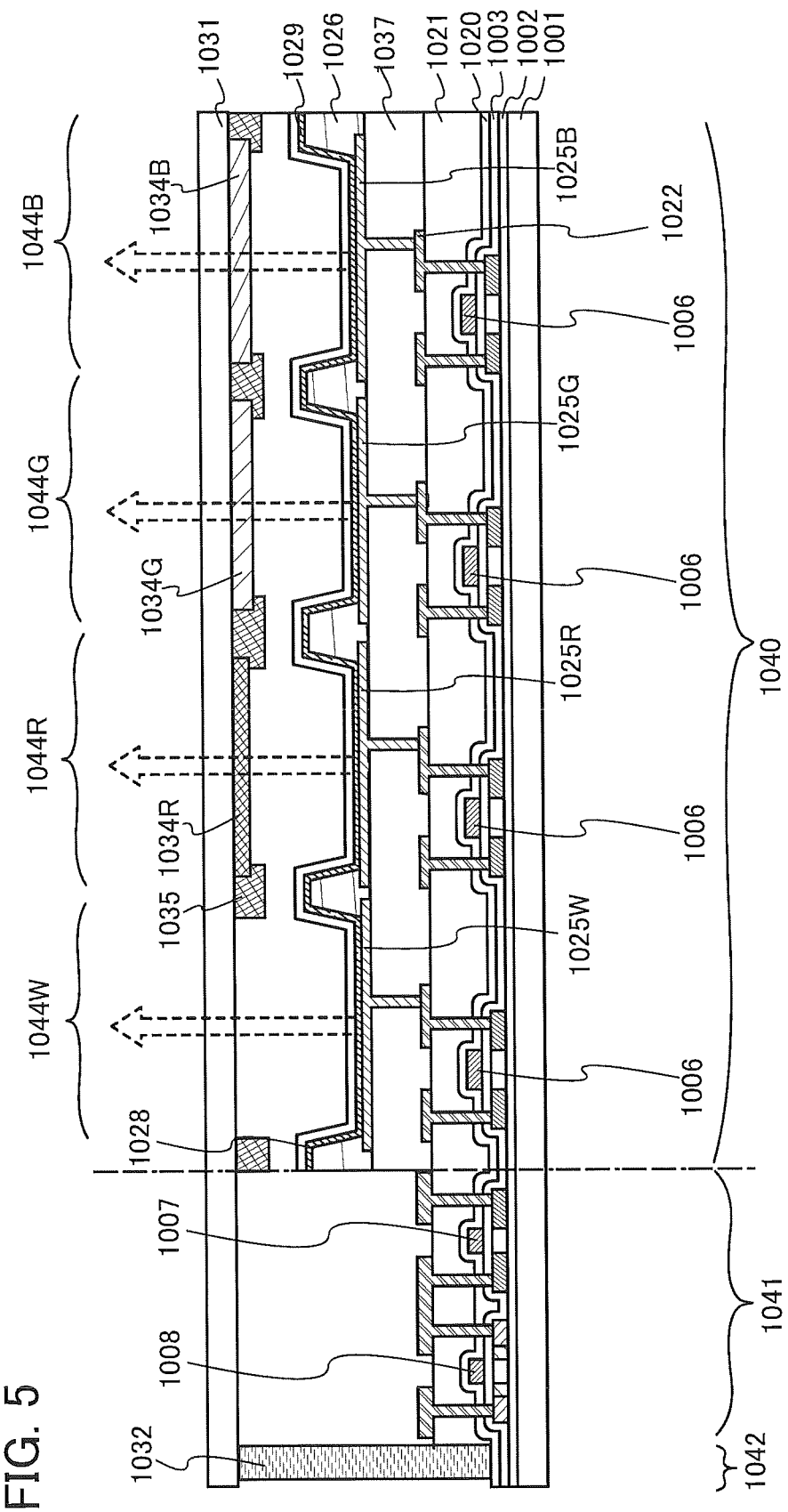
FIG. 5 is a schematic diagram of an active matrix light-emitting device of one embodiment of the present invention.

FIG. 5 is a cross-sectional view of a light-emitting device having a top emission structure. In this case, a substrate that does not transmit light can be used as the substrate 1001. The process up to the step of forming of a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film 1021, or can be formed using any other various materials.

Lower electrodes 1025W, 1025R, 1025G, and 1025B of the light-emitting elements each function as an anode here, but may function as a cathode. Furthermore, in the case of the light-emitting device having a top emission structure as illustrated in FIG. 5, the lower electrodes 1025W, 1025R, 1025G, and 1025B are preferably reflective electrodes. Note that the second electrode 1029 preferably has a function of reflecting light and a function of transmitting light. It is preferable that a microcavity structure be used between the second electrode 1029 and the lower electrodes 1025W, 1025R, 1025G, and 1025B, in which case light having a specific wavelength is amplified. The EL layer 1028 is formed to have a structure similar to the structure described in Embodiments 3 and 4, with which white light emission can be obtained.

In FIGS. 4A and 4B and FIG. 5, the structure of the EL layer for providing whitelight emission can be achieved by, for example, using a plurality of light-emitting layers or using a plurality of light-emitting units. Note that the structure providing white light emission is not limited to the above.

In the case of a top emission structure as illustrated in FIG. 5, sealing can be performed with the sealing substrate 1031 on which the coloring layers (the red coloring layer 1034R, the green coloring layer 1034G, and the blue coloring layer 1034B) are provided. The sealing substrate 1031 may be provided with a black layer (a black matrix) which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

As described above, the light-emitting device including the light-emitting element described in Embodiment 3 and Embodiment 4 can be obtained.

This embodiment can be combined with any of the other embodiments as appropriate.

Embodiment 6

In this embodiment, electronic devices of embodiments of the present invention will be described.

One embodiment of the present invention is a light-emitting element using organic EL and thus, electronic devices with flat surfaces having favorable emission efficiency and high reliability can be manufactured. According to one embodiment of the present invention, electronic devices including curved surfaces and having favorable emission efficiency and high reliability can be manufactured. By including the organic compound of one embodiment of the present invention, the electronic devices can have high emission efficiency and high reliability.

Examples of the electronic devices include a television set, a desktop or laptop personal computer, a monitor of a computer or the like, a digital camera, a digital video camera, a digital photo frame, a mobile phone, a portable game machine, a portable information terminal, an audio reproducing device, and a large game machine such as a pachinko machine.

Figure 6A:
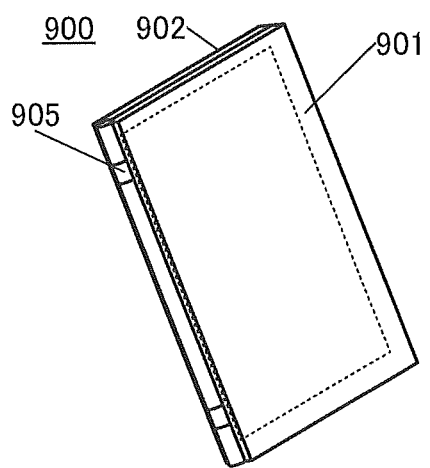
FIGS. 6A to 6D illustrate electronic devices of embodiments of the present invention.
Figure 6B:
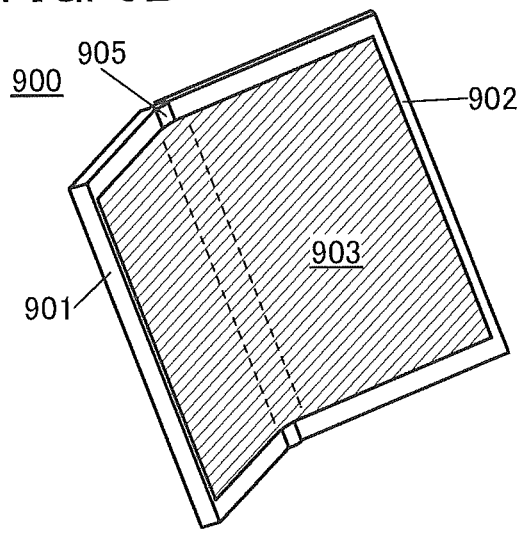

A portable information terminal 900 illustrated in FIGS. 6A and 6B includes a housing 901, a housing 902, a display portion 903, a hinge portion 905, and the like.

The housing 901 and the housing 902 are joined together with the hinge portion 905. The portable information terminal 900 can be opened as illustrated in FIG. 6B from a closed state (FIG. 6A). Thus, the portable information terminal 900 has high portability when carried and excellent visibility when used because of its large display region.

In the portable information terminal 900, the flexible display portion 903 is provided across the housing 901 and the housing 902 which are joined to each other by the hinge portion 905.

The light-emitting device manufactured using one embodiment of the present invention can be used for the display portion 903. Thus, the portable information terminal can have high reliability.

The display portion 903 can display at least one of document data, a still image, a moving image, and the like. When document data is displayed on the display portion, the portable information terminal 900 can be used as an e-book reader.

When the portable information terminal 900 is opened, the display portion 903 is significantly curved. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being bent since pixels are continuously arranged from the housing 901 to the housing 902.

The display portion 903 functions as a touch panel and can be controlled with a finger, a stylus, or the like.

The display portion 903 is preferably formed using one flexible display. Thus, a continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which the housing 901 and the housing 902 become locked (they are not opened any further) is preferably greater than or equal to 90° and less than 180 and can be typically 90°, 120°, 135°, 150°, 175°, or the like. In that case, the convenience, safety, and reliability of the portable information terminal 900 can be improved.

When the hinge portion 905 includes a locking mechanism, excessive force is not applied to the display portion 903; thus, breakage of the display portion 903 can be prevented. Therefore, a highly reliable portable information terminal can be provided.

A power button, an operation button, an external connection port, a speaker, a microphone, or the like may be provided for the housing 901 and the housing 902.

Either of the housing 901 and the housing 902 is provided with a wireless communication module, and data can be transmitted and received through a computer network such as the Internet, a local area network (LAN), or Wi-Fi (registered trademark).

Figure 6C:
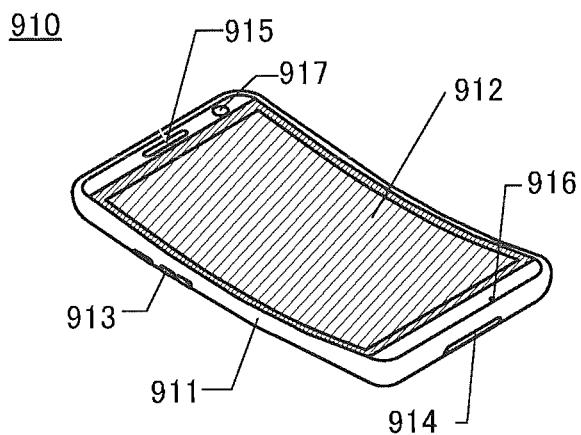

A portable information terminal 910 illustrated in FIG. 6C includes a housing 911, a display portion 912, an operation button 913, an external connection port 914, a speaker 915, a microphone 916, a camera 917, and the like.

The light-emitting device manufactured using one embodiment of the present invention can be used for the display portion 912. Thus, the portable information terminal can be manufactured with high yield.

The portable information terminal 910 includes a touch sensor in the display portion 912. Operations such as making a call and inputting a character can be performed by touch on the display portion 912 with a finger, a stylus, or the like.

With the operation button 913, the power can be turned on or off. In addition, types of images displayed on the display portion 912 can be switched; for example, switching an image from a mail creation screen to a main menu screen is performed with the operation button 913.

When a detection device such as a gyroscope sensor or an acceleration sensor is provided inside the portable information terminal 910, the direction of display on the screen of the display portion 912 can be automatically changed by determining the orientation of the portable information terminal 910 (whether the portable information terminal 910 is placed horizontally or vertically). Furthermore, the direction of display on the screen can be changed by touch on the display portion 912, operation with the operation button 913, sound input using the microphone 916, or the like.

The portable information terminal 910 functions as, for example, one or more of a telephone set, a notebook, and an information browsing system. Specifically, the portable information terminal 910 can be used as a smartphone. The portable information terminal 910 is capable of executing a variety of applications such as mobile phone calls, e-mailing, viewing and editing texts, music reproduction, reproducing a moving image, Internet communication, and computer games, for example.

Figure 6D:
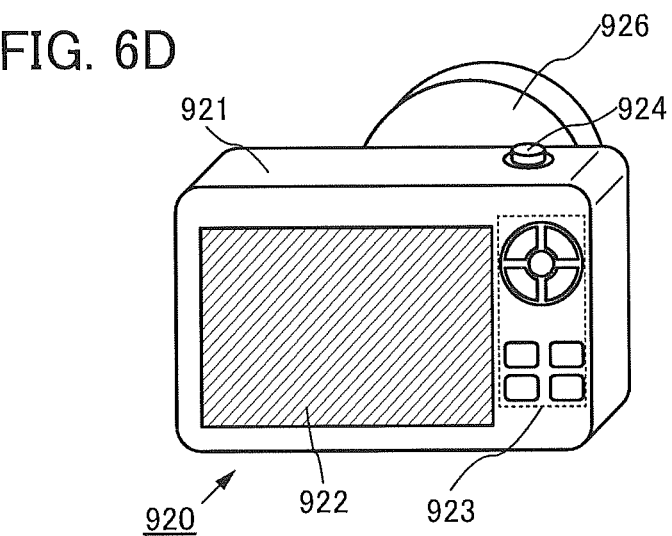

A camera 920 illustrated in FIG. 6D includes a housing 921, a display portion 922, operation buttons 923, a shutter button 924, and the like. Furthermore, an attachable lens 926 is attached to the camera 920.

The light-emitting device manufactured using one embodiment of the present invention can be used for the display portion 922. Thus, the camera can be highly reliable.

Although the lens 926 of the camera 920 here is detachable from the housing 921 for replacement, the lens 926 may be incorporated into the housing 921.

A still image or a moving image can be taken with the camera 920 at the press of the shutter button 924. In addition, images can also be taken by the touch of the display portion 922 which has a function of a touch panel.

Note that a stroboscope, a viewfinder, or the like can be additionally attached to the camera 920. Alternatively, these may be incorporated into the housing 921.

Figure 7A:
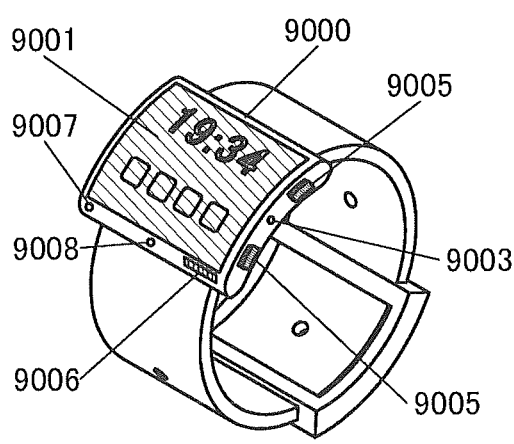
FIGS. 7A to 7E illustrate electronic devices of embodiments of the present invention.
Figure 7B:
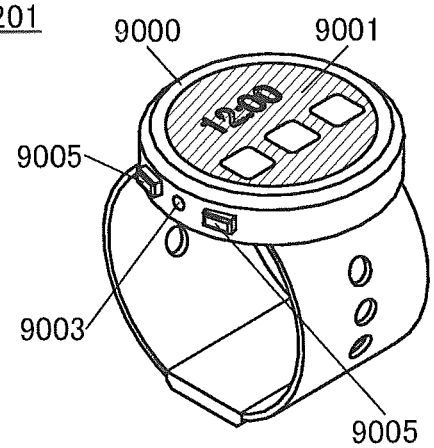

FIG. 7A is a perspective view of a watch-type portable information terminal 9200. FIG. 7B is a perspective view of a watch-type portable information terminal 9201.

The portable information terminal 9200 illustrated in FIG. 7A is capable of executing a variety of applications such as mobile phone calls, e-mailing, viewing and editing texts, music reproduction, Internet communication, and computer games. The display surface of the display portion 9001 is bent, and an image can be displayed on the bent display surface. The portable information terminal 9200 can employ near field communication conformable to a communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is also possible. Note that the charging operation may be performed by wireless power feeding without using the connection terminal 9006.

Unlike in the portable information terminal illustrated in FIG. 7A, the display surface of the display portion 9001 is not curved in the portable information terminal 9201 illustrated in FIG. 7B. Furthermore, the external state of the display portion of the portable information terminal 9201 is a non-rectangular shape (a circular shape in FIG. 7B).

Figure 7C:
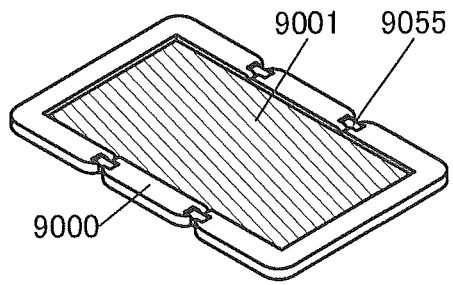
Figure 7D:
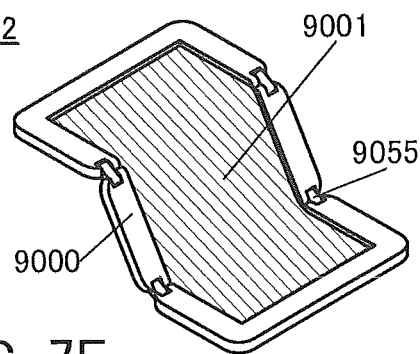
Figure 7E:
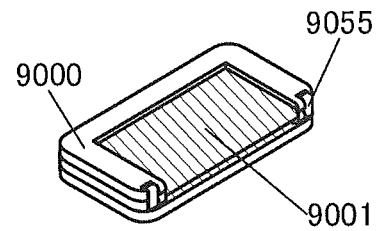

FIGS. 7C to 7E are perspective views of a foldable portable information terminal 9202. FIG. 7C is a perspective view illustrating the portable information terminal 9202 that is opened. FIG. 7D is a perspective view illustrating the portable information terminal 9202 that is being opened or being folded. FIG. 7E is a perspective view illustrating the portable information terminal 9202 that is folded.

The folded portable information terminal 9202 is highly portable, and the opened portable information terminal 9202 is highly browsable due to a seamless large display region. The display portion 9001 of the portable information terminal 9202 is supported by three housings 9000 joined together by hinges 9055. By folding the portable information terminal 9202 at a connection portion between two housings 9000 with the hinges 9055, the portable information terminal 9202 can be reversibly changed in shape from opened to folded. For example, the portable information terminal 9202 can be bent with a radius of curvature of greater than or equal to 1 mm and less than or equal to 150 mm.

Figure 8A:
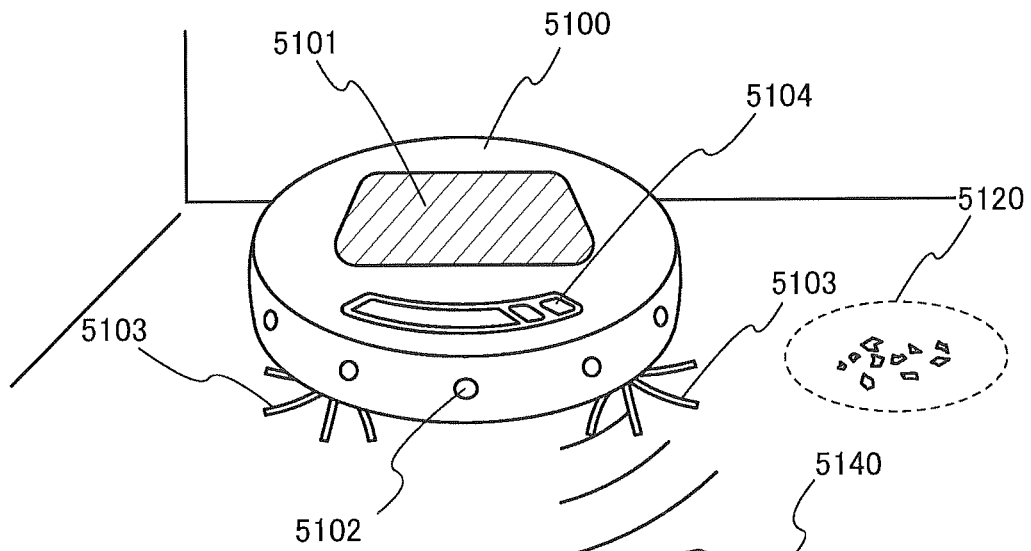
FIGS. 8A to 8C illustrate electronic devices of embodiments of the present invention.

FIG. 8A is a schematic view illustrating an example of a cleaning robot.

A cleaning robot 5100 includes a display 5101 on its top surface, a plurality of cameras 5102 on its side surface, a brush 5103, and an operation button 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. The cleaning robot 5100 has a radio communication means.

The cleaning robot 5100 is self-propelled, detects dust 5120, and vacuums the dust from the inlet provided on the bottom surface.

The cleaning robot 5100 can judge whether or not there is an obstacle such as a wall, furniture, or a step by analyzing an image taken by the cameras 5102. In the case where the cleaning robot 5100 detects an object that is likely to be caught in the brush 5103, such as a wiring, by analyzing an image, the rotation of the brush 5103 can be stopped.

The display 5101 can display the remaining capacity of a battery, the amount of vacuumed dust, and the like. The display 5101 may display a path in which the cleaning robot 5100 has run. The display 5101 may be a touch panel and the operation button 5104 may be provided on the display 5101.

The cleaning robot 5100 can communicate with a portable electronic device 5140 such as a smartphone. The portable electronic device 5140 can display an image taken by the cameras 5102. Therefore, an owner of the cleaning robot 5100 can monitor his/her room even from the outside. The owner can also check the display on the display 5101 by the portable electronic device 5140 such as a smartphone.

The light-emitting device of one embodiment of the present invention can be used for the display 5101.

Figure 8B:
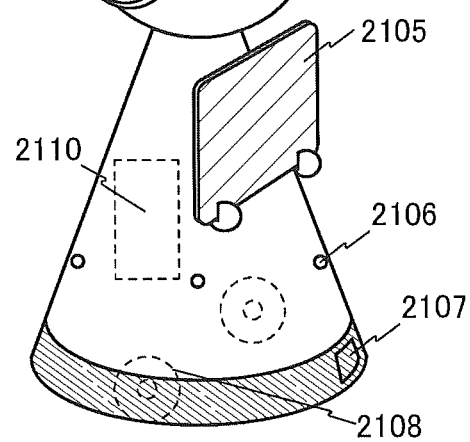

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. The display 2105 may be a detachable information terminal, in which case the display can be charged and transmit and receive data when in the home position of the robot 2100.

The upper camera 2103 and the lower camera 2106 each have a function of capturing an image of the surroundings of the robot 2100. The obstacle sensor 2107 can detect an obstacle in the direction where the robot 2100 advances with the moving mechanism 2108. The robot 2100 can move safely by recognizing an ambient environment with the upper camera 2103, the lower camera 2106, and the obstacle sensor 2107.

The light-emitting device of one embodiment of the present invention can be used for the display 2105.

Figure 8C:
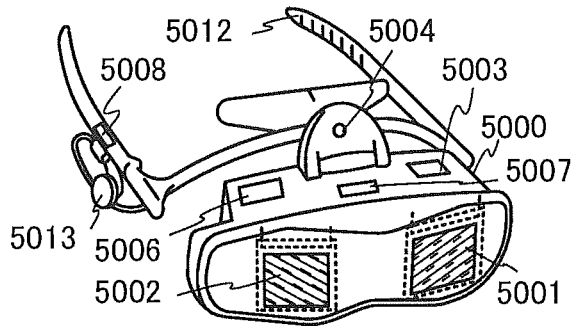

FIG. 8C illustrates an example of a goggle-type display. The goggle-type display includes, for example, a housing 5000, a display portion 5001, a speaker 5003, an LED lamp 5004, operation keys 5005 (including a power switch and an operation switch), a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, a second display portion 5002, a support 5012, an earphone 5013, and the like.

The light-emitting device of one embodiment of the present invention can be used for the display portion 5001 and the second display portion 5002.

Figure 9A:
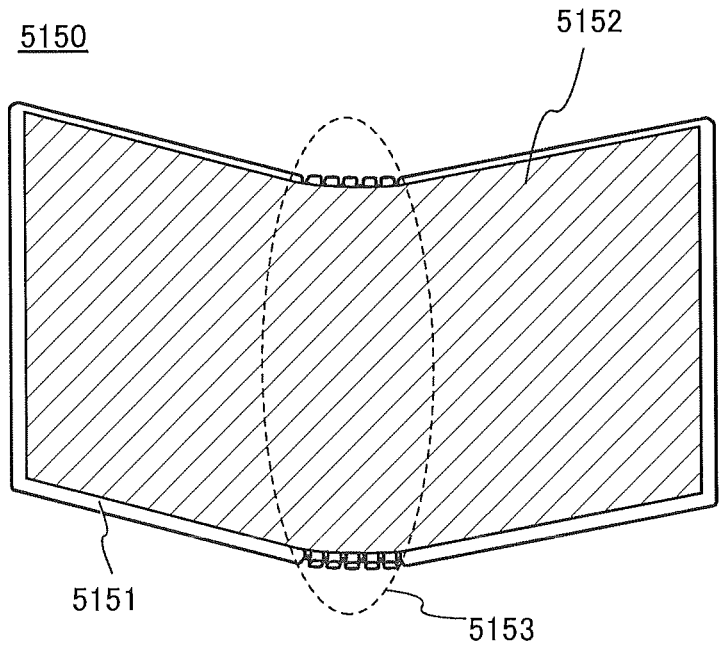
FIGS. 9A and 9B illustrate electronic devices of embodiments of the present invention.
Figure 9B:
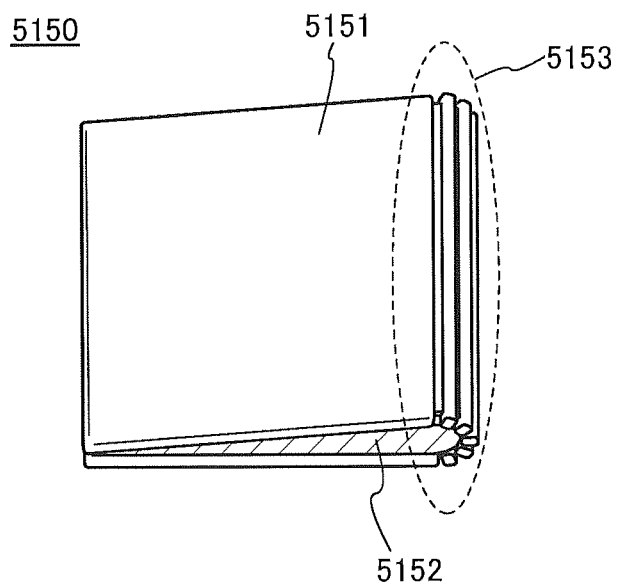

FIGS. 9A and 9B illustrate a foldable portable information terminal 5150. The foldable portable information terminal 5150 includes a housing 5151, a display region 5152, and a bend portion 5153. FIG. 9A illustrates the portable information terminal 5150 that is opened. FIG. 9B illustrates the portable information terminal 5150 that is folded. Despite its large display region 5152, the portable information terminal 5150 is compact in size and has excellent mobility when folded.

The display region 5152 can be folded in half with the bend portion 5153. The bend portion 5153 includes a flexible member and a plurality of supporting members. When the display region is folded, the flexible member expands and the bend portion 5153 has a radius of curvature of 2 mm or more, preferably 5 mm or more.

Note that the display region 5152 may be a touch panel (an input/output device) including a touch sensor (an input device). The light-emitting device of one embodiment of the present invention can be used for the display region 5152.

Note that this embodiment can be combined with any of the other embodiments as appropriate.

Embodiment 7

In this embodiment, examples in which the light-emitting element of one embodiment of the present invention is used for various lighting devices will be described with reference to FIGS. 10A to 10C and FIG. 11. With the use of the light-emitting element of one embodiment of the present invention, a highly reliable lighting device with favorable emission efficiency can be manufactured.

An electronic device or a lighting device that has a light-emitting region with a curved surface can be obtained with use of the light-emitting element of one embodiment of the present invention which is fabricated over a substrate having flexibility.

Furthermore, a light-emitting device in which the light-emitting element of one embodiment of the present invention is used can also be used for lighting for motor vehicles, examples of which are lighting for a windshield, a ceiling, and the like.

Figure 10A:
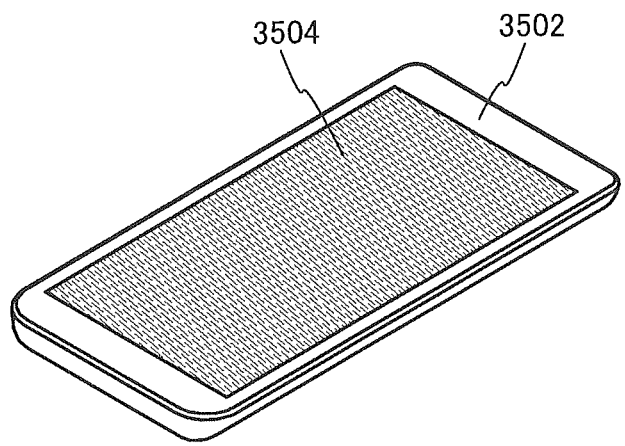
FIGS. 10A to 10C illustrate lighting devices of embodiments of the present invention.
Figure 10B:
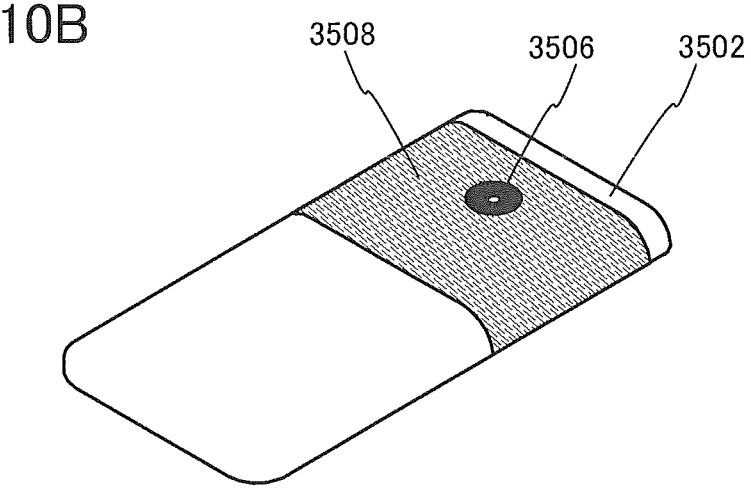

FIG. 10A is a perspective view illustrating one surface of a multifunction terminal 3500, and FIG. 10B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 10A and 10B can have a variety of functions as in the electronic devices illustrated in FIGS. 7A to 7C.

The housing 3502 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. When a detection device including a sensor for detecting inclination, such as a gyroscope sensor or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 10C:
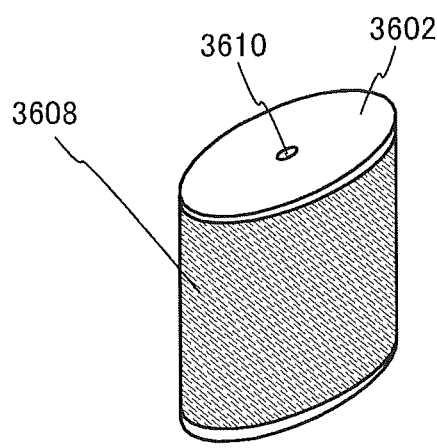

FIG. 10C is a perspective view of a security light 3600. The light 3600 includes lighting 3608 on the outside of the housing 3602, and a speaker 3610 and the like are incorporated in the housing 3602. The light-emitting element of one embodiment of the present invention can be used for the lighting 3608.

The light 3600 emits light when the lighting 3608 is gripped or held, for example. An electronic circuit that can control the manner of light emission from the light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The light 3600 can emit light in various directions; therefore, it is possible to intimidate a thug or the like with light, or light and sound. Moreover, the light 3600 may include a camera such as a digital still camera to have a photography function.

Figure 11:
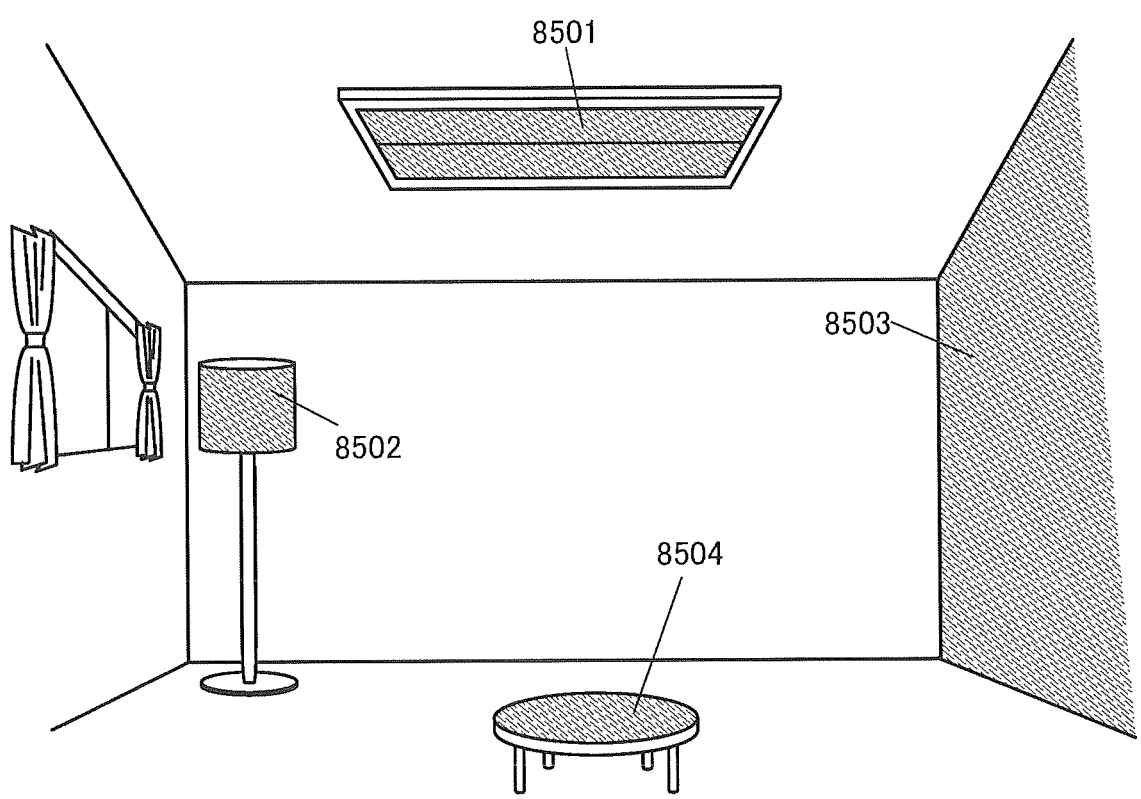
FIG. 11 illustrates lighting devices of embodiments of the present invention.

FIG. 11 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function of a table can be obtained. When the light-emitting element is used as part of other furniture, a lighting device which has a function as the furniture can be obtained.

As described above, lighting devices and electronic devices can be obtained by application of the light-emitting element of one embodiment of the present invention. Note that the light-emitting element can be used for lighting devices and electronic devices in a variety of fields without being limited to the lighting devices and the electronic devices described in this embodiment.

The structure described above in this embodiment can be combined with any of the structures described in the other embodiments as appropriate.

Example 1

In this example, a method for synthesizing 2,8-bis[3-(dibenzothiophen-4-yl)phenyl]-4-phenyl-[1]benzofuro[3,2-d]pyrimidine (abbreviation: 4Ph-2,8mDBtP2Bfpm) (Structural Formula (100)), which is a compound of one embodiment of the present invention represented by General Formula (G0), and the characteristics of this compound are described.

Synthesis Example 1

Step 1: Synthesis of 2,4,5-trichloro-6-(5-chloro-2-methoxyphenyl)pyrimidine

Into a 1-L three-neck flask were put 26 g (121 mmol) of 2,4,5,6-tetrachloropyrimidine, 15 g (81 mmol) of 5-chloro- 2-methoxyphenylboronic acid, 34 g (161 mmol) of tripotassium phosphate, 320 mL of acetonitrile, and 80 mL of water, and the flask was degassed and the air therein was replaced with nitrogen. To this mixture were added 2.1 g (8.0 mmol) of triphenylphosphine and 0.90 g (4 mmol) of palladium acetate, and stirring was performed for 16 hours at room temperature. After the predetermined time elapsed, the resulting reaction mixture was subjected to suction filtration and the filtrate was separated into an aqueous layer and an organic layer; then, the aqueous layer was subjected to extraction with toluene. The organic layer and the obtained solution of the extract were combined, washed with saturated brine, and dried by adding anhydrous magnesium sulfate. This mixture was subjected to gravity filtration, and the filtrate was concentrated to give a solid. This solid was purified by flash column chromatography. A mixed solvent of toluene and hexane in a ratio of 1:1 was used as a developing solvent, and the ratio of toluene to hexane was gradually changed to 5:1 during the purification. The obtained fraction was concentrated to give 15 g of a white solid, which was an objective substance, in a yield of 57%. The synthesis scheme of Step 1 is shown in Synthesis Scheme (A-1) below. Note that this step was performed twice.

[Chemical Formulae 30]

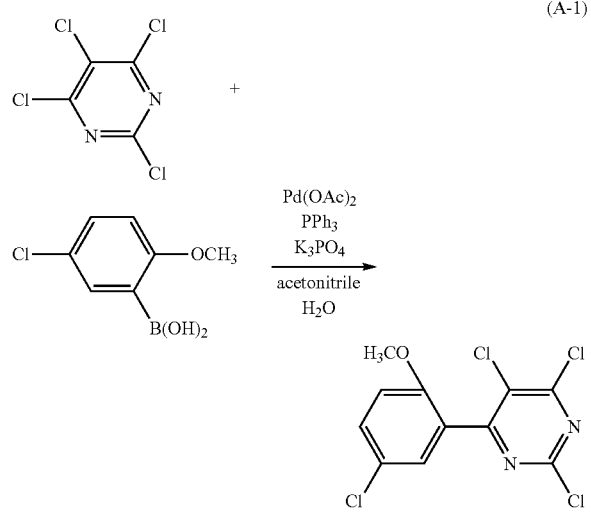

Step 2: Synthesis of
4-chloro-2-(2,5,6-trichloropyrimidin-4-yl)phenol

Into a 1-L three-neck flask were put 16 g (49 mmol) of 2,4,5-trichloro-6-(5-chloro-2-methoxyphenyl)pyrimidine obtained in Step 1 and 180 mL of dichloromethane, and this mixture was cooled down in an ice bath. To the mixture was added dropwise 100 mL of boron tribromide (a 1 mol/L dichloromethane solution), and stirring was performed for 24 hours while the temperature was raised to room temperature. After the predetermined time elapsed, the reaction mixture was poured into 300 mL of water and stirring was performed for 1 hour at room temperature. To the resulting mixture was added 270 mL of a saturated aqueous solution of sodium hydrogencarbonate for neutralization. An aqueous layer and an organic layer were separated, and the aqueous layer was subjected to extraction with dichloromethane. A mixed solution of the organic layer and the solution of the extract was washed with a sodium thiosulfate aqueous solution and saturated brine in this order, and dried by adding anhydrous magnesium sulfate to the mixed solution. The resulting mixture was subjected to gravity filtration and the filtrate was concentrated to give 14 g of a yellow solid, which was an objective substance, in a yield of 91%. The synthesis scheme of Step 2 is shown in the following formula (A-2).

[Chemical Formulae 31]

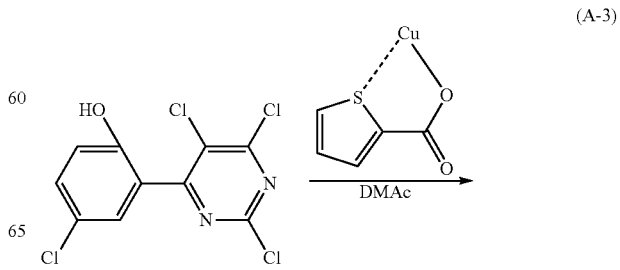

Step 3: Synthesis of 2,4,8-trichloro-[1]benzofuro[3,2-d]pyrimidine

Into a 1-L three-neck flask were put 12 g (38 mmol) of 4-chloro-2-(2,5,6-trichloropyrimidin-4-yl)phenol obtained in Step 2 above and 370 mL of dimethylacetamide (DMAc), and the air in the flask was replaced with argon. To this mixture was added 7.9 g (41 mmol) of copper 2-thiophenecarboxylate, and irradiation with microwaves was performed at 400 W and 140° C. for 20 minutes to cause a reaction. After the predetermined time elapsed, 600 mL of 0.5 M hydrochloric acid was added to the obtained reaction mixture, and an aqueous layer was subjected to extraction with dichloromethane. The obtained solution of the extract was washed with water, a saturated aqueous solution of sodium hydrogencarbonate, and saturated brine in this order, and dried by adding anhydrous magnesium sulfate. The obtained mixture was gravity-filtered, and the filtrate was concentrated to give an oily substance. This oily substance was purified by flash column chromatography. As the developing solvent, a mixed solvent of dichloromethane and hexane in a ratio of 1:1 was used. The obtained fraction was concentrated to give 1.5 g of a white solid, which was an objective substance, in a yield of 15%. The synthesis scheme of Step 3 is shown in the following formula (A-3).

[Chemical Formulae 32]

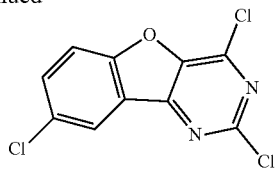

Step 4: Synthesis of 2,8-dichloro-4-phenyl-[1]benzofuro[3,2-d]pyrimidine

Into a 100-mL round-bottom flask were put 1.5 g (5.5 mmol) of 2,4,8-trichloro-[1]benzofuro[3,2-d]pyrimidine obtained in Step 3 above, 0.68 g (5.5 mmol) of phenylboronic acid, 20 mL of acetonitrile, and 20 mL of water, and the air in the flask was replaced with argon. To this mixture was added 0.18 mg (0.25 mmol) of bis(triphenylphosphine)palladium(II) dichloride, and irradiation with microwaves was performed at 100 W and 65° C. for 1 hour. After the predetermined time elapsed, 34 mg (0.05 mmol) of bis(triphenylphosphine)palladium(II) dichloride was further added, and irradiation with microwaves was performed at 100 W and 65° C. for 30 minutes. After the predetermined time elapsed, the precipitated solid was subjected to suction filtration and washed with water and ethanol in this order. The obtained solid was purified by silica gel column chromatography. As a developing solvent, a mixed solvent of toluene and hexane in a ratio of 1:1 was used. The obtained fraction was concentrated to give a white solid. This solid was washed with hexane to give 1.2 g of a white solid, which was an objective substance, in a yield of 67%. The synthesis scheme of Step 4 is shown in the following formula (A-4).

[Chemical Formulae 33]

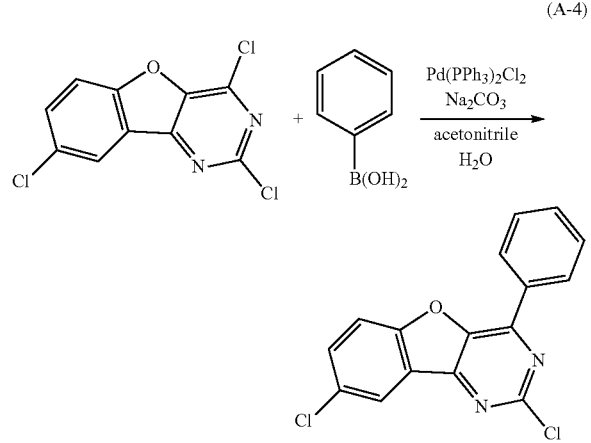

(A-4)

Step 5: Synthesis of 4Ph-2,8mDBtP2Bfpm

Into a three-neck flask were put 0.42 g (1.3 mmol) of 2,8-dichloro-4-phenyl-[1]benzofuro[3,2-d]pyrimidine obtained in Step 4, 0.93 g (3.0 mmol) of 3-(dibenzothiophen-4-yl)phenylboronic acid, 1.9 g (9.0 mmol) of tripotassium phosphate, 15 mL of diglyme, and 0.67 g (9.0 mmol) of tert-butanol, and the air in the flask was replaced with nitrogen. The mixture was heated to 60° C., 12 mg (0.053 mmol) of palladium(II) acetate and 38 mg (0.11 mmol) of di(1-adamantyl)-n-butylphosphine, and stirring was performed for 6 hours at 140° C. Water was added to the resulting reaction mixture and the precipitated solid was subjected to suction filtration and washed with water and ethanol in this order. The resulting solid was dissolved in toluene and suction-filtered through Celite and alumina stacked in this order. A solid obtained by concentrating the resulting filtrate was purified by silica gel column chromatography. As a developing solvent, a mixed solvent of toluene and hexane in a ratio of 1:1 was used. The obtained fraction was concentrated to give a solid. This solid was recrystallized from toluene/ethanol to give 0.52 g of a white powder, which was an objective substance, in a yield of 52%. A synthesis scheme of Step 5 is shown in the following formula (A-5).

[Chemical Formulae 34]

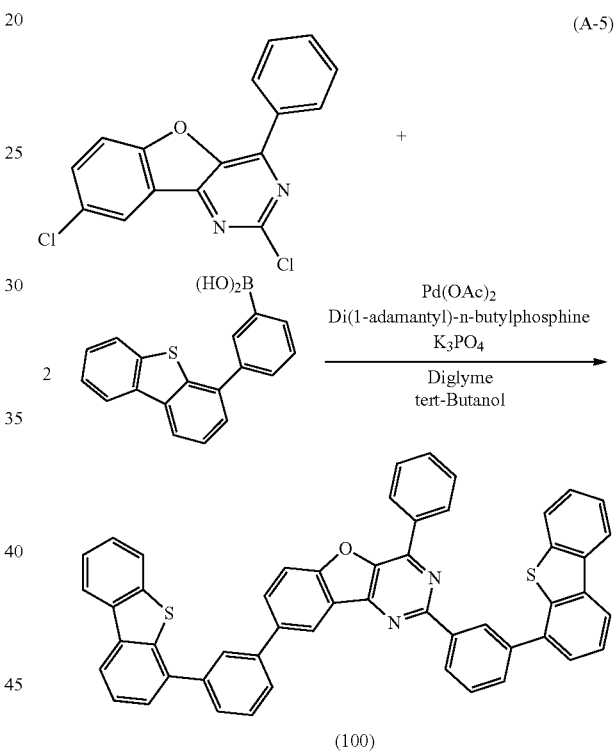

(A-5)

The obtained solid was subjected to analysis by nuclear magnetic resonance spectrometry ($^1$H NMR), and the results are shown below.

$^1$H-NMR δ (CDCl$_3$): 7.44-7.51 (m, 4H), 7.58-7.68 (m, 8H), 7.72 (t, 1H), 7.78-7.86 (m, 5H), 7.90 (d, 1H), 8.07 (dd, 1H), 8.11 (st, 1H), 8.18-8.24 (m, 4H), 8.67 (sd, 1H), 8.79-8.82 (m, 3H), 9.12 (st, 1H).

Figure 12A:
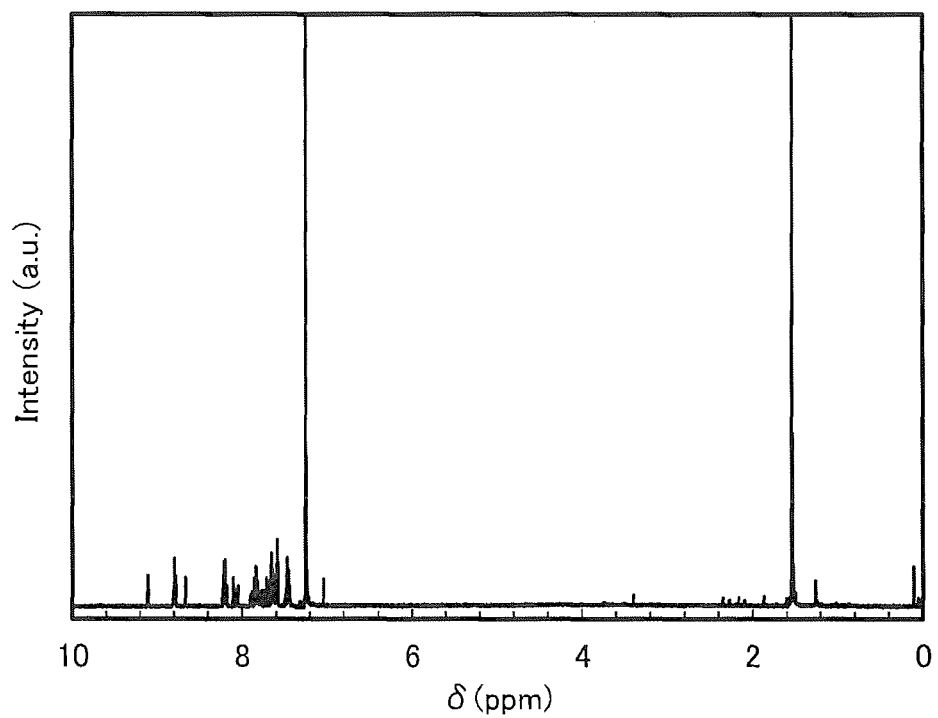
FIGS. 12A and 12B show NMR charts of a compound in Example.
Figure 12B:
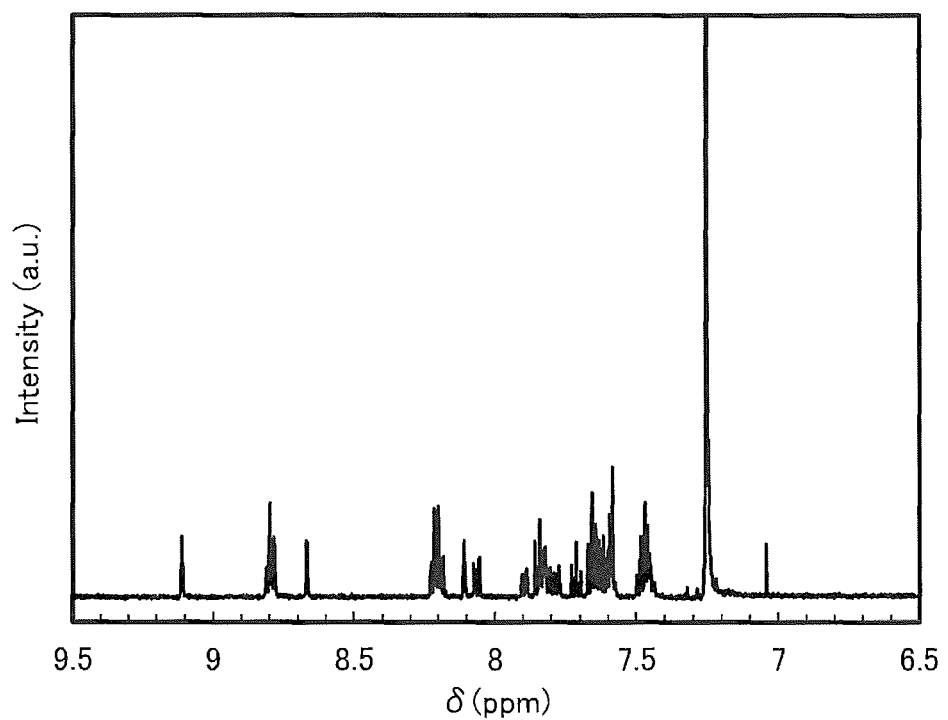

FIGS. 12A and 12B are $^1$H NMR charts of the obtained solid. Note that FIG. 12B is a chart showing an enlarged part in the range of 6.5 ppm to 9.5 ppm of FIG. 12A. The measurement results indicate that 4Ph-2,8mDBtP2Bfpm, which was the objective substance, was obtained.

<Characteristics of 4Ph-2,8mDBtP2Bfpm>

Figure 13:
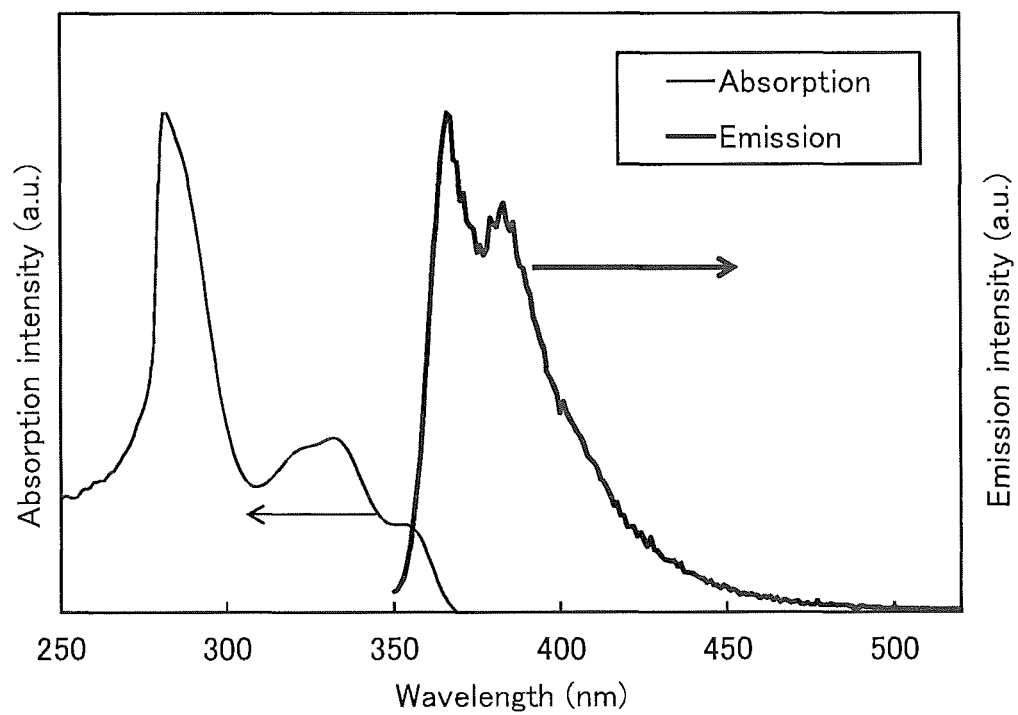
FIG. 13 shows absorption and emission spectra of a compound in Example.

Then, the ultraviolet-visible absorption spectrum (hereinafter, simply referred to as "absorption spectrum") and emission spectrum of a toluene solution of 4Ph-2,8mDBtP2Bfpm were measured. The absorption spectrum was measured with an ultraviolet-visible spectrophotometer (V-550, produced by JASCO Corporation). The emission spectrum was measured with a fluorescence spectrophotometer (FS920 produced by Hamamatsu Photonics K.K.). FIG. 13 shows the measurement results of the absorption and emission spectra of the toluene solution. The horizontal axis represents wavelength and the vertical axes represent absorption intensity and emission intensity.

FIG. 13 shows that the toluene solution of 4Ph-2,8mDBtP2Bfpm has absorption peaks at around 333 nm and 356 nm, and an emission peak at around 366 nm. It was suggested that 4Ph-2,8mDBtP2Bfpm, which is one embodiment of the present invention, has a high S1 level and thus can be suitably used as a host material of a light-emitting element.

Next, the HOMO level and the LUMO level of 4Ph-2,8mDBtP2Bfpm were calculated by cyclic voltammetry (CV) measurement. The calculation method is shown below.

An electrochemical analyzer (ALS model 600A or 600C, manufactured by BAS Inc.) was used as a measurement apparatus. A solution for the CV measurement was prepared in the following manner: tetra-n-butylammonium perchlorate (n-Bu$_4$NClO$_4$; produced by Tokyo Chemical Industry Co., Ltd., catalog No. T0836) as a supporting electrolyte was dissolved in dehydrated dimethylformamide (DMF; produced by Sigma-Aldrich Inc., 99.8%, catalog No. 22705-6) as a solvent at a concentration of 100 mmol/L; and the object to be measured was dissolved therein at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (20° C. to 25° C.). In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

The CV measurement was repeated 100 times, and the oxidation-reduction wave in the hundredth cycle was compared with the oxidation-reduction wave in the first cycle to examine the electrical stability of the compound.

According to the results, 4Ph-2,8mDBtP2Bfpm has a HOMO level of −6.16 eV and a LUMO level of −2.99 eV. When the oxidation-reduction wave was repeatedly measured, in the oxidation potential Ea [V] measurement, the peak intensity of the oxidation-reduction wave after the hundredth cycle was maintained to be 88% of that of the oxidation-reduction wave at the first cycle; accordingly, 4Ph-2,8mDBtP2Bfpm is highly resistant to oxidation.

Example 2

In this example, fabrication examples of a light-emitting element including the organic compound of one embodiment of the present invention and a comparative light-emitting element and the characteristics of the light-emitting elements are described. FIG. 1A illustrates a stacked-layer structure of the light-emitting elements fabricated in this example. Table 1 shows details of the element structures. The organic compounds used in this example are shown below. Note that Embodiments or the other Example can be referred to for other organic compounds.

[Chemical Formulae 35]

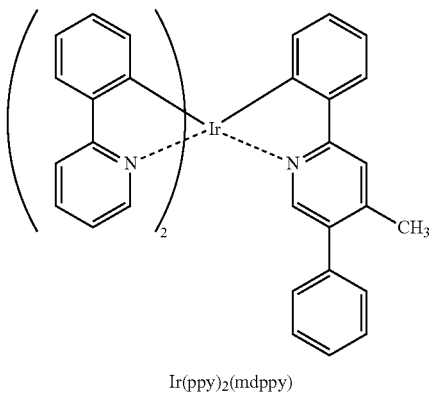

Ir(ppy)$_2$(mdppy)

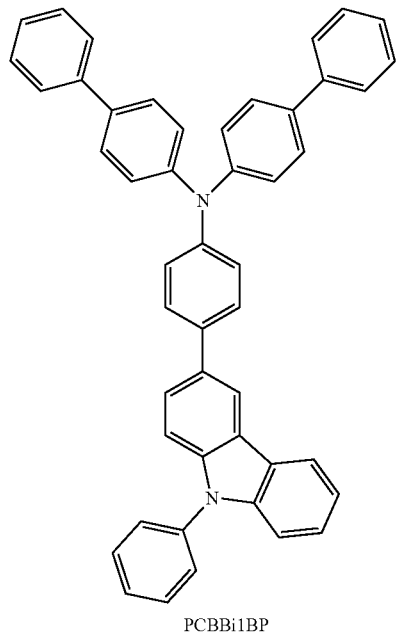

PCBBi1BP

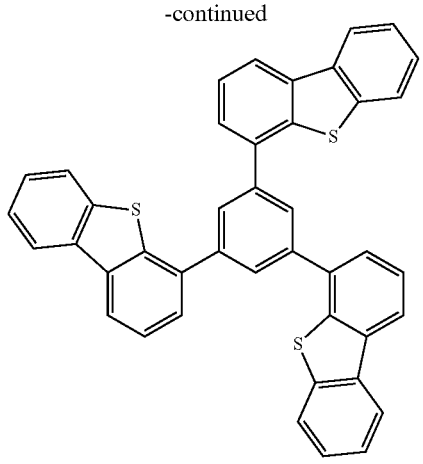

DBT3P-II

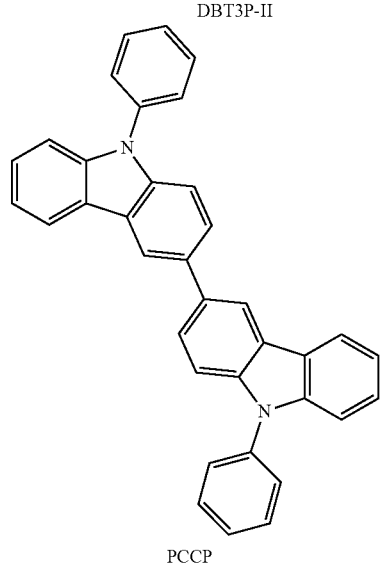

PCCP

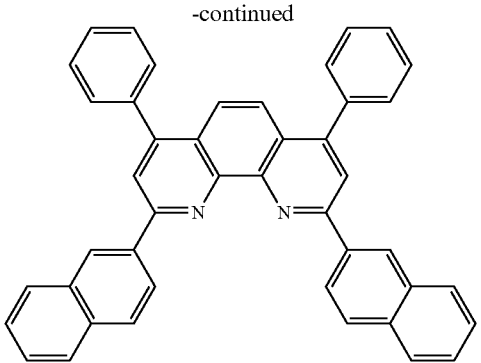

NBPhen

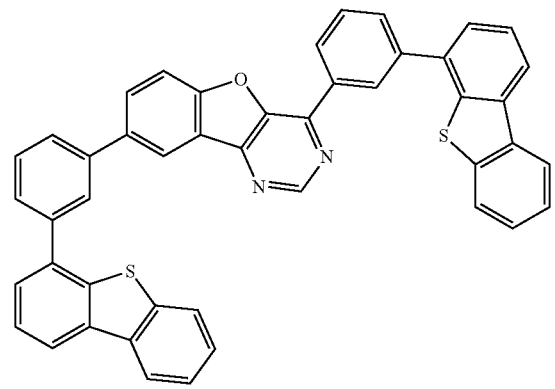

4,8mDBtP2Bfpm

TABLE 1

|  | Layer | Reference numeral | Thickness (nm) | Material(s) | Weight ratio |
|---|---|---|---|---|---|
| Light-emitting element 1 | Electrode | 102 | 200 | Al | — |
|  | Electron-injection layer | 119 | 1 | LiF | — |
|  | Electron-transport layer | 118(2) | 15 | NBPhen | — |
|  |  | 118(1) | 20 | 4Ph-2,8mDBtP2Bfpm | — |
|  | Light-emitting layer | 140 | 40 | 4Ph-2,8mDBtP2Bfpm:PCCP:Ir(ppy)$_2$(mdppy) | 0.6:0.4:0.1 |
|  | Hole-transport layer | 112 | 20 | PCBBiIBP | — |
|  | Hole-injection layer | 111 | 45 | DBT3P-II:MoO$_3$ | 1:0.5 |
|  | Electrode | 101 | 70 | ITSO | — |
| Comparative light-emitting element 2 | Electrode | 102 | 200 | Al | — |
|  | Electron-injection layer | 119 | 1 | LiF | — |
|  | Electron-transport layer | 118(2) | 15 | NBPhen | — |
|  |  | 118(1) | 20 | 4,8mDBtP2Bfpm | — |
|  | Light-emitting layer | 140 | 40 | 4,8mDBtP2Bfpm:PCCP:Ir(ppy)$_2$(mdppy) | 0.6:0.4:0.1 |
|  | Hole-transport layer | 112 | 20 | PCBBiIBP | — |
|  | Hole-injection layer | 111 | 45 | DBT3P-II:MoO$_3$ | 1:0.5 |
|  | Electrode | 101 | 70 | ITSO | — |

<<Fabrication of Light-Emitting Element 1>>

As the electrode 101, an ITSO film was formed to a thickness of 70 nm over a glass substrate by a sputtering method. Note that the electrode area of the electrode 101 was set to 4 mm² (2 mm×2 mm). Next, in pretreatment for forming the light-emitting element over the substrate, a surface of the substrate was washed with water and dried at 200° C. for 1 hour, and then UV ozone treatment was performed for 370 seconds. After that, the substrate was transferred into a vacuum evaporation apparatus where a degree of vacuum was kept at approximately $1\times10^{-4}$ Pa, and baking was performed at 170° C. for 30 minutes. Then, the substrate was allowed to cool for approximately 30 minutes.

As the hole-injection layer 111, DBT3P-II and molybdenum oxide ($MoO_3$) were deposited over the electrode 101 by co-evaporation in a weight ratio of DBT3P-II: $MoO_3$=1:0.5 to a thickness of 45 nm.

Next, as the hole-transport layer 112, PCBBi1BP was deposited over the hole-injection layer 111 by evaporation to a thickness of 20 nm.

Next, as the light-emitting layer 140 over the hole-transport layer 112, 4Ph-2,8mDBtP2Bfpm, PCCP, and [2-(4-methyl-5-phenyl-2-pyridinyl-κN)phenyl-κC]bis[2-(2-pyridinyl-1N)phenyl-κC]iridium(III) (abbreviation: Ir(ppy)$_2$(mdppy)) were deposited by co-evaporation in a weight ratio of 4Ph-2,8mDBtP2Bfpm: PCCP: Ir(ppy)$_2$(mdppy)=0.6:0.4:0.1 to a thickness of 40 nm. Note that in the light-emitting layer 140, Ir(ppy)$_2$(mdppy) is a guest material that emits phosphorescence.

Next, as an electron-transport layer 118(1), 4Ph-2,8mDBtP2Bfpm was deposited over the light-emitting layer 140 by evaporation to a thickness of 20 nm. Next, as an electron-transport layer 118(2), NBPhen was deposited over the electron-transport layer 118(1) by evaporation to a thickness of 15 nm.

Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, the glass substrate over which the light-emitting element 1 was formed was fixed to a substrate (a counter substrate) with a sealant, whereby the light-emitting element 1 was sealed. Specifically, a drying agent was attached to the counter substrate, the sealant was applied to the counter substrate so as to surround the light-emitting element, and the counter substrate and the glass substrate over which the light-emitting element was formed were bonded to each other. Then, irradiation with ultraviolet light having a wavelength of 365 nm at 6 J/cm² and heat treatment at 80° C. for 1 hour were performed. Through the above steps, the light-emitting element 1 was fabricated.

<<Fabrication of Comparative Light-Emitting Element 2>>

The fabrication process of the comparative light-emitting element 2 is the same as that of the light-emitting element 1 described above except for the fabrication steps of the light-emitting layer 140 and the electron-transport layer 118 and is thus not described in detail here. FIG. 1A and Table 1 can be referred to for the details of the element structure.

Note that the light-emitting element 1 of one embodiment of the present invention uses the organic compound of one embodiment of the present invention which includes a benzofuro[3,2-d]pyrimidine skeleton and in which the 2-position of the skeleton has a substituent and the benzene ring side (the 6- to 9-positions) of the skeleton has at least one substituent. The comparative light-emitting element 2 uses the organic compound which includes a benzofuro[3,2-d]pyrimidine skeleton and in which the 4-position of the skeleton has a substituent and the benzene ring side (the 6- to 9-positions) of the skeleton has at least one substituent.

<Characteristics of Light-Emitting Elements>

Next, the characteristics of the fabricated light-emitting element 1 and comparative light-emitting element 2 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 14:
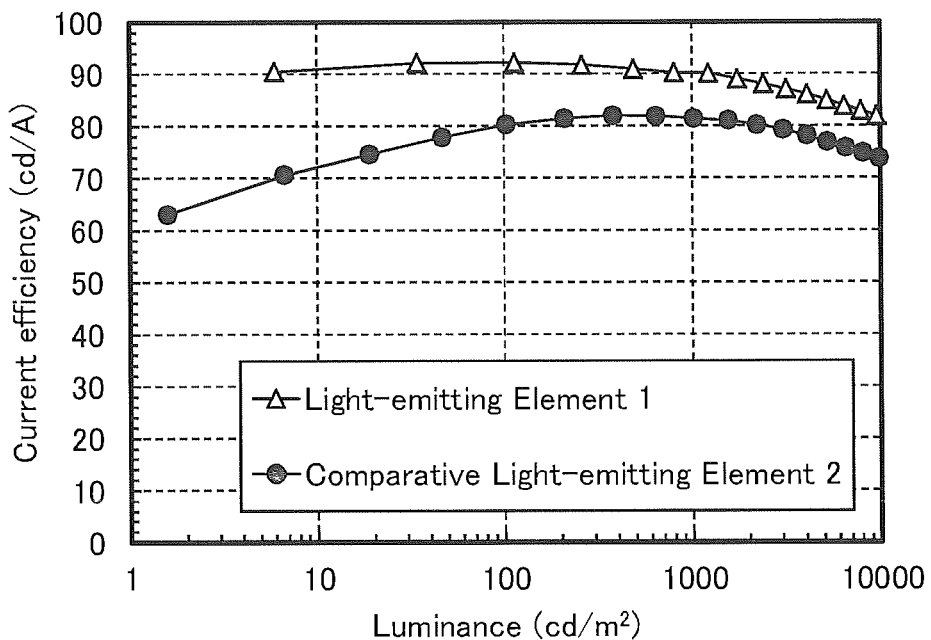
FIG. 14 shows luminance-current efficiency characteristics of light-emitting elements in Example.
Figure 15:
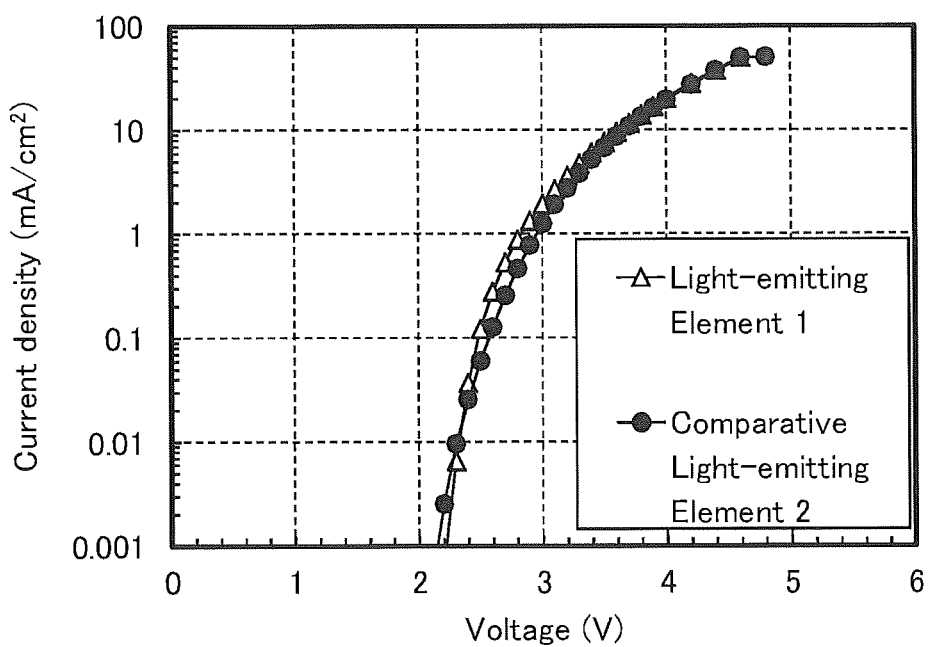
FIG. 15 shows voltage-current density characteristics of light-emitting elements in Example.
Figure 16:
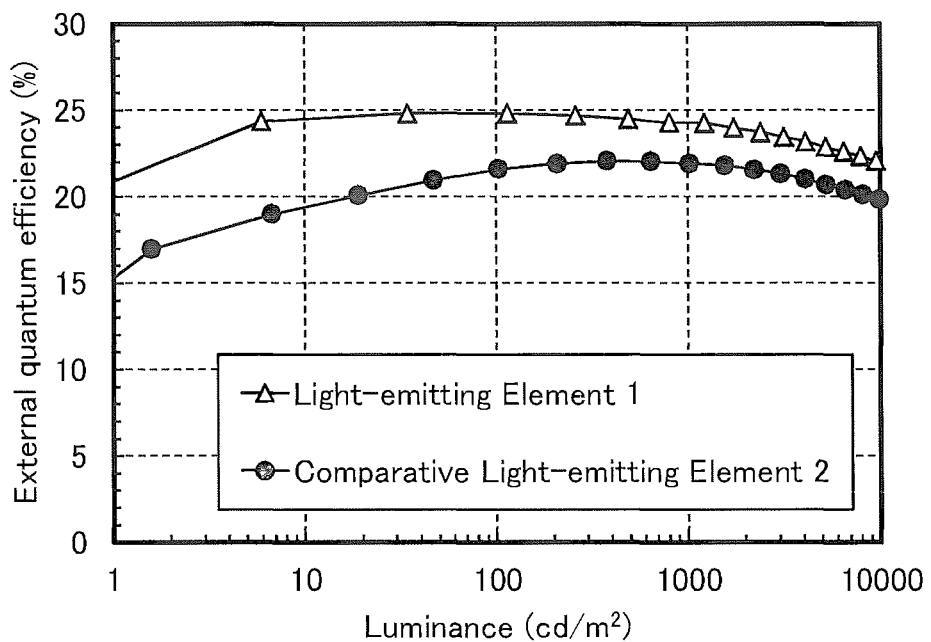
FIG. 16 shows luminance-external quantum efficiency characteristics of light-emitting elements in Example.

FIG. 14 shows luminance-current efficiency characteristics of the light-emitting element 1 and the comparative light-emitting element 2. FIG. 15 shows voltage-current density characteristics. FIG. 16 shows luminance-external quantum efficiency characteristics. Note that the measurements of the light-emitting elements were performed at room temperature (in an atmosphere maintained at 23° C.).

Table 2 shows the element characteristics of the light-emitting element 1 and the comparative light-emitting element 2 at around 1000 cd/m².

TABLE 2

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 1 | 2.80 | 0.886 | (0.336, 0.629) | 800 | 90.3 | 101.3 | 24.3 |
| Comparative light-emitting element 2 | 3.00 | 1.250 | (0.338, 0.627) | 1018 | 81.5 | 85.3 | 21.9 |

Figure 17:
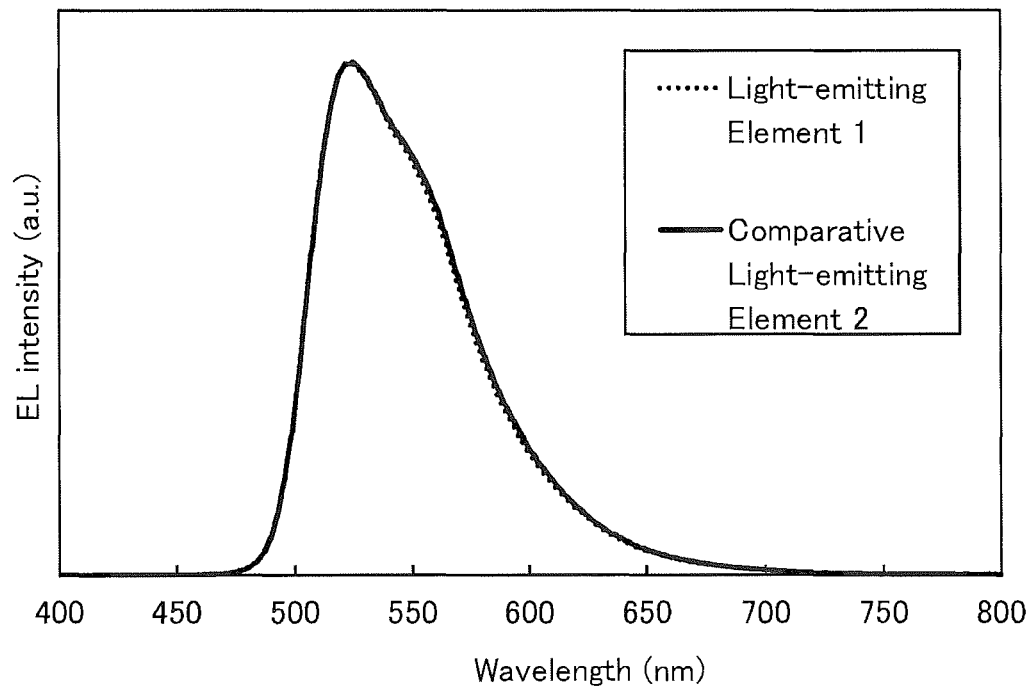
FIG. 17 shows electroluminescence spectra of light-emitting elements in Example.

FIG. 17 shows electroluminescence spectra of the light-emitting element 1 and the comparative light-emitting element 2 to which a current at a current density of 2.5 mA/cm² was supplied.

As shown in FIG. 14, FIG. 16, and Table 2, the light-emitting element 1 and the comparative light-emitting element 2 exhibited high current efficiency and high external quantum efficiency. In addition, the light-emitting element 1 exhibited higher current efficiency and higher external quantum efficiency than the comparative light-emitting element 2. Here, because of having a low HOMO level (−5.31 eV), the guest material Ir(ppy)$_2$(mdppy) might form an exciplex with the host material 4Ph-2,8mDBtP2Bfpm or 4,8mDBtP2Bfpm. When forming an exciplex with the host material, the guest material becomes less likely to contribute to light emission, which reduces the emission efficiency of the light-emitting element. It is thus preferable to select the host material and the guest material that do not form an exciplex in combination with each other. Here, the LUMO level of 4,8mDBtP2Bfpm (the organic compound used in the comparative light-emitting element 2) is −3.02 eV. The LUMO level of 4Ph-2,8mDBtP2Bfpm (the organic compound of one embodiment of the present invention used in the light-emitting element 1) is −2.99 eV, which is higher than that of 4,8mDBtP2Bfpm. A compound with a lower LUMO level is more likely to form an exciplex with a guest material. Therefore, the organic compound of one embodiment of the present invention is less likely to form an exciplex with the guest material and thus allows a light-emitting element to have high emission efficiency.

As shown in FIG. 15 and Table 2, the light-emitting element 1 and the comparative light-emitting element 2 each have favorable driving voltage.

As shown in FIG. 17, the electroluminescence spectra of the light-emitting element 1 and the comparative light-emitting element 2 respectively have spectrum peaks at around 523 nm and 525 nm and full widths at half maximum of 69 nm and 71 nm, indicating that the light-emitting element 1 and the comparative light-emitting element 2 exhibited favorable green light emission derived from their guest materials.

As described above, it was found that a light-emitting element with high emission efficiency and low driving voltage can be fabricated by using a compound of one embodiment of the present invention in a light-emitting layer.

REFERENCE NUMERALS

100: EL layer, 101: electrode, 102: electrode, 106: light-emitting unit, 108: light-emitting unit, 111: hole-injection layer, 112: hole-transport layer, 113: electron-transport layer, 114: electron-injection layer, 115: charge generation layer, 116: hole-injection layer, 117: hole-transport layer, 118: electron-transport layer, 119: electron-injection layer, 120: light-emitting layer, 140: light-emitting layer, 141: host material, 141_1: organic compound, 141_2: organic compound, 142: guest material, 150: light-emitting element, 170: light-emitting layer, 250: light-emitting element, 601: source side driver circuit, 602: pixel portion, 603: gate side driver circuit, 604: sealing substrate, 605: sealant, 607: space, 608: lead wiring, 610: element substrate, 611: switching TFT, 612: current controlling TFT, 613: electrode, 614: insulator, 616: EL layer, 617: electrode, 618: light-emitting element, 623: n-channel TFT, 624: p-channel TFT, 900: portable information terminal, 901: housing, 902: housing, 903: display portion, 905: hinge portion, 910: portable information terminal, 911: housing, 912: display portion, 913: operation button, 914: external connection port, 915: speaker, 916: microphone, 917: camera, 920: camera, 921: housing, 922: display portion, 923: operation button, 924: shutter button, 926: lens, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025B: lower electrode, 1025G: lower electrode, 1025R: lower electrode, 1025W: lower electrode, 1026: partition, 1028: EL layer, 1029: electrode, 1031: sealing substrate, 1032: sealant, 1033: base material, 1034B: coloring layer, 1034G: coloring layer, 1034R: coloring layer, 1035: black layer, 1036: overcoat layer, 1037: interlayer insulating film, 1040: pixel portion, 1041: driver circuit portion, 1042: peripheral portion, 2100: robot, 2101: illuminance sensor, 2102: microphone, 2103: upper camera, 2104: speaker, 2105: display, 2106: lower camera, 2107: obstacle sensor, 2108: moving mechanism, 2110: arithmetic device, 3500: multifunction terminal, 3502: housing, 3504: display portion, 3506: camera, 3508: lighting, 3600: light, 3602: housing, 3608: lighting, 3610: speaker, 5000: housing, 5001: display portion, 5002: second display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5120: dust, 5140: portable electronic device, 5150: portable information terminal, 5151: housing, 5152: display region, 5153: bend portion, 8501: lighting device, 8502: lighting device, 8503: lighting device, 8504: lighting device, 9000: housing, 9001: display portion, 9006: connection terminal, 9055: hinge, 9200: portable information terminal, 9201: portable information terminal, 9202: portable information terminal This application is based on Japanese Patent Application Serial No. 2017-123227 filed with Japan Patent Office on Jun. 23, 2017, the entire contents of which are hereby incorporated by reference.

The invention claimed is:

1. An organic compound represented by General Formula (G0),

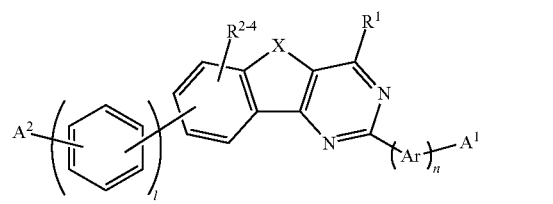

(G0)

wherein in General Formula (G0):

X represents oxygen or sulfur;

each of $A^1$ and $A^2$ independently represents a substituted or unsubstituted aromatic hydrocarbon group having 6 to 30 carbon atoms or a substituted or unsubstituted heteroaromatic hydrocarbon group having 3 to 30 carbon atoms;

Ar represents a substituted or unsubstituted arylene group having 6 to 25 carbon atoms;

each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms;

n is an integer of 0 to 4;

l is an integer of 1 to 4; and the organic compound comprises oxygen and sulfur.

2. An organic compound represented by General Formula (G1),

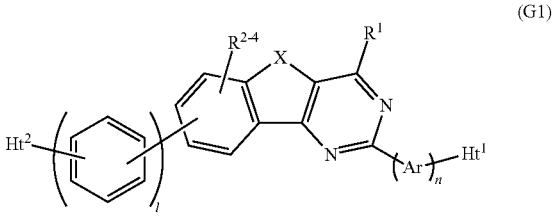

(G1)

wherein in General Formula (G1):

X represents oxygen or sulfur;

Ar represents a substituted or unsubstituted arylene group having 6 to 25 carbon atoms;

each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms;

n is an integer of 0 to 4;

l is an integer of 1 to 4; and each of $Ht^1$ and $Ht^2$ independently represents a substituted or unsubstituted fused heteroaromatic ring, wherein the fused heteroaromatic ring comprises one or more of a carbazole skeleton, a dibenzofuran skeleton, and a dibenzothiophene skeleton, wherein the fused heteroaromatic ring has 12 to 30 carbon atoms, and wherein the organic compound comprises oxygen and sulfur.

3. The organic compound according to claim 2, wherein the organic compound is represented by General Formula (G2),

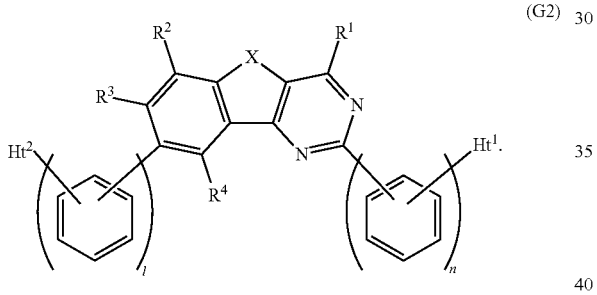

(G2)

4. The organic compound according to claim 2, wherein the organic compound is represented by General Formula (G3),

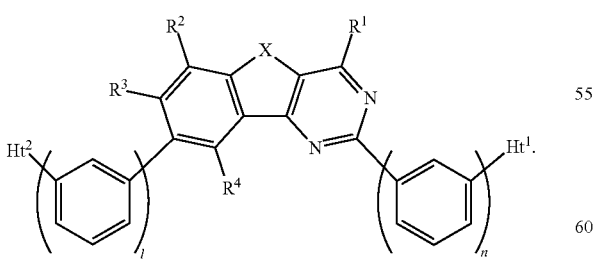

(G3)

5. The organic compound according to claim 2, wherein each of the $Ht^1$ and the $Ht^2$ independently represents any of groups represented by General Formulae (Ht-1) to (Ht-4):

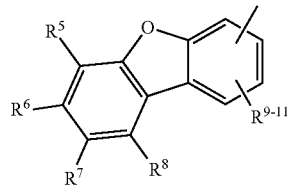

(Ht-1)

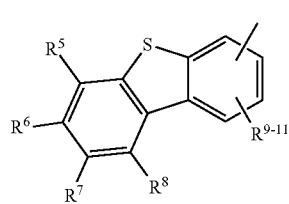

(Ht-2)

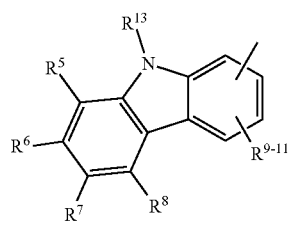

(Ht-3)

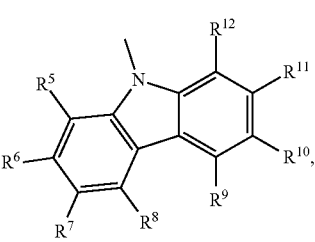

(Ht-4)

wherein in General Formulae (Ht-1) to (Ht-4):

each of $R^5$ to $R^{13}$ independently represents hydrogen, an alkyl group having 1 to 6 carbon atoms, a substituted or unsubstituted cycloalkyl group having 3 to 7 carbon atoms, a substituted or unsubstituted aryl group having 6 to 25 carbon atoms, or a substituted or unsubstituted heteroaromatic hydrocarbon group having 12 to 30 carbon atoms.

6. The organic compound according to claim 5, wherein $R^5$ to $R^8$ are bonded to each other to form a saturated ring or an unsaturated ring, or $R^9$ to $R^{12}$ are bonded to each other to form a saturated ring or an unsaturated ring.

7. The organic compound according to claim 2, wherein the organic compound is represented by General Formula (G4),

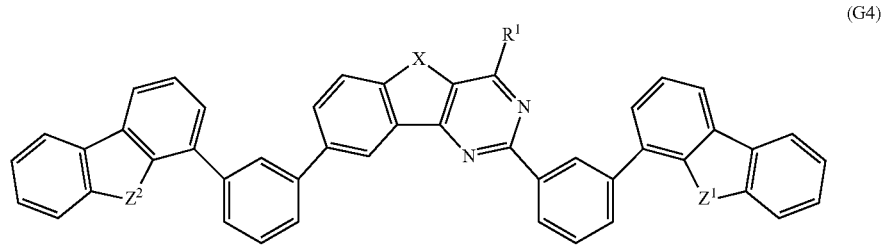

(G4)

wherein in General Formula (G4):
each of X, $Z^1$, and $Z^2$ independently represents oxygen or sulfur; and
$R^1$ represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

8. The organic compound according to claim 7, wherein the organic compound is represented by Structural Formula (100),

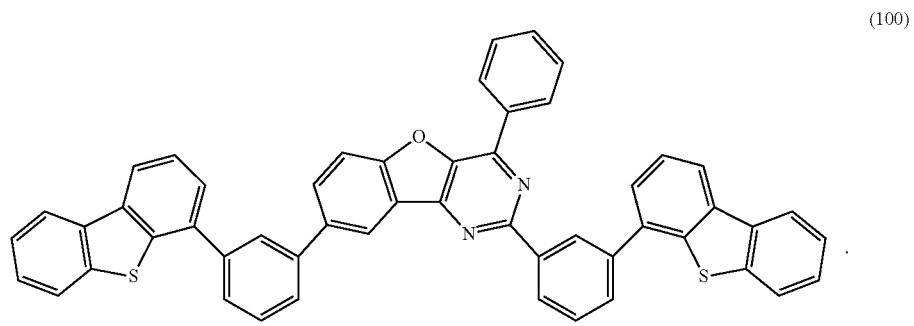 [SMILES: c1ccc(-c2nc(-c3cccc(-c4cccc5c4sc4ccccc45)c3)nc3c2oc2ccc(-c4cccc(-c5cccc6c5sc5ccccc56)c4)cc23)cc1]

(100)

9. A light-emitting element comprising the organic compound according to claim 2.

10. A display device comprising:
the light-emitting element according to claim 9; and
at least one of a color filter and a transistor.

11. An electronic device comprising:
the display device according to claim 10; and
at least one of a housing and a touch sensor.

12. A lighting device comprising:
the light-emitting element according to claim 9; and
at least one of a housing and a touch sensor.

13. The organic compound according to claim 1, wherein X represents oxygen.

* * * * *